US008217226B2

(12) United States Patent
Caillet et al.

(10) Patent No.: US 8,217,226 B2
(45) Date of Patent: Jul. 10, 2012

(54) NUCLEIC ACIDS AND PROTEINS ASSOCIATED WITH GALACTOMANNAN SYNTHESIS IN COFFEE

(75) Inventors: Victoria Caillet, Monnaie (FR); James Gèrard McCarthy, Noizay (FR); Vincent Petiard, Tours (FR); Steven D. Tanksley, Dryden, NY (US); Chenwei Lin, Menlo Park, CA (US)

(73) Assignees: Nestec, S. A., Vevey (CH); Cornell University, Ithaca, NY (US)

( * ) Notice: Subject to any disclaimer, the term of this patent is extended or adjusted under 35 U.S.C. 154(b) by 437 days.

(21) Appl. No.: 12/083,467

(22) PCT Filed: Oct. 16, 2006

(86) PCT No.: PCT/US2006/040556
§ 371 (c)(1),
(2), (4) Date: Dec. 3, 2009

(87) PCT Pub. No.: WO2007/047675
PCT Pub. Date: Apr. 26, 2007

(65) Prior Publication Data
US 2010/0154075 A1      Jun. 17, 2010

Related U.S. Application Data

(60) Provisional application No. 60/726,602, filed on Oct. 14, 2005.

(51) Int. Cl.
*C12N 15/82* (2006.01)
*C12N 15/10* (2006.01)
*C12N 15/00* (2006.01)
*A01H 5/00* (2006.01)
*A01H 5/10* (2006.01)

(52) U.S. Cl. ........ 800/284; 800/278; 800/295; 800/298; 435/320.1; 435/468; 536/23.1; 536/23.6

(58) Field of Classification Search .................. None
See application file for complete search history.

(56) References Cited

FOREIGN PATENT DOCUMENTS

| WO | WO 99/01558 A | 1/1999 |
|----|---------------|--------|
| WO | WO 99/60103 | 11/1999 |
| WO | WO 2004/046197 A1 | 3/2004 |

OTHER PUBLICATIONS

UNIPROT:Q564G6, Reid et al, May 10, 2005, provided in Applicants IDS.*
Database Genesq [Online], Aug. 26, 2004, "C tetragonoloba galactosyltransferase protein SeqID4," XP002440813, retrieved from EBI accession No. GSP: ADO57402, see abstract, the protein has 67.2% identity with SEQ ID No. 15.
Database UniProt [Online], May 10, 2005, "Galactomannan galactosyltransferase." XP002440814, retrieved from EBI accession No. UNIPROT:Q564G6, The sequence is 68.2% identical to SEQ ID No. 15.
Database Genesq [Online], May 10, 1999, "Arabidopsis Golgi glycosytransferase gt16," XP002440815 retrieved from EBI accession No. GSP:AAW90188. The sequence is 61.2% identical with SEQ ID No. 15.
Database Genesq [Online], Mar. 27, 2000, "Fenugreek galactomannan galactosyltransferase," XP002440816, retrieved from EBI accession No. GSP:AAY58262, Database accession No. AAY58262. The sequence is 57.7% identical with SEQ ID No. 15.
Database Genesq [Online], Oct. 1, 2003, "Galactomannan galactosyltransferase," XP002440817, retrieved from EBI accession No. UNIPROT:Q7X9N4. The sequence is 57.7% identical with SEQ ID No. 15.
Edwards, M. et al., "The seeds of *Lotus japonicus* lines transformed with sense, antisense, and sense/antisense galactomannan galactosyltransferase constructs have structurally altered galactomannans in their endosperm cell walls," *Plant Physiology*, Rockville, MD, US, vol. 134, Mar. 2004, pp. 1153-1162, XP002982658, ISSN: 0032-0889, see the whole document.
Database EMBL [Online], Nov. 22, 2004, "Nicotiana benthamiana mRNA for alpha-6-galactosyltransferase (x34.3 gene)," XP002440818, retrieved from EBI accession No. EMBL:AJ8647019, Database accession No. A864709. The sequence has 62.5% identity with SEQ ID No. 14.
Database EMBL [Online], Nov. 17, 2005, "CGN-38882 Seed of Late Development Stage *Coffea canephora* cDNA clone cccs46w8o23 5', mRNA sequence," XP002440819, retrieved from EBI accession No. EMBL:DV694396, Database accession No. DV694396. The sequence is 99% identical with SEQ ID No. 11.
Chenwei, L. et al., "Coffee and tomato share common gene repertoires as revealed by deep sequencing of seed and cherry transcripts," *Theoretical and Applied Genetics; International Journal of Plant Breeding Research*, Springer-Verlag, BE, vol. 112, No. 1, Dec. 1, 2005, pp. 114-130, XP019322122, ISSN: 1432-2242, see the whole document.
Edwards, M. et al., "Molecular characterization of a membrane-bound galactosyltransferase of plant cell wall matrix polysaccharide biosynthesis," *Plant Journal*, Blackwell Scientific Publications, Oxford, GB, vol. 19, No. 6, 1999, pp. 691-697, XP002982656, ISSN: 0960-7412, see the whole document.
Redgwell, R. et al., "Changes to the galactose/mannose ratio in galactomannans during coffee bean (*Coffea arabica* L.) development: Implications for in vivo modification of galactomannans synthesis," *Planta*, (Berlin), vol. 217. 217, No. 2, Jun. 2003, pp. 316-326, XP002440799, ISSN: 0032-0935, see the whole document.
Keegstra, K. et al., "Plant glycosyltransferases," *Current Opinion in Plant Biology*, Quadrant Subscription Services, GB, vol. 4, No. 3, Jun. 2001, pp. 219-224, XP002357035, ISSN: 1369-5266.
Altschul, S.F. et al, "Gapped BLAST and PSI-BLAST: A New Generation of Protein Database Search Programs," *Nucleic Acids Research*, vol. 25(17), pp. 3389-3402, 1997.
Bacic, A. et al., "Structure and Function of Plant Cell Walls," In J Priess, ed, *The biochemistry of plants; a comprehensive treatise*, vol. 14 Carbohydrates, Academic Press, New York, pp. 297-371, 1988.
Buckeridge, M. et al., "Mobilization of Storage Cell Wall Polysaccharides in Seeds," *Plant Physiol Biochem.*, vol. 38: 141-156, 2000.
Charles-Bernard, M. et al., "Interactions Between Volatile and Non-Volatile Coffee Components 1. Screening of Non-Volatile Components," *J Agric Food Chem.*, vol. 53: 4417-4425, 2005.

(Continued)

*Primary Examiner* — Brent T Page
(74) *Attorney, Agent, or Firm* — Potter Anderson & Corroon LLP

(57) ABSTRACT

Disclosed herein are nucleic acid molecules isolated from coffee (*Coffea* spp.) comprising sequences that encode mannan synthase or galactomannan galactosyltransferase. Also disclosed are methods for using these polynucleotides for gene regulation and manipulation of the polysaccharide molecules of coffee plants, to influence extraction characteristics and other features of coffee beans.

18 Claims, 21 Drawing Sheets

OTHER PUBLICATIONS

Crouzillat, D. et al., "*Theobroma cacao* L.: A Genetic Linkage Map and Quantitative Trait Loci Analysis," *Theor Appl Genet.*, vol. 93, pp. 205-214, 1996.

Cutler, S. and Somerville, C. "Cellulose Synthesis: Cloning in Silico," *Curr Biol.*, vol. 7: R108-R111, 1997.

Dhugga, K. S. et al., "Guar Seed Beta-Mannan Synthase is a Member of the Cellulose Synthase Super Gene Family," *Scinece*. vol. 303(5656):363-6, 2004.

Edwards, M. et al., "The Seeds of *Lotud japonicus* Lines Transformed With Sense, Antisense, and Sense/Antisense Galactomannan Galactosyltransferase Constructs Have Structurally Altered Galactomannans in Their Endosperm Cell Walls," *Plant Physiol.*, vol. 134: 1153-1162, 2004.

Edwards, M. et al. "Control of Mannose/Galactose Ratio During Galactomannan Formation in Developing Legume Seeds," *Planta*, vol. 187: 67-74, 1992.

Fischer, M. et al., "Polysaccharides of Green Arabica and Robusta Coffee Beans," *Carbohydrate Research*, vol. 330: 93-101, 2001.

Fry, S. "Primary Cell Wall Metabolism: Tracking the Careers of Wall Polymers in Living Plant Cells," *New Phytologist*, vol. 161: 641-675, 2004.

Hanford, M. et al., "Localisation and Characterization of Cell Wall Mannan Polysaccharides in *Arabidopsis thaliana*," *Planta*, vol. 218: 27-36, 2003.

Hazen, S. P. et al., "Cellulose Synthase-Like Genes of Rice," *Plant Physiol.*, vol. 128, pp. 336-340, 2002.

Joersbo, M. et al., "In Vivo Modification of the Cell Wall Polysaccharide Galactomannan of Guar Transformed With an Alph-Galactosidase Gene Cloned From Senna," *Molecular Breeding*, vol. 7: 211-219, 2001.

Keegstra, K. and Raikhel, N. "Plant Glycosyltransferases," *Curr Opin Plant Biol.*, vol. 4: 219-224, 2001.

Liepman, A. et al., "Expression of Cellulose Synthase-Like (Csl) Genes in Insect Cells Reveals That CsIA Family Members Encode Mannan Synthases," *Proc Natl Acad Sci.*, vol. 102: 2221-2226, 2005.

Lundqvist, J. et al., Isolation and Characterization of Galactomannan From Spruce (*Picea abies*), *Carbohydr Polym*, vol. 48, 29-39, 2002.

Marraccini, P. et al., "Molecular Cloning of the Complete 11S Seed Storage Protein Gene of Coffea Arabica and Promoter Analysis in the Transgenic Tobacco Plants," *Plant Physiol. Biochem.*, vol. 37, pp. 273-282, 1999.

Marraccini, P. et al., "Coffee Plant With Reduced Alpha-D-Galactosidase," EP1436402, 2004. (Patent).

Marraccini, P. et al., "Molecular and Biochemical Characterization of Endo-Beta-Mannanases From Germination Coffee (*Coffea arabica*) Grains," *Planta*, vol. 213: 296-308, 2001.

Marraccini, P. et al., "Rubisco Small Subunit of *Coffea arabica*: Cdna Sequence, Gene Cloning and Promoter Analysis in Transgenic Tobacco Plants," *Plant Physiol. Biochem.*, vol. 41:17-25, 2003.

Marraccini, P. et al., "Biochemical and Molecular Characterization of Alpha-D-Galactosidase From Coffee Beans," *Plant Physiology and Biochemistry*, 2005.

Matheson, M. "Mannose-Based Polysaccharides," *Methods Plant Biochem.*, vol. 12: 371-413, 1990.

Nunes, F. et al., *J Agric Food Chem.*, vol. 45: 3238-3243, 1997.

Oosterveld, A. et al., "Extraction and Characterization of Polysaccharides From Green and Roasted Coffea Arabica Beans," *Carbohydrate Polymers*, vol. 52: 285-296, 2003.

Pettolino, F. et al., "A (1-4)-Beta-Mannan Specific Monoclonal Antibody and Its Use in the Immunocytochemical Location of Galactomannans," *Planta*, vol. 214: 235-242, 2001.

Redgwell, R. et al., "Changes to the Galactose/Mannose Ratio in Galactomannans During Coffee Bean (*Coffea arabica* L.) Development: Implications for in Vivo Modification of Galactomannan Synthesis," *Planta*, vol. 217: 316-326, 2003.

Redgwell, R.J. et al., "Effect of Roasting on Degradation and Structural Features of Polysaccharides in Arabica Coffee Beans," *Carbohydrate Research*, vol. 337: 421-431, 2002.

Reid, J. "Structure and Function in Legume-Seed Polysaccharides," In C Brett, J Hillman, eds., *Biochemistry of Plant Cell Walls*, Cambridge University Press, Cambridge, pp. 259-268, 1985.

Reid J. and Bewley, J. "A Dual Role for the Endosperm and its Galactomannan Reserves in the Germinative Physiology of Fenugreek (*Trigonella foenum-graecum* L.) An Endospermic Leguminous Seed," *Planta*, vol. 147: 145-150, 1979.

Richmond, T. A. and Somerville, C. R. "The Cellulose Synthase Superfamily," *Plant Physiol.*, vol. 124: 495-498, 2000.

Schroder, R. et al., "Purification and Characterization of a Galactoglucomannan From Kiwi Fruit (*Actinidia deliciosa*)," *Carbohydr Research*. vol. 331, 291-306, 2001.

Sims, I. et al., "Structural Characterization of Galactoglucomannan Secreted by Suspension-Cultured Cells of *Nicotiana plumbaginifolia*," *Carbohydr Research*. vol. 303, 79-92, 1997.

Somerville, C. et al., "Toward a Systems Approach to Understanding Plant Cell Walls," *Science*, vol. 306: 2206-2211, 2004.

Sunderland, P. et al., "Cytochemistry and Immunolocalization of Polysaccharides and Proteoglycans in the Endosperm of Green Arabica Coffee Beans," *Protoplasma*, vol. 223: 203-211, 2004.

Yeretzian, C. et al., "From the Green Bean to the Coffee Cup: Investigating Coffee Roasting by On-Line Monitoring of Volatiles," *Eur Food Res Technol.*, vol. 214: 92-104, 2005.

\* cited by examiner

| | | |
|---|---|---|
| pVC2 | | 260 |
| pVC3 | | 340 |
| pVC4 | TTGGTTACATTGGAACAATTGTCCCTACTTAAGAAGCTAGGCATACGGAAAATAAAGCCT | 1736 |
| pVC6 | TTGGTTACATTGGAACAATTGTCCCTACTTAAGAAGCTAGGCATACGGAAAATAAAGCCT | 1735 |
| pVC7 | TTGGTTACATTGGAACAATTGTCCCTACTTAAGAAGCTAGGCATACGGAAAATAAAGCCT | 1735 |
| cccs46w16i11 insert | TTGGTTACATTGGAACAATTGTCCCTACTTAAGAAGCTAGGCATACGGAAAATAAAGCCT | 1581 |
| cccs46w24c19 insert | TTGGTTACATTGGAACAATTGTCCCTACTTAAGAAGCTAGGCATACGGAAAATAAAGCCT | 1119 |
| pVC2 | | 260 |
| pVC3 | | 340 |
| pVC4 | CCAAAAGGAGAAGCAGGGTGCTGGAAGCTACTGTCATTTGGTATATCCATCTAGTAGCAT | 1796 |
| pVC6 | CCAAAAGGACAAGCACCCTCCTGGAAGCTACTGTCATTTGGTATATCCATCTTGTAGCAT | 1795 |
| pVC7 | CCAAAAGGAGAAGCAGGGTGCTGGAAGCTACTGTCATTTGGTATATCCATCTTGTAGCAT | 1795 |
| cccs46w16i11 insert | CCAAAAGGACAAGCACCCTCCTGGAAGCTACTGTCATTTGGTATATCCATCTGTAGCAT | 1641 |
| cccs46w24c19 insert | CCAAAAGGACAAGCAGGGTGCTGGAAGCTACTGTCATTTGGTATATCCATCTAGTAGCAT | 1179 |
| pVC2 | | 260 |
| pVC3 | | 340 |
| pVC4 | ACTACTAAGTCATGGTATTATTTTTCAATGTTCTTTATACTGAGTGTCCTCAAGGGTCTC | 1856 |
| pVC6 | ACTACTAAGTCATGGTATTATTTTTCAATGTTCTTTATACTGTGTGTCCTCAAGGGTCTC | 1855 |
| pVC7 | ACTACTAAGTCATGGTATTATTTTTCAATGTTCTTTATACTGTGTGTCCTCAAGGGTCTC | 1855 |
| cccs46w16i11 insert | ACTACTAAGTCATGGTATTATTTTTCAATGTTCTTTATACTGTGTGTCCTCAAGGGTCTC | 1701 |
| cccs46w24c19 insert | ACTACTAAGTCATGGTATTATTTTTCAATGTTCTTTATACTGTGTGCCTCAAGGGTCTC | 1239 |
| pVC2 | | 260 |
| pVC3 | | 340 |
| pVC4 | TGCACTTCGGGCCCCCCTTAATATAGACGAGTACAGCAAGTC | 1898 |
| pVC6 | TGCACTTCGGGCCCCCCTTAATATAGACGAGTACAGCAAGTC | 1897 |
| pVC7 | TGCACTTCGGGCCCCCCTTAATATAGACGAGTACAGCAAGTC | 1897 |
| cccs46w16i11 insert | TGCACTTCGGGCCCCCCTTAATATAGACGAGTACAGCAAGTCAACTTGGTTCTTGAAT.. | 1759 |
| cccs46w24c19 insert | TGCACTTCGGGCCCCCCTTAATATAGACGAGTACAGCAAGTCAACTTGGTTCTTGAATAA | 1299 |
| pVC2 | | 260 |
| pVC3 | | 340 |
| pVC4 | | 1898 |
| pVC6 | | 1897 |
| pVC7 | | 1897 |
| cccs46w16i11 insert | ..............................AAAAAAAAAAAAAAAAAAAA | 1779 |
| cccs46w24c19 insert | AAATGTAATTCACTGGTACCCATGTTTTAAAAAAAAAAAAAAAAAAAAAA | 1349 |

Fig. 2E

```
1    MRNSVFLEPE PEVNLYDDTG RSLSQAWDRI RVPIIVPILR FALYVCIAMS VMRFIERVYM
61   AIVIGCVKCL GRKRYTKYNL DAIKEDLEQN RNYPMVLVQI PMFNEKEVYK LSIGAACGLS
121  WPSDRLIVQV LDDSTNEVLR ALVELECQRW IEKGVNVKYE TRNNRNGYKA GALRDGLKKP
181  YVEDCEFVVI FDADFQPEED FLWRTVPYLL ENPELALVQA RWKFVNANEC LMTRLQEMPL
241  DYHFSVEQEV GSSTCSFFGF NGTAGVWRIQ AVSDAGGWKD RTTVEDMDLA VRASLKGWKF
301  IFVGDLSVKN ELPSTFKAYR FQQHRWSCGP ANLFRKMFKE ILLCERVSIW KKFHVIYAFS
361  FVRKIVAHWV TFFFYCIVIP ATILVPEVHL PKPIAVYLPA TITLLNAAST PRSLHLLVFW
421  ILFENVMSLH RSKAAIIGLL EASRVNEWIV TEKLGNALKQ KYSIPKVSKR PRSRIAERIH
481  FLELIMGMYM LHCAFYNMIF ANDHFFIYLL LQAGAFFIIG LGYIGTIVPT
```

Figure 3

```
CcManS   ----MRNSVFLEPEPEVNLYDDTGRSLSQAWDRIRVPIIVPILRFALYVCIAMSVMRFIE    56
CaManS   ----MRNSVFLEPEPEVNLYDDTGRSLSQAWDRIRVPIIVPILRFALYVCIAMSVMLFIE    56
pVC4     ----MRNSVSLESEPEVNLYDDTGRSLSQAWDRIRVPIIVPILRFALYVCIAMSVMLFIE    56
CtManS   ----MRNLIEEPE---GIPGNSSSSLRYAWQSIRAPVIIPLLKLAVIMCSVMSILMLFVE    53
AtManS   --MELGDTTSVIPDSFMGYRDDITMQMSMVLDQIRIAPLLVPALRLGVYICLTMSVMLFVE    58
ItManS   MAGETINEVELMMPELRGPGGDMAAQMRLMYDLVKAPLLVPVLRLAVYMCLTMSMMLFVE    60

CcManS   RVYMAIVIGCVKCLGRKRYTKYNLDAIKEDLEQ-NRNYPMVLVQIPMFNEKEVYKLSIGA   115
CaManS   RVYMAIVIGCVKCLGRKRYTKYNLDAIKEDLEQ-NRNYPMVLVQIPMFNEKEVYKLSIGA   115
pVC4     RAYMAIVIGCVKCLGRKRYTKYNLDAIKEDLEQ-NRNYPMVLVQIPMFNEKEVYKLSIGA   115
CtManS   RVAMAAVILIVKVLRKKRYTKYNLEAMKQKLER-SKKYPMVLIQIPMYNEKEVNKLSIGA   112
AtManS   RVYMGIVISLVKLFGRKPDKRFKYEPLKDDIELGNSAKPMVLIQLPMFNEREVYQLSIGA   118
ItManS   RLYMGIVLILVKIFCGKPEKRYKWEPMREDYEIGTSVFPSVLIDIPMFNEKEVYKISIGA   120
                                *
CcManS   ACGLSWPSDRLIVQVLDDSTNEVLRALVELECQRWIEKGVNVKYETRNNRNGYKAGALRD   175
CaManS   ACGLSRPSDRLIVQVLDDSTNEVLRALVELECQRWIEKGVNVKYETRNNRNGYKAGALRD   175
pVC4     ACGLSWPSDRLIVQVLDDSTNEVLRALVELECDRWIEKGVNVEYETRNNRNGYLAGALRD   175
CtManS   VCGLSWPADRFIVQVLDDSTNPVLRELMEMECQKWLQKGVNVKYENRIRNRNGYKAGALKE   172
AtManS   ACGLSWPSDRIVIQVLDDSTDPTIKDLVEMECSRMASKGVNIIKYEIRDNRNGYKAGALKE   178
ItManS   VCNFAWPSDRLVVQVLDDSTDHNIKEMVEKECLRWASKGINITYIQTRVTRGGYKAGALKE   180
                           * *
CcManS   GLKKPYVEDCEFVVIFDADFQPEEDFLWRTVPYLLENPELALVQARWKFVNANECLMTRL   235
CaManS   GLKLPYVEDCEFVVIFDADFQPEEDFLWRTVPYLLENPELALVQARWKFVNANECLMTRL   235
pVC4     GLKRPYVEGCEFVVIFDADFQPEEDFLWRTVPYLLENPELALVQARWKFVNANECLMTRL   235
CtManS   GLEKQYVEDCEFVIAFDADFQRDADFLWNTIPYLLENPKLGLVQARWKFVNSEECMMTRL   232
AtManS   BMKKSYVKSCDYVALFDADFQPEADFLWRTVPYLLHNPKLALVQARWKFVNSDECLMTRM   238
ItManS   GLTHDYVQDCEYVALFDADFREEPDFLLKSIPFLIHNPEIALIQARWRFVNADECLLTRM   240

CcManS   QEMPLDYHFSVMEQEVGSSTICSFFGFNGTAGVWRIQAVSDAGGWKDRTJTVEDMDLAVRASL   295
CaManS   QEMSLDYHFSVEQEVGSSTCSFFGENGTAGVWRIQAVSDAGGWKDRTTVEDMDLAVRASL   295
pVC4     QEMSLDYHFSVEQEVGSSTCSFFGFNGTAGVWRIQAVSDAGGWKDRTTVEDMDLAVRASL   295
CtManS   QEMSLDYHFSVEQEVGSSTYSFFGFNGTAGVWRIQAIKDAGGWKDRTTVEDMDLAVRASL   292
AtManS   QEMSLDYHFTVEQEVGSSTYAFFGFNGTAGIWRISALNEAGGWKDRTTVEDMDLAVRASL   298
ItManS   QEMSLDYHFKVEQEVGSSTHAFFGFNGTGGIWRIAAINEAGGWKDRTTVEDMDLAVRAGL   300
                                                              *
CcManS   KGWKFIFVGDLSVKNELPSLFKAYREQQHRWSCGPANLFRKMFKEILLCERVSIWKKFHV   355
CaManS   KGWKFIEVGDLSVKNELPSIFKAYREQQHRWSCGPANLFRKMFKEILLCERVSIWKKFHV   355
pVC4     KGWKFIFVGDLISVKNELPSIFKAYREQQHRWSCGPANL(X)MFKEILLCERVSIWKKFHV   355
CtManS   HGWEFVFVGDVKVKNELPSIFKAYREQQHRWSCGPANLFKKMTKEIICCKRVPLLKRLHL   352
AtManS   KGWKELYLGSEKVLNELPSTEKAYRYQQHRWSCGPANLFRKMAFEIMTNKNVTLWKKVHVI   358
ItManS   KGWKFLYLGDLHVKSELPSTFKAFRFQQHRWSCGPANLFRKMFMEILVRNKRVNVWKKVYV   360

CcManS   IYAFSFVRKIVAHWVTFFFYCIVLPATILVPEVHLPKPIAVYLPATITLLNAASTPRSLH   415
CaManS   IYAFFFVRKIVAHWVTFFFYCIVLPATILVPEVHLPKPIAVYPPATITLLNAASTPRSLH   415
pVC4     IYAFFFVRKIVAHWVTFFFYCIVLPATILVPEVHLPKPIAVYPPATITLLNAASTPRSLH   415
CtManS   IYAFFFEVRKIVAHWVTFFFYCIVLPACVIVPEVNLKKQLAIYIPATITILNAVSTPRSMH   412
AtManS   LYSFFVVRKLVAHIVTPLFYCVLLPATVLVPEVTVPKWGAVYIPSVITLLNAVGTPRSLH   418
ItManS   IYSFFLVRKTTAHMVTFFFYCVVLPLTILVPEMEVRKWGAIYIPCITTILNSVGTPRSIH   420

CcManS   LLVFWILFENVMSLHRSKAAITGLLEASRVNEWIVTEKLGNALK--QKYSIPKVSKRPRS   473
CaManS   LLVFWILFENVMSLHRSKAAIIGLLEASRVNEWIVTEKLGNALK--QKYSIPKVSKRPGS   473
pVC4     LLVFWILFENVMSLHRSKAAILDLLEASRVNEWIVTEKLGNALK--QKYSIPKVSKRPRS   473
CtManS   LLVLWILFENVMSLHRTKAAIIGLLEANRVNEWVTEKLGNAMK--QR-NNARPSRASRF   469
AtManS   LMVEWILFENVMSLHRTKATFIGLLEGGRVNEWIVTEKLGDVK---AKSATKTSKKVIRF   475
ItManS   LLFYWILFENVMSFHRTKATLIGLLEFKRANEWVTEKLGDAINNNNKSNSKPAPKKTKS   480

CcManS   RIAERIHFLELIMGMYMLHGAFYNMIFANDHFFIYLLLQAGAFFILGLGYIGTIVPT      530
CaManS   RIAERLHFLELIMGMYMLHCAFYNLIFANDHFFIYLLLQAGAFFILGLGYIGTIVPT      530
pVC4     RIAERIHFLELIMGMYMLHCAFYNMLFANDHFFIYLLLQAGAFFTIGLGYIGTIVPTM     531
CtManS   RIIERIHPLEIIVGMYMLHGATYDLLFGHDHEVYLLLQAGAFFITMGFGLVGTIVPT      526
AtManS   RFGDRLHVLELIGVGMYLLFVGCYDAFEGKNHYYLYLFAQAIAEFIAGFGQIGTIVENH   533
ItManS   IFKDRILLHELGFAVFLFVCGVYDYLHGKNHYYIVLFLQVITFTIAGVGWVGTIVPS     537
```

```
unigene 122567  - - - - - - - - - - - - - - - - - - - - - - - - - - - - - - - - - - - - - - - - - - - - - -   0
Fenugreek GMGT  A T K F G S K N K S S P W L S N G C I F L G A M S A L L M I W G L N S F I A P I P H S N  45
Japonicus GMGT  M A R L G S R N K S S L W L S D G C C F L T G A L S A L L L V W G L C S F I I P F N T D  45 unigene 122567  - - - - - - - - - - - - - - - - - - - - - - - - - - - - - - F Y D E F K L T Y  10
Fenugreek GMGT  P K F N S F T T K L K S I N F T T N - - T N F A G P D L L H D P S D K T F Y D D F E T C Y  88
Japonicus GMGT  P K L N S V A A K L K S L N L P R N Q I T S S A Q D L L Y D S P E T T F Y D D P E M S I Y  90 unigene 122567  T - L G K T I K D W D K K R K S W L N L H P S F A A G A D T F L I V T G S Q P S P C K N  54
Fenugreek GMGT  T M M D K P M K N W D K R K E W L F H H D S F A A G A T E K L L V I T G S Q D T K C D N  133
Japonicus GMGT  T - M D K P V T K W D E K R Q W L L H H P S F A A G A S D R L L L V T G S Q P K R C H N  134 unigene 122567  P I G D H L L R C F K N K A D Y S R L N G Y D I F Y M T A C D P K L C N V F A K V A L  99
Fenugreek GMGT  P I G D H L L L R F Y K N K V D Y C R I N H D I I Y N N A L L T P K M D S Y W A K Y F M  178
Japonicus GMGT  P I G D H L L L R F F K N K V D Y Q R I H D I D I I Y N N A L L H P K M N S Y W A K Y P V  179 unigene 122567  I R A A M V A H P E A F W I W W M D S D A V F T D K Y F K V F L Q R Y K Q H N L V V P G W  144
Fenugreek GMGT  V R A P M L A H P E V E M I W W V D S D A I F T D M F K L P W R Y K D H W D V I A G W  223
Japonicus GMGT  V K A A M I A H P E V E W I W W V D S D A V I T D M E P K L P L N K Y N E F K L I I H G W  224 unigene 122567  P D M V Y E K K S W V S L N T C S F F T N H Q W S L D F L D A M A R M S P R S D D Y K F  189
Fenugreek GMGT  E E L V K T E S W T G L N A G V F L M R N C Q W S L D F K D V W A S M G P N S P E Y E K  268
Japonicus GMGT  L D L V K K F H S W T G L N A G V F L M R N C Q N S L D F M D V W A A M G P S S R D Y K K  269 unigene 122567  W S E T L M S  196
Fenugreek GMGT  W G E R L R E T F K T K V R D S D D Q T A L A Y L I A M G E D K W T K K L Y M E N E Y Y  313
Japonicus GMGT  W G E K L M A T F K D K V I P D S D D Q T A L A Y L I A M G E D K W T E K I Y L E K D Y Y  314 unigene 122567  196
Fenugreek GMGT  P E G Y N L E I S K M Y D K M G E R Y D E I E K F V E G L F R R H A E K V S E R Y G E M R  358
Japonicus GMGT  P E G Y N V S L A K M Y E N V S V R Y D E V E R R V G G L R R R H A E K V S R R Y G D N P  359 unigene 122567  196
Fenugreek GMGT  S E Y V K N L G D M R R P E F T H F T G C Q P C N G H H N F I Y A E D C N G M E R A L  403
Japonicus GMGT  D E H V K Y F G Q W R R P F I T H F T G C C P C N G H H N H A Y A A D D C W N C M D R A L  404 unigene 122567  196
Fenugreek GMGT  N F A A D N Q V L R K F G F I H P N L L D K S V S P L P F G Y P A A S P  438
Japonicus GMGT  N F A D N Q V L R T Y G Y V R R S L N D K A V T F I P Y D I P A A  437
```

Figure 6

```
                        10        20        30        40
cccs46w8o23                                                              0
GMGT-RACE13 (pVC10)   A G A C A G C A G C C A C C A T G C C T A A G C A C A A C A G C C T C C T C C G  40
CaGMGT1 (pVC11)       A G A C A G C A G C C A C C A T G C C T A A G C A C A A C A G C C T C C T C C G  40
unigene 122620                                                           0 cccs46w8o23                                                              0
GMGT-RACE13 (pVC10)   C A C C A A A A C C T C G T C G T T T T T T C T C C A G C T G C T T T C T T T A C  80
CaGMGT1 (pVC11)       C A C C A A A A C C T C G T C G T T T T T T C T C C A G C T G C T T T C T T T A C  80
unigene 122620                                                           0 cccs46w8o23                                                              0
GMGT-RACE13 (pVC10)   G C C G C C G G A A C T T C C G C T T C C T T T T T G T T A G C C T G G G C C T  120
CaGMGT1 (pVC11)       G C C G C C G G A A C T T C C G C T T C C T T T T T G T T A G C C T G G G C C T  120
unigene 122620                                                           0 cccs46w8o23                                                              0
GMGT-RACE13 (pVC10)   T C T G G T C C T T C T T C A G T A G C C C C G C C C C A T C T G C G A A T C C  160
CaGMGT1 (pVC11)       T C T G G T C C T T C T T C A G T A G C C C C G C C C C A T C T G C G A A T C C  160
unigene 122620                                                           0 cccs46w8o23                                                              0
GMGT-RACE13 (pVC10)   C T C T T T C T C G A G G G G C C T A G C T T C C G A G G C T G C C C T C A G C  200
CaGMGT1 (pVC11)       C T C T T T C T C G A G G G G C C T A G C T T C C G A G G C T G C C C T C A G C  200
unigene 122620                                                           0 cccs46w8o23                                                              0
GMGT-RACE13 (pVC10)   T G C C C C G C C G G G A A A G C G G G T C A C A A C C G G A G C T A C G A T C  240
CaGMGT1 (pVC11)       T G C C C C G C C G G G A A A G C G G G T C A C A A C C G G A G C T A C G A T C  240
unigene 122620                                                           0 cccs46w8o23                                                              0
GMGT-RACE13 (pVC10)   C G C C C G A C C C G A C T T T C T A T G A C G A C C C G G T A T T G A G C T A  280
CaGMGT1 (pVC11)       C G C C C G A C C C G A C T T T C T A T G A C G A C C C G G A A T T G A G C T A  280
unigene 122620                                                           0 cccs46w8o23                                                              0
GMGT-RACE13 (pVC10)   C A C C A T T G A G A A G A C C A T C A A G A A C T G G G A T G A G A A G A G G  320
CaGMGT1 (pVC11)       C A C C A T T G A G A A G A C C A T C A A G A A C T G G G A T G A G A A G A G G  320
unigene 122620                                                           0 cccs46w8o23                                                              0
GMGT-RACE13 (pVC10)   C G G G A G T G G C T C G A G A A G C A T C C C T C G T T C G C C G C C G G A G  360
CaGMGT1 (pVC11)       C G G G A G T G G C T C G A G A A G C A T C C C T C G T T C G C C G C C G G A G  360
unigene 122620                                                           0 cccs46w8o23                                                              0
GMGT-RACE13 (pVC10)   C A G C T G A C A G G A T T T T A A T G G T C A C G G G T T C T C A G G C G A C  400
CaGMGT1 (pVC11)       C A G C T G A C A G G A T T T T A A T G G T C A C G G G T T C T C A G G C G A C  400
unigene 122620                                                           0 cccs46w8o23                                                              0
GMGT-RACE13 (pVC10)   G C C C T G C A A G A A C C C G A T C G G G G A T C A C T T G C T G T T G A G G  440
CaGMGT1 (pVC11)       G C C C T G C A A G A A C C C G A T C G G G G A T C A C T T G C T G T T G A G G  440
unigene 122620                                                           0 cccs46w8o23                                                              0
GMGT-RACE13 (pVC10)   T T C T T C A A G A G T A A G G C G G A C T A C T G C A G G A T C C A C G G C T  480
CaGMGT1 (pVC11)       T T C T T C A A G A A T A A G G C G G A C T A C T G C A G G A T C C A C G G C T  480
unigene 122620                                                           0 cccs46w8o23                                                              0
GMGT-RACE13 (pVC10)   A C G A T A T C T T C T A C A A C A C C G T G C T G C T G C A G C C G A G G A T  520
CaGMGT1 (pVC11)       A C G A T A T C T T C T A C A A C A C C G T G C T G C T G C A G C C G A A G A T  520
unigene 122620                                                           0 cccs46w8o23                                                              0
GMGT-RACE13 (pVC10)   G T T C T C G T T T T G G G C A A A A A T G C C T G C C G T G A A A G C G G T C  560
CaGMGT1 (pVC11)       G T T C T C G T T T T G G G C A A A A A T G C C T G C C G T G A A A G C G G T C  560
unigene 122620                                                           0 cccs46w8o23                                                              0
GMGT-RACE13 (pVC10)   A T G T T G G C C C A T C C G G A G G C G G A G T G G A T C T G G T G G G T A G  600
CaGMGT1 (pVC11)       A T G T T G G C C C A T C C G G A G G C G G A G T G G A T C T G G T G G G T A G  600
unigene 122620                                                           0 cccs46w8o23                                                              0
GMGT-RACE13 (pVC10)   A T T C A G A C G C A G C C T T C A C C G A C A T G G A C T T C A C G C T G C C  640
CaGMGT1 (pVC11)       A T T C A G A C A C A G C C T T C A C C G A C A T G G A C T T C A C G C T G C C  640
unigene 122620                                                           0 cccs46w8o23                                                              0
GMGT-RACE13 (pVC10)   G C T G G A T C G C T A C A A G G C C C A T A A T T T A G T G G T C C A C G G C  680
CaGMGT1 (pVC11)       G C T G G A T C G C T A C A A G G C C C A T A A T T T A G T G G T C C A C G G C  680
unigene 122620                                                           0 cccs46w8o23                                                              0
GMGT-RACE13 (pVC10)   T G G C C T C A C T T G A T T C A C A G G G A G A A G A G C T G G A C G G G G C  720
CaGMGT1 (pVC11)       T G G C C T C A C T T G A T T C A C A G G G A G A A G A G C T G G A C G G G G C  720
unigene 122620                                                           0
```

Figure 8 (page 1 of 3)

Figure 8 (page 2 of 3)

Figure 8 (page 3 of 3)

Figure 9 (page 1 of 2)

```
CaGMGT1 (pVC11)   E - R E K H G H K I Y M E D E S Y F E G Y R H E I V G A L E N I T D A Y T G I E   336
# CAB52246        G - E D K H T K K I Y H E N E Y Y F P G Y H L E I S K M Y D K M G E R Y D E I E   336
# CAI11452        G - E R K W R S K I H A I T D Y S L H G Y H L G I V N R F D K I E N Y T K I E   332
# CAI11453        G - E R K W R S K I H A I T D Y S L H G Y H L G I W D R F D N I E G N Y E K I D   332
# CAI11454        G - E D K H T K K I Y K E N E Y Y F B G Y H H E I S K M Y D K M G K K Y D E I E   336
# ABE79594        Q - R R K M G A K T F L E E G Y D L K G Y W I A T M G K L E G I Q N K Y D E I E   324
# CAI79402        D N K D T H R E K I F L E S E Y Y F E G Y W L E I V K Y Y E H I S E R Y D E V S   337
# CAI79403        E - K S K W A D R I Y L E S E Y Y F E G Y H K E H W E T Y E N E D K A H E V E   346
# CAD98924        G - E D K H T E K I Y L E K D Y I F E G Y R V E L A K M Y H S V S V R Y D E V E   337

CaGMGT1 (pVC11)   K R E R P L R R H A E R V G E S Y G K V F E H H K D A G Y G R G S W R R P F   376
# CAB52246        K R V E G L R R H A E K V S E R Y G E M R E E Y V K N L - - - - G D M R R P F   372
# CAI11452        R D V P K L R R H A E A V S D S Y A E A R E P L L A E G A D G K G G H R R P F   372
# CAI11453        R D V P K L R R P H A E S V S B S Y A A A R E P L V A E G G D W K G G W R R P F   372
# CAI11454        K R V E G L R R H A E K V S E R Y G E M R E E Y V H N L - - - - G D M R R P F   372
# ABE79594        K K A A V L R H R I S E K V S V H L G E M R E P Y L E - - - - - H S E R R I T   358
# CAI79402        R K V E G L R R H A E K V S S K Y G A M R E E Y E K - - - - - D N K R H E F   371
# CAI79403        R K V R S L R R R H A E K V S E G V G A V R E P Y V M V R S G E M R E F   386
# CAD98924        R R V G G L R R R H A E K V S E R Y G E M R E A M V Y F - - - - E Q R H E F   373

CaGMGT1 (pVC11)   H I H F T G C Q P C G G D H N Q N Y D G Q E W D N Q E R Y H U R    416
# CAB52246        I T H F T G C Q P C N G H H H P I Y A A D D H N G L E R A M D N V E R     412
# CAI11452        I T H F T G C Q P C S G D H A A E Y V G D S H V G M E R E Y L N G D V E S   412
# CAI11453        I T H F T C C Q P C S G D H V S E Y V G D K G H V G M E R A L N L A D N V A R   412
# CAI11454        I T H F T G C Q P C N G H H N P H G A A D D H N G H E R R V H E N Y E A R   412
# ABE79594        V K H F T G C Q P C S G D H N P S Y K G D V C H K E R R D I K I R     398
# CAI79402        I T H F T G C Q P C N G H H N P A N N A N D G H N G H E R E E E I L R   411
# CAI79403        I T H F T G C Q P C S G N H N A M Y E P D A G H N G H N K H I L E Y Y R   426
# CAD98924        I H H F T G C Q P C N G H H P A Y A A D D G H N G H D R E D H Y G R   413

CaGMGT1 (pVC11)   R Y G E V H R D E W D T A T V F R L L R G S F H S W T S G       448
# CAB52246        K F G F I R P N L L D K S - S R F H G Y H A S P               438
# CAI11452        N F G F M H D D I K S N S P Y S R N H F H E S E E F V         443
# CAI11453        N F G F M H V D I K S N S P Y T F V N H F H E E V E E F V     443
# CAI11454        K F G F I R P N L L D K S - S H F H G H H K S P               438
# ABE79594        N H G Y V R K N H M T S H - Y Y E V H G H R D                 422
# CAI79402        T H G Y H R Q N H H R K S - E S H H G H H A                   435
# CAI79403        K F G Y Y F P D L Q D N S - S S H I H G H A                   449
# CAD98924        T Y G Y Y R R S N H K A - V T H I H Y H G A                   437
```

Figure 9 (page 2 of 2)

Figure 10 (page 1 of 2)

```
unigene 122567                                                                              859
CcGMGT2 (ccc126f9)   C C C T C C T A C G T T G G A A A T A C C T G C T G G G A T G C A A T G G A G A  1240 unigene 122567                                                                              859
CcGMGT2 (ccc126f9)   G G A C T C T G A A T T A T G C T G A T A A T C A G G T C C T T C G T A A C T T  1280 unigene 122567                                                                              859
CcGMGT2 (ccc126f9)   G G G T T T T G T G C A C A G G G A T A T A A G C C G T G G C T C T T A C G T T  1320 unigene 122567                                                                              859
CcGMGT2 (ccc126f9)   T T A C C C C T A G C C T T T G A T T T T C C A T C G G A A G T G C T G C A A A  1360 unigene 122567                                                                              859
CcGMGT2 (ccc126f9)   G A A A G A A A T C C G G T G A A G A A T A T A A C A G G T G A A T A A A T C C  1400 unigene 122567                                                                              859
CcGMGT2 (ccc126f9)   C T C C G T T T T A G T G C T G T T T A T A G A T T A T A G C A G C C A G C A G  1440 unigene 122567                                                                              859
CcGMGT2 (ccc126f9)   G A C T T G G G C C C T G A A A A T T C A G T A T C T C A G A A A A A A A A T G  1480 unigene 122567                                                                              859
CcGMGT2 (ccc126f9)   A C A G T G A A A T T G A G A G A G C A A A A T G T T T T C A C A A G C T T G  1520 unigene 122567                                                                              859
CcGMGT2 (ccc126f9)   T C G T G G T A A A T T C C T C A G T A A T T G A G T G A A T T T C A A G A T A  1560 unigene 122567                                                                              859
CcGMGT2 (ccc126f9)   C T T A T A T T T G T T G C C A C G A A A T T T G T T G A T G C T T T T T C C T  1600 unigene 122567                                                                              859
CcGMGT2 (ccc126f9)   G T T G G T C A A C A A A A T C G A A T T G A T T G A G T G T G C T T T T T A A  1640 unigene 122567                                                                              859
CcGMGT2 (ccc126f9)   T A A A A A A A A A A A A A A A A A A A A A A A A A A A A A A A A A A A A A A A  1680 unigene 122567                                                                              859
CcGMGT2 (ccc126f9)   A A A A A A A A A A A A A A A                                                   1695
```

Figure 10 (page 2 of 2)

Figure 11 (page 1 of 2)

Figure 11 (page 2 of 2)

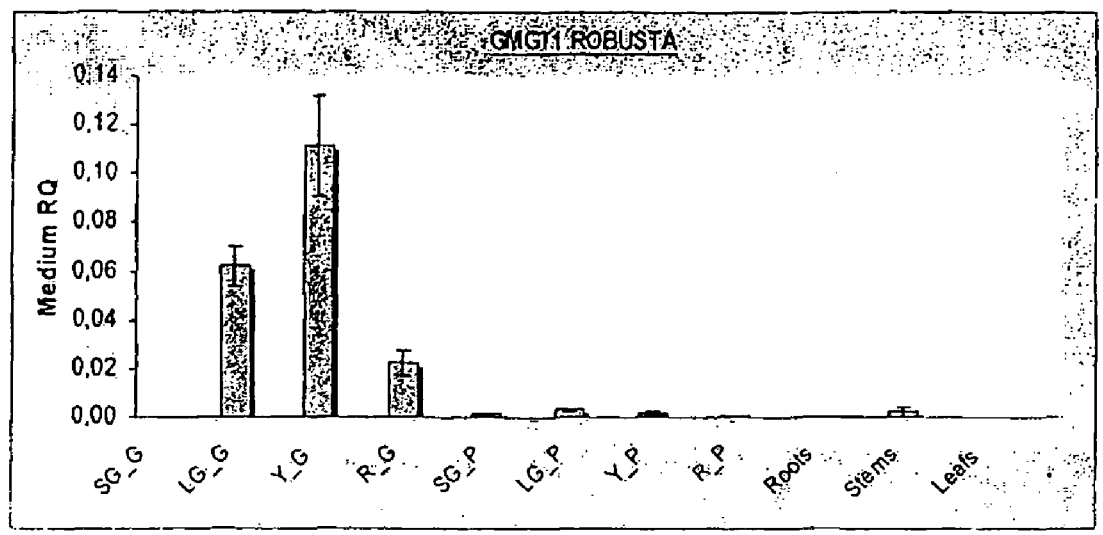
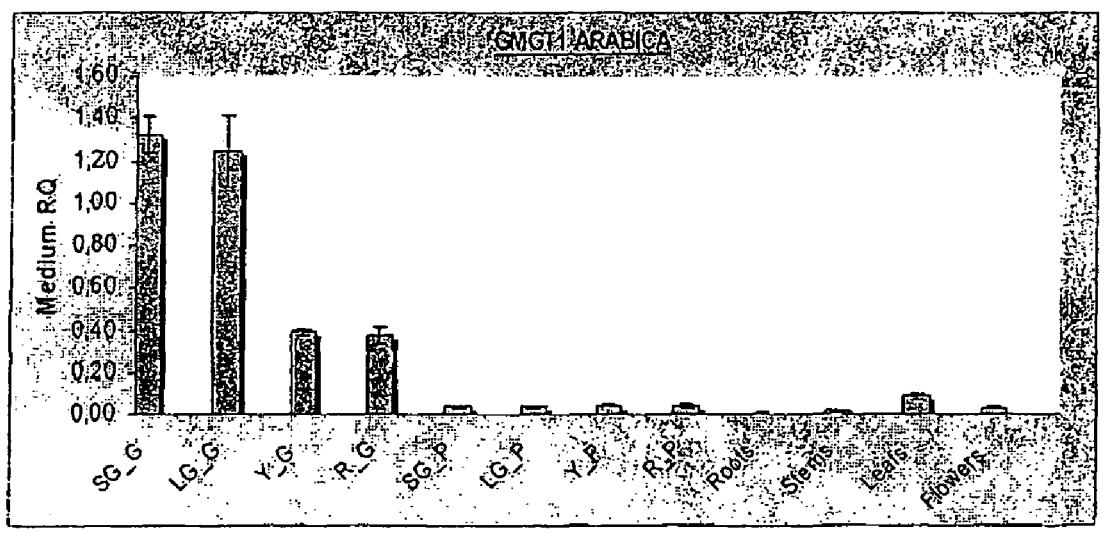
Figure 12

SEQUENCE LISTING

<160> NUMBER OF SEQ ID NOS: 59

<210> SEQ ID NO 1
<211> LENGTH: 1898
<212> TYPE: DNA
<213> ORGANISM: Coffea canephora
<220> FEATURE:
<221> NAME/KEY: misc_feature
<222> LOCATION: (1118)..(1118)
<223> OTHER INFORMATION: n=any nucleotide

<400> SEQUENCE: 1

| | | | | | |
|---|---|---|---|---|---|
| ctgctcattg | ccctcagctc | ctaagggctc | tatcattttg | gcttcaagtt | caagttcttc | 60 |
| ttcaccttca | aaaaagcatt | tcgttgctcc | acttccacaa | tcatagcctg | ataaaatgag | 120 |
| aaactcagtt | tctctagagt | ccgagccaga | ggtaaattta | tatgatgata | ctggcagaag | 180 |
| tctcagccaa | gcatgggacc | gtatacgagt | tcctataatt | gtgccaattc | tgcggtttgc | 240 |
| tttatatgta | tgcatagcaa | tgtctgttat | gcttttcatt | gaacgggcgt | acatggcgat | 300 |
| tgtgattgga | tgtgtcaagt | gcttgggaag | gaaacgatat | accaagtata | atcttgatgc | 360 |
| cataaaagaa | gacctagagc | aaaacagaaa | ctatcctatg | gtgctggtcc | aaatacccat | 420 |
| gtttaacgaa | aaagaggtct | ataaactctc | aattggagct | gcatgtgggc | tttcatggcc | 480 |
| atcagataga | ttaatagttc | aggttcttga | tgactccacg | aatgaagtcc | tgcgggcatt | 540 |
| ggtggagttg | gagtgtcaaa | gatggataga | gaaagggggtg | aatgtggagt | atgaaacaag | 600 |
| gaacaacagg | aatggttata | aagcaggtgc | acttcgggat | ggtctaaaaa | ggccatatgt | 660 |
| tgaaggttgt | gagtttgtcg | tcattttttga | tgcagacttc | cagcctgagg | aggactttct | 720 |
| gtggagaaca | gtgccttatc | ttcttgaaaa | cccagagctg | gctttggttc | aagcccgatg | 780 |
| gaaatttgta | aatgcaaatg | aatgtttaat | gacgcggctt | caggagatgt | cactagacta | 840 |
| tcacttcagt | gtggagcaag | aagtaggctc | gtcaacatgt | tcattctttg | ggtttaatgg | 900 |
| aactgccggt | gtatggagga | tccaagcagt | aagtgatgct | ggtggatgga | aagataggac | 960 |
| cacggttgag | gatatggacc | ttgcagtaag | ggctagcctt | aagggttgga | aattcatctt | 1020 |
| tgtgggagat | ttatctgtca | aaaatgaact | tccaagcact | ttcaaggctt | atagatttca | 1080 |
| gcagcatcga | tggtcgtgtg | gcccagccaa | tctcttcnga | aaaatgttca | aagaaattct | 1140 |
| cctttgtgag | cgtgtgtcca | tctggaagaa | attccatgtc | atctatgcct | tcttctttgt | 1200 |
| gaggaagata | gttgcacact | gggttacttt | tttcttctac | tgcattgtga | tcccagcaac | 1260 |
| tatcttagtt | cctgaagtgc | atcttccaaa | gccaatagca | gtttatctgc | cagcaaccat | 1320 |
| tacacttctt | aatgcagcta | gcactccaag | gtccttgcat | ctactcgtgt | tctggatact | 1380 |
| gtttgagaat | gtcatgtccc | tccatcgatc | caaagcagca | attataggac | ttttagaagc | 1440 |
| cagccgagtt | aacgagtgga | ttgtgacgga | aaagcttgga | aacgcattga | agcaaaagta | 1500 |
| cagcatcccc | aaagtatcta | agagaccaag | atcacgaatt | gcagaaagga | tccacttttt | 1560 |
| ggagctgata | atgggaatgt | atatgctgca | ctgtgctttc | tacaacatga | tctttgcaaa | 1620 |

```
cgatcatttc ttcatatacc tgttacttca agcaggggct ttcttcacaa tagggcttgg    1680
ttacattgga acaattgtcc ctacttaaga agctaggcat accgaaaata aagcctccaa    1740
aaggacaagc aggctgctgg aagctactgt catttggtat atccatctag tagcatacta    1800
ctaagtcatg gtattatttt tcaatgttct ttatactgag tgtcctcaag ggtctctgca    1860
cttcgggccc cccttaatat agacgagtac agcaagtc                            1898

<210> SEQ ID NO 2
<211> LENGTH: 1897
<212> TYPE: DNA
<213> ORGANISM: Coffea canephora

<400> SEQUENCE: 2
tgctcattgc cctcagctcc taagggctct atcattttgg cttcaagttc aagttcttct      60
tcaccttcaa aaaagcattt cgttgcttca cttccacaat tatagcctga taagatgaga     120
aactcagttt ttctagagcc cgagccgag gtaaattat atgatgatac tggcagaagt       180
ctcagccaag catgggaccg tatacgagtt cctataattg tgccgattct gcggtttgct     240
ttatatgtat gcatagcaat gtctgttatg cgtttcattg aacgggtgta catggcgatt     300
gtgattggat gtgtcaagtg cttgggaagg aaacgatata ccaagtataa tcttgatgcc     360
ataaaagaag acctagagca aaacagaaac tatcctatgg tgctggtcca aatacccatg     420
tttaacgaaa aagaggtcta taaactctca attggagctg catgtgggct tcatggccca    480
tcagatagac taatagttca ggttcttgat gactccacga atgaagtcct gcgggcattg    540
gtggagttgg agtgtcaaag atggatagag aaaggggtga atgtgaagta tgaaacaagg    600
aacaacagga atggttataa agcaggtgca cttcgggatg gtctaaaaaa gccatatgtt    660
gaagattgtg agttcgtcgt cattttgat gcagacttcc agcctgagga ggactttctg     720
tggagaacag tgccttatct tcttgaaaac ccagagctgg ctttggttca agcccgatgg    780
aaatttgtaa atgcaaatga atgtttaatg acgcggcttc aggagatgcc actagactat    840
cacttcagtg tggagcaaga agtaggctcg tcaacatgtt cattctttgg gtttaatgga    900
actgccggtg tatggaggat ccaagcagta agcgatgctg gtggatggaa agataggacc    960
acggttgagg atatggacct tgcagtaagg gctagcctta agggctggaa attcatcttt   1020
gtgggagatt tatctgtcaa aaatgaactt ccaagcactt tcaaggctta tagatttcag   1080
cagcatcgat ggtcgtgtgg cccagccaat ctcttcagaa aaatgttcaa agaaattctc   1140
ctttgtgagc gtgtgtccat ctggaagaaa ttccatgtca tctatgcctt ctcctttgtg   1200
aggaagatag ttgcacactg ggttactttt ttcttctact gcatcgtgat cccagcaact   1260
atcttagttc ctgaagtgca tcttccaaag ccaatagcag tttatctgcc agcaaccatt   1320
acacttctta atgcagctag cactccaagg tccttgcatc tactcgtgtt ctggatactg   1380
tttgagaatg tcatgtccct ccatcgatcc aaagcagcaa ttataggact tttagaagcc   1440
agccgagtta acgagtggat tgtgacggaa aagcttggaa acgcattgaa gcaaaagtac   1500
agcatcccca agtatctaa gagaccaaga tcacgaattg cagaaaggat ccacttttg      1560 gagctgataa tgggaatgta tatgctgcac tgtgctttct acaacatgat ctttgcaaac   1620
gatcatttct tcatataccct gttacttcaa gcaggggctt tcttcataat agggcttggt   1680
tacattggaa caattgtccc tacttaagaa gctaggcata ccgaaaataa agcctccaaa   1740
aggacaagca ggctgctgga agctactgtc atttggtata tccatcttgt agcatactac   1800
taagtcatgg tattattttt caatgttctt tatactgtgt gtcctcaagg gtctctgcac   1860
```
ttcgggcccc ccttaatata gacgagtaca gcaagtc                      1897

<210> SEQ ID NO 3
<211> LENGTH: 1897
<212> TYPE: DNA
<213> ORGANISM: Coffea arabica

<400> SEQUENCE: 3
tgctcattgc cctcagctcc taagggctct atcattttgg cttcaagttc aagttcttct    60
tcaccttcaa aaaagcattt cgttgcttca cttccacaat tatagcctga taagatgaga   120
aactcagttt ttctagagcc cgagccagag gtaaatttat atgatgatac tggcagaagt   180
ctcagccaag catgggaccg tatacgagtt cctataattg tgccgattct gcggtttgct   240
ttatatgtat gcatagcaat gtctgttatg cttttcatcg aacgggtgta catggcgatt   300
gtgattggat gtgtcaagtg cttgggaagg aaacgatata ccaagtataa tcttgatgcc   360
ataaaagaag acctagagca aaacagaaac tatcctatgg tgctggtcca aatacccatg   420
tttaacgaaa aagaggtcta taaactctca attggagctg catgtgggct ttcacggcca   480
tcagatagac taatagttca ggttcttgat gactccacga atgaagtcct gcgggcattg   540
gtggagttgg agtgtcaaag atggatagag aaaggggtga atgtgaagta tgaaacaagg   600
aacaacagga atggttataa agcaggtgca cttcggaatg gtctaaaaaa gccatatgtt   660
gaagattgtg agtttgtcgt cattttgat gcagacttcc agcctgagga ggactttctg    720
tggagaacag tgccttatct tcttgaaaac ccagagctgg cttgggttca gcccgatgg    780
aaatttgtaa atgcaaatga atgtttaatg acgcggcttc aggagatgtc actagactat    840
cacttcagtg tggagcaaga gtaggctcg tcaacatgtt cattctttgg gtttaatgga    900
actgccggtg tatggaggat ccaagcagta agtgatgctg gtggatggaa agataggacc    960
acggttgagg atatggacct tgcagtaagg gctagcctta agggttggaa attcatcttt   1020
gtgggagatt tatctgtcaa aaatgaactt ccaagcactt tcaaggctta tagatttcag   1080
cagcatcgat ggtcgtgtgg cccagccaat ctcttcagaa aaatgttcaa agaaattctc   1140
cttttgtgagc gtgtgtccat ctggaagaaa ttccatgtca tctatgcctt cttctttgtg   1200
aggaagatag ttgcacactg ggttactttt ttcttctact gcatcgtgat cccagcaact   1260
atcttagttc ctgaagtgca tcttccaaag ccaatagcag tttatccgcc agcaaccatt   1320
acacttctta atgcagctag cactccaagg tccttgcatc tactcgtgtt ctggatactg   1380
tttgagaatg tcatgtccct ccatcgatcc aaagcagcaa ttataggact tttagaagcc   1440
agccgagtta acgagtggat tgtgacggaa aagcttggaa acgcattgaa gcaaaagtac   1500
agcatcccca aagtatctaa gagaccagga tcacgaattg cagaaaggat ccacttttg   1560
gagctgataa tgggaatgta tatgctgcac tgtgctttct acaacctgat cttttgcaaac   1620
gatcatttct tcatataccc gttacttcaa gcaggggctt tcttcataat agggcttggt   1680
tacattggaa caattgtccc tacttaagaa gctaggcata ccgaaaataa agcctccaaa   1740
aggacaagca ggctgctgga agctactgtc atttggtata tccatcttgt agcatactac   1800
taagtcatgg tattatttt caatgttctt tatactgtgt gtcctcaagg gtctctgcac   1860
ttcgggcccc ccttaatata gacgagtaca gcaagtc                            1897

<210> SEQ ID NO 4
<211> LENGTH: 530
<212> TYPE: PRT
<213> ORGANISM: Coffea canephora
<220> FEATURE:
<221> NAME/KEY: MISC_FEATURE
<222> LOCATION: (335)..(335)
<223> OTHER INFORMATION: X = any amino acid, preferably any naturally
      occuring amino acid.

<400> SEQUENCE: 4

Met Arg Asn Ser Val Ser Leu Glu Ser Glu Pro Glu Val Asn Leu Tyr
1               5                   10                  15

Asp Asp Thr Gly Arg Ser Leu Ser Gln Ala Trp Asp Arg Ile Arg Val
            20                  25                  30

Pro Ile Ile Val Pro Ile Leu Arg Phe Ala Leu Tyr Val Cys Ile Ala
        35                  40                  45

Met Ser Val Met Leu Phe Ile Glu Arg Ala Tyr Met Ala Ile Val Ile
    50                  55                  60

Gly Cys Val Lys Cys Leu Gly Arg Lys Arg Tyr Thr Lys Tyr Asn Leu
65                  70                  75                  80

Asp Ala Ile Lys Glu Asp Leu Glu Gln Asn Arg Asn Tyr Pro Met Val
                85                  90                  95

Leu Val Gln Ile Pro Met Phe Asn Glu Lys Glu Val Tyr Lys Leu Ser
            100                 105                 110

Ile Gly Ala Ala Cys Gly Leu Ser Trp Pro Ser Asp Arg Leu Ile Val
        115                 120                 125

Gln Val Leu Asp Asp Ser Thr Asn Glu Val Leu Arg Ala Leu Val Glu
    130                 135                 140

Leu Glu Cys Gln Arg Trp Ile Glu Lys Gly Val Asn Val Glu Tyr Glu
145                 150                 155                 160

Thr Arg Asn Asn Arg Asn Gly Tyr Lys Ala Gly Ala Leu Arg Asp Gly
                165                 170                 175

Leu Lys Arg Pro Tyr Val Glu Gly Cys Glu Phe Val Val Ile Phe Asp
            180                 185                 190

Ala Asp Phe Gln Pro Glu Glu Asp Phe Leu Trp Arg Thr Val Pro Tyr
        195                 200                 205

Leu Leu Glu Asn Pro Glu Leu Ala Leu Val Gln Ala Arg Trp Lys Phe
    210                 215                 220

Val Asn Ala Asn Glu Cys Leu Met Thr Arg Leu Gln Glu Met Ser Leu
225                 230                 235                 240

Asp Tyr His Phe Ser Val Glu Gln Val Gly Ser Ser Thr Cys Ser
                245                 250                 255

Phe Phe Gly Phe Asn Gly Thr Ala Gly Val Trp Arg Ile Gln Ala Val
            260                 265                 270

Ser Asp Ala Gly Gly Trp Lys Asp Arg Thr Thr Val Glu Asp Met Asp
        275                 280                 285

Leu Ala Val Arg Ala Ser Leu Lys Gly Trp Lys Phe Ile Phe Val Gly
    290                 295                 300

Asp Leu Ser Val Lys Asn Glu Leu Pro Ser Thr Phe Lys Ala Tyr Arg
305                 310                 315                 320

Phe Gln Gln His Arg Trp Ser Cys Gly Pro Ala Asn Leu Phe Xaa Lys
                325                 330                 335

Met Phe Lys Glu Ile Leu Leu Cys Glu Arg Val Ser Ile Trp Lys Lys
            340                 345                 350

Phe His Val Ile Tyr Ala Phe Phe Phe Val Arg Lys Ile Val Ala His
        355                 360                 365

Trp Val Thr Phe Phe Phe Tyr Cys Ile Val Ile Pro Ala Thr Ile Leu
    370                 375                 380

```
Val Pro Glu Val His Leu Pro Lys Pro Ile Ala Val Tyr Leu Pro Ala
385                 390                 395                 400

Thr Ile Thr Leu Leu Asn Ala Ala Ser Thr Pro Arg Ser Leu His Leu
            405                 410                 415

Leu Val Phe Trp Ile Leu Phe Glu Asn Val Met Ser Leu His Arg Ser
        420                 425                 430

Lys Ala Ala Ile Ile Gly Leu Leu Glu Ala Ser Arg Val Asn Glu Trp
            435                 440                 445

Ile Val Thr Glu Lys Leu Gly Asn Ala Leu Lys Gln Lys Tyr Ser Ile
    450                 455                 460

Pro Lys Val Ser Lys Arg Pro Arg Ser Arg Ile Ala Glu Arg Ile His
465                 470                 475                 480

Phe Leu Glu Leu Ile Met Gly Met Tyr Met Leu His Cys Ala Phe Tyr
                485                 490                 495

Asn Met Ile Phe Ala Asn Asp His Phe Phe Ile Tyr Leu Leu Leu Gln
            500                 505                 510

Ala Gly Ala Phe Phe Thr Ile Gly Leu Gly Tyr Ile Gly Thr Ile Val
            515                 520                 525

Pro Thr
    530

<210> SEQ ID NO 5
<211> LENGTH: 530
<212> TYPE: PRT
<213> ORGANISM: Coffea canephora

<400> SEQUENCE: 5

Met Arg Asn Ser Val Phe Leu Glu Pro Glu Pro Glu Val Asn Leu Tyr
1               5                   10                  15

Asp Asp Thr Gly Arg Ser Leu Ser Gln Ala Trp Asp Arg Ile Arg Val
            20                  25                  30

Pro Ile Ile Val Pro Ile Leu Arg Phe Ala Leu Tyr Val Cys Ile Ala
        35                  40                  45

Met Ser Val Met Leu Phe Ile Glu Arg Val Tyr Met Ala Ile Val Ile
    50                  55                  60

Gly Cys Val Lys Cys Leu Gly Arg Lys Arg Tyr Thr Lys Tyr Asn Leu
65              70                  75                  80

Asp Ala Ile Lys Glu Asp Leu Glu Gln Asn Arg Asn Tyr Pro Met Val
                85                  90                  95

Leu Val Gln Ile Pro Met Phe Asn Glu Lys Glu Val Tyr Lys Leu Ser
            100                 105                 110

Ile Gly Ala Ala Cys Gly Leu Ser Arg Pro Ser Asp Arg Leu Ile Val
        115                 120                 125

Gln Val Leu Asp Asp Ser Thr Asn Glu Val Leu Arg Ala Leu Val Glu
130                 135                 140

Leu Glu Cys Gln Arg Trp Ile Glu Lys Gly Val Asn Val Lys Tyr Glu
145                 150                 155                 160

Thr Arg Asn Asn Arg Asn Gly Tyr Lys Ala Gly Ala Leu Arg Asp Gly
                165                 170                 175

Leu Lys Lys Pro Tyr Val Glu Asp Cys Glu Phe Val Val Ile Phe Asp
            180                 185                 190

Ala Asp Phe Gln Pro Glu Glu Asp Phe Leu Trp Arg Thr Val Pro Tyr
        195                 200                 205

Leu Leu Glu Asn Pro Glu Leu Ala Leu Val Gln Ala Arg Trp Lys Phe
    210                 215                 220
```

```
Val Asn Ala Asn Glu Cys Leu Met Thr Arg Leu Gln Glu Met Ser Leu
225                 230                 235                 240

Asp Tyr His Phe Ser Val Glu Gln Glu Val Gly Ser Ser Thr Cys Ser
                245                 250                 255

Phe Phe Gly Phe Asn Gly Thr Ala Gly Val Trp Arg Ile Gln Ala Val
            260                 265                 270

Ser Asp Ala Gly Gly Trp Lys Asp Arg Thr Thr Val Glu Asp Met Asp
        275                 280                 285

Leu Ala Val Arg Ala Ser Leu Lys Gly Trp Lys Phe Ile Phe Val Gly
    290                 295                 300

Asp Leu Ser Val Lys Asn Glu Leu Pro Ser Thr Phe Lys Ala Tyr Arg
305                 310                 315                 320

Phe Gln Gln His Arg Trp Ser Cys Gly Pro Ala Asn Leu Phe Arg Lys
                325                 330                 335

Met Phe Lys Glu Ile Leu Leu Cys Glu Arg Val Ser Ile Trp Lys Lys
            340                 345                 350

Phe His Val Ile Tyr Ala Phe Phe Val Arg Lys Ile Val Ala His
        355                 360                 365

Trp Val Thr Phe Phe Phe Tyr Cys Ile Val Ile Pro Ala Thr Ile Leu
    370                 375                 380

Val Pro Glu Val His Leu Pro Lys Pro Ile Ala Val Tyr Pro Pro Ala
385                 390                 395                 400

Thr Ile Thr Leu Leu Asn Ala Ala Ser Thr Pro Arg Ser Leu His Leu
                405                 410                 415

Leu Val Phe Trp Ile Leu Phe Glu Asn Val Met Ser Leu His Arg Ser
            420                 425                 430

Lys Ala Ala Ile Ile Gly Leu Leu Glu Ala Ser Arg Val Asn Glu Trp
        435                 440                 445

Ile Val Thr Glu Lys Leu Gly Asn Ala Leu Lys Gln Lys Tyr Ser Ile
    450                 455                 460

Pro Lys Val Ser Lys Arg Pro Gly Ser Arg Ile Ala Glu Arg Ile His
465                 470                 475                 480

Phe Leu Glu Leu Ile Met Gly Met Tyr Met Leu His Cys Ala Phe Tyr
                485                 490                 495

Asn Leu Ile Phe Ala Asn Asp His Phe Phe Ile Tyr Pro Leu Leu Gln
            500                 505                 510

Ala Gly Ala Phe Phe Ile Ile Gly Leu Gly Tyr Ile Gly Thr Ile Val
        515                 520                 525

Pro Thr
    530

<210> SEQ ID NO 6
<211> LENGTH: 530
<212> TYPE: PRT
<213> ORGANISM: Coffea arabica

<400> SEQUENCE: 6

Met Arg Asn Ser Val Phe Leu Glu Pro Glu Pro Glu Val Asn Leu Tyr
1               5                   10                  15

Asp Asp Thr Gly Arg Ser Leu Ser Gln Ala Trp Asp Arg Ile Arg Val
                20                  25                  30

Pro Ile Ile Val Pro Ile Leu Arg Phe Ala Leu Tyr Val Cys Ile Ala
            35                  40                  45

Met Ser Val Met Leu Phe Ile Glu Arg Val Tyr Met Ala Ile Val Ile
    50                  55                  60
```

-continued

```
Gly Cys Val Lys Cys Leu Gly Arg Lys Arg Tyr Thr Lys Tyr Asn Leu
 65                  70                  75                  80

Asp Ala Ile Lys Glu Asp Leu Glu Gln Asn Arg Asn Tyr Pro Met Val
                 85                  90                  95

Leu Val Gln Ile Pro Met Phe Asn Glu Lys Glu Val Tyr Lys Leu Ser
            100                 105                 110

Ile Gly Ala Ala Cys Gly Leu Ser Arg Pro Ser Asp Arg Leu Ile Val
        115                 120                 125

Gln Val Leu Asp Asp Ser Thr Asn Glu Val Leu Arg Ala Leu Val Glu
    130                 135                 140

Leu Glu Cys Gln Arg Trp Ile Glu Lys Gly Val Asn Val Lys Tyr Glu
145                 150                 155                 160

Thr Arg Asn Asn Arg Asn Gly Tyr Lys Ala Gly Ala Leu Arg Asp Gly
                165                 170                 175

Leu Lys Lys Pro Tyr Val Glu Asp Cys Glu Phe Val Val Ile Phe Asp
            180                 185                 190

Ala Asp Phe Gln Pro Glu Glu Asp Phe Leu Trp Arg Thr Val Pro Tyr
        195                 200                 205

Leu Leu Glu Asn Pro Glu Leu Ala Leu Val Gln Ala Arg Trp Lys Phe
    210                 215                 220

Val Asn Ala Asn Glu Cys Leu Met Thr Arg Leu Gln Glu Met Ser Leu
225                 230                 235                 240

Asp Tyr His Phe Ser Val Gln Glu Val Gly Ser Ser Thr Cys Ser
                245                 250                 255

Phe Phe Gly Phe Asn Gly Thr Ala Gly Val Trp Arg Ile Gln Ala Val
            260                 265                 270

Ser Asp Ala Gly Gly Trp Lys Asp Arg Thr Thr Val Glu Asp Met Asp
        275                 280                 285

Leu Ala Val Arg Ala Ser Leu Lys Gly Trp Lys Phe Ile Phe Val Gly
    290                 295                 300

Asp Leu Ser Val Lys Asn Glu Leu Pro Ser Thr Phe Lys Ala Tyr Arg
305                 310                 315                 320

Phe Gln Gln His Arg Trp Ser Cys Gly Pro Ala Asn Leu Phe Arg Lys
                325                 330                 335

Met Phe Lys Glu Ile Leu Leu Cys Glu Arg Val Ser Ile Trp Lys Lys
            340                 345                 350

Phe His Val Ile Tyr Ala Phe Phe Phe Val Arg Lys Ile Val Ala His
        355                 360                 365

Trp Val Thr Phe Phe Tyr Cys Ile Val Ile Pro Ala Thr Ile Leu
    370                 375                 380

Val Pro Glu Val His Leu Pro Lys Pro Ile Ala Val Tyr Pro Pro Ala
385                 390                 395                 400

Thr Ile Thr Leu Leu Asn Ala Ala Ser Thr Pro Arg Ser Leu His Leu
                405                 410                 415

Leu Val Phe Trp Ile Leu Phe Glu Asn Val Met Ser Leu His Arg Ser
            420                 425                 430

Lys Ala Ala Ile Ile Gly Leu Leu Glu Ala Ser Arg Val Asn Glu Trp
        435                 440                 445

Ile Val Thr Glu Lys Leu Gly Asn Ala Leu Lys Gln Lys Tyr Ser Ile
    450                 455                 460

Pro Lys Val Ser Lys Arg Pro Gly Ser Arg Ile Ala Glu Arg Ile His
465                 470                 475                 480

Phe Leu Glu Leu Ile Met Gly Met Tyr Met Leu His Cys Ala Phe Tyr
                485                 490                 495
```

```
Asn Leu Ile Phe Ala Asn Asp His Phe Phe Ile Tyr Pro Leu Leu Gln
            500                 505                 510
Ala Gly Ala Phe Phe Ile Ile Gly Leu Gly Tyr Ile Gly Thr Ile Val
            515                 520                 525
Pro Thr
    530

<210> SEQ ID NO 7
<211> LENGTH: 1779
<212> TYPE: DNA
<213> ORGANISM: Coffea canephora

<400> SEQUENCE: 7
acattacttc agtgtactag tccaagtaag acatatacca ttaatgtcat ctagtaaaga      60
ccaaatacgc tgctacctca agaattcaga atcagcact agacctaagt tattgttgct     120
attcaagaaa agcaaggtag acatacaagg aaataatcca ctatctctgt tgttcaggtc    180
tataaactct caattggagc tgcatgtggg cttcatggc catcagatag attaatagtt     240
caggttcttg atgactccac gaatgaagtc ctgcgggcat ggtggagtt ggagtgtcaa     300
agatggatag agaaaggggt gaatgtgaag tatgaaacaa ggaacaacag gaatggttat    360
aaagcaggtg cacttcggga tggtctaaaa aagccatatg ttgaagattg tgagtttgtc    420
gtcattttg atgcagactt ccagcctgag gaggactttc tgtggagaac agtgccttat     480
cttcttgaaa acccgagct ggctttggtt caagcccgat ggaaatttgt aaatgcaaat     540
gaatgtttaa tgacgcggct tcaggagatg tcactagact atcacttcag tgtggagcaa    600
gaagtaggct cgtcaacatg ttcattcttt gggtttaatg gtaacttcat agacattct      660
gctacatgtt aattagtttg ctatagcaac ttccatgaag acactttcag ccaatatcat    720
caacactttt cgcttgcatc aaaggaactg ccggtgtatg gaggatccaa gcagtaagtg    780
atgctggtgg atggaaagat aggaccacgg ttgaggatat ggaccttgca gtaagggcta    840
gccttaaggg ttgaaattc atctttgtgg agatttatc tgtcaaaaat gaacttccaa      900
gcactttcaa ggcttataga tttcagcagc atcgatggtc gtgtggccca gccaatctct    960
tcagaaaaat gttcaaagaa attctccttt gtgagcgtgt gtccatctgg aagaaattcc   1020
atgtcatcta tgccttcttc tttgtgagga agatagttgc acactgggtt actttttct    1080
tctactgcat tgtgatccca gcaactatct tagttcctga agtgcatctt ccaaagccaa   1140
tagcagttta tctgccagca accattacac ttcttaatgc agctagcact ccaaggtcct   1200
tgcatctact cgtgttctgg atactgtttg agaatgtcat gtccctccat cgatccaaag   1260
cagcaattat aggactttta gaagccagcc gagttaacga gtggattgtg acggaaaagc   1320
ttggaaacgc attgaagcaa agtacagca tccccaaagt atctaagaga ccaagatcac    1380
gaattgcaga aaggatccac tttttggagc tgataatggg aatgtatatg ctgcactgtg   1440
ctttctacaa catgatcttt gcaaacgatc atttcttcat atacctgtta cttcaagcag   1500
gggcttctt cacaataggg cttggttaca ttggaacaat tgtccctact taagaagcta   1560
ggcataccga aaataaagcc tccaaaagga caagcaggct gctggaagct actgtcattt   1620
ggtatatcca tctagtagca tactactaag tcatggtatt attttcaat gttctttata   1680
ctgtgtgtcc tcaagggtct ctgcacttcg ggccccctt aatatagacg agtacagcaa   1740
gtcaacttgg ttcttgaata aaaaaaaaa aaaaaaaa                            1779

<210> SEQ ID NO 8
```

<211> LENGTH: 1349
<212> TYPE: DNA
<213> ORGANISM: Coffea canephora

<400> SEQUENCE: 8

| | |
|---|---|
| ataaagcagg tgcacttcgg gatggtctaa aaaagccata tgttgaagat tgtgagtttg | 60 |
| tcgtcatttt tgatgcagac ttccagcctg aggaggactt tctgtggaga acagtgcctt | 120 |
| atcttcttga aacccagag ctggcttttgg ttcaagcccg atggaaattt gtaaatgcaa | 180 |
| atgaatgttt aatgacgcgg cttcaggaga tgtcactaga ctatcacttc agtgtggagc | 240 |
| aagaagtagg ctcgtcaaca tgttcattct ttgggtttaa tggaactgcc ggtgtatgga | 300 |
| ggatccaagc agtaagtgat gctggtggat ggaaagatag gaccacggtt gaggatatgg | 360 |
| accttgcagt aagggctagc cttaagggtt ggaaattcat ctttgtggga gatttatctg | 420 |
| tcaaaaatga acttccaagc actttcaagg cttatagatt tcagcagcat cgatggtcgt | 480 |
| gtggcccagc caatctcttc agaaaaatgt tcaaagaaat tctcctttgt gagcgtgtgt | 540 |
| ccatctggaa gaaattccat gtcatctatg ccttcttctt tgtgaggaag atagttgcac | 600 |
| actgggttac tttttttcttc tactgcattg tgatcccagc aactatctta gttcctgaag | 660 |
| tgcatcttcc aaagccaata gcagtttatc tgccagcaac cattacactt cttaatgcag | 720 |
| ctagcactcc aaggtccttg catctactcg tgttctggat actgtttgag aatgtcatgt | 780 |
| ccctccatcg atccaaagca gcaattatag acttttaga agccagccga gttaacgagt | 840 |
| ggattgtgac ggaaaagctt ggaaacgcat tgaagcaaaa gtacagcatc cccaaagtat | 900 |
| ctaagagacc aagatcacga attgcagaaa ggatccactt tttggagctg ataatgggaa | 960 |
| tgtatatgct gcactgtgct ttctacaaca tgatctttgc aaacgatcat ttcttcatat | 1020 |
| acctgttact tcaagcaggg gctttcttca caatagggct tggttacatt ggaacaattg | 1080 |
| tccctactta agaagctagg cataccgaaa ataaagcctc caaaggaca agcaggctgc | 1140 |
| tggaagctac tgtcatttgg tatatccatc tagtagcata ctactaagtc atggtattat | 1200 |
| ttttcaatgt tctttatact gtgtgtcctc aagggtctct gcacttcggg cccccttaa | 1260 |
| tatagacgag tacagcaagt caacttggtt cttgaataaa aatgtaattc actggtaccc | 1320 |
| atgttttaaa aaaaaaaaa aaaaaaaaa | 1349 |

<210> SEQ ID NO 9
<211> LENGTH: 259
<212> TYPE: DNA
<213> ORGANISM: Coffea canephora

<400> SEQUENCE: 9

| | |
|---|---|
| ttgaacgggt gtacatggcg attgtgattg gatgtgtcaa gtgcttggga aggaaacgat | 60 |
| ataccaagta taatcttgat gccataaaag aagacctaga gcaaaacaga aactatccta | 120 |
| tggtgctggg ccaaatacccc atgtttaacg aaaaagaggc ctataaactc tcaattggag | 180 |
| ctgcatgtgg gctttcatgg ccatcagata gattaatagt tcaggttctt gatgactcca | 240 |
| cgaatgaagt cctgcgggc | 259 |

<210> SEQ ID NO 10
<211> LENGTH: 340
<212> TYPE: DNA
<213> ORGANISM: Coffea canephora

<400> SEQUENCE: 10

| | |
|---|---|
| cagatgcaga tgaactctct gtgtctgctc attgccctca gctcctaagg gctctatcat | 60 |

```
tttggcttca agttcaagtt cttcttcacc ctcaaaaaag catttcgttg cttcacttcc    120
acaatcatag cctgataaaa tgagaaactc agttttcta gagcccgagc cagaggtaaa     180
tttatatgat gatactggca gaagtctcag ccaagcatgg gaccgtatac gagttcctat    240
aattgtgcca attctgcggc ttgctttata tgtatgcata gcaatgtctg ttatgctttt    300
cattgaacgg gtgtacatgg cgatgtgatt ggatgtgtca                          340

<210> SEQ ID NO 11
<211> LENGTH: 689
<212> TYPE: DNA
<213> ORGANISM: Coffea canephora

<400> SEQUENCE: 11
atattatttt gagggtact ggatggaaat cgtggggacg ctggagaaca tcaccgacgc      60
gtacacgggg atcgagaagc gggagaggag attgaggagg aggcatgcag agagagtggg    120
ggagagttat ggtaaggtgt gggaggagca ccttaaggac gctgggtatg ggaggggggag   180 ttggaggaga ccgttcatga ctcacttcac ggggtgtcag ccttgtagcg gggaccacaa    240
ccagatgtac tctgggcagt cttgctggga tgcgatgcaa attgctctga attttgcaga    300
taatcaggtg cttaggagat atgggttcgt gcaccgggat ctattggata cgtccaccgt    360
cttgcctctg ccgttcgatt acccggcatc ggaccttgtt gaaggcgctt cctagacata    420
ttttattcta accaacagtt tcctagtttt gtaccatcat cggaggcttt acgagtagta    480
tcattttttt ttttaatctc tgaaacgatt agtatcatat agaaagaagg tatatcagat    540
ttatgaaact atactactgt tgctttagta gtatcatttt gacggttatg ggctcttagt    600
agtaagtgat tgcatatata tatatttcgt ttttcatttt ttgggcaccc tggagatgta    660
ttttctctgt tgtaagttaa agttggggg                                      689

<210> SEQ ID NO 12
<211> LENGTH: 859
<212> TYPE: DNA
<213> ORGANISM: Coffea canephora

<400> SEQUENCE: 12
ctctctcctc gtaaaaaaaa caagaagcaa cagtaaagcc ggccagccat ctctaaagat     60
aaagctcaga ccaaacaatc atcatatatt tccagagata gcagcaggtc gtacttcctc    120
gctgtatttg tctccatggt actcgtcttt gtcatatgtt ccttgacaga aactttgccc    180
agtttccaaa ataggatttc aactaccggt gctgatacct gtaacggcga accaccagcc    240
gtaaatcgaa cccacgaccc taagaagcc acttttacg acgaacccga gctaacctac      300
acgctaggca aaaccatcaa agactgggac aagaagagaa agtcctggct aaaccttcat    360
ccctcgttcg ccgcgggtgc cgacacacgt attctcatcg tgacggggtc tcagccttcg    420
ccatgcaaga atcccatcgg ggatcatcta ctcctgaggt gtttcaagaa caaggctgat    480
tattccagaa tccacggcta cgatatcttt tacaacaccg catgtttaga ccccaagctg    540
tgcaacgttt gggctaaggt agcttttaatt cgggctgcca tggtggccca cccggaagca    600
gagtggatct ggtggatgga ctccgatgct gtctttactg acatgtactt taaagttccg    660
ttacagaggt acaagcagca taatctggtt gttcccggct ggcccgacat ggtttacgag    720
aagaagagtt gggtttctct aaataccggg agtttcttca cgagaaattg tcagtggtct    780
ttggattttt tggatgcctg ggctcgtatg agccccgaa gccctgatta caagttctgg     840
agtgaaactt taatgtcta                                                 859
```

<210> SEQ ID NO 13
<211> LENGTH: 1626
<212> TYPE: DNA
<213> ORGANISM: Coffea arabica

<400> SEQUENCE: 13

| | | | | | |
|---|---|---|---|---|---|
| agacagcagc | caccatgcct | aagcacaaca | gcctcctccg | caccaaaacc | tcgtcgtttt | 60 |
| tctccagctg | ctttctttac | gccgccggaa | cttccgcttc | cttttttgtta | gcctgggcct | 120 |
| tctggtcctt | cttcagtagc | cccgccccat | ctgcgaatcc | ctctttctcg | aggggcctag | 180 |
| cttccgaggc | tgccctcagc | tgccccgccg | ggaaagcggg | tcacaaccgg | agctacgatc | 240 |
| cgcccgaccc | gactttctat | gacgacccgg | aattgagcta | caccattgag | aagaccatca | 300 |
| agaactggga | tgagaagagg | cgggagtggc | tcgagaagca | tccctcgttc | gccgccggag | 360 |
| cagctgacag | gattttaatg | gtcacgggtt | ctcaggcgac | gccctgcaag | aacccgatcg | 420 |
| gggatcactt | gctgttgagg | ttcttcaaga | taaggcgga | ctactgcagg | atccacggct | 480 |
| acgatatctt | ctacaacacc | gtgctgctgc | agccgaagat | gttctcgttt | tgggcaaaaa | 540 |
| tgcctgccgt | gaaagcggtc | atgttggccc | atccggaggc | ggagtggatc | tggtgggtag | 600 |
| attcagacac | agccttcacc | gacatggact | tcacgctgcc | gctggatcgc | tacaaggccc | 660 |
| ataatttagt | ggtccacggc | tggcctcact | tgattcacag | ggagaagagc | tggacggggc | 720 |
| tgaacgcggg | agtgtttctg | atgcgcaact | gtcagtggtc | aatggatttc | atggaagaat | 780 |
| gggcgagcat | ggggcctcaa | gccccggagt | acgacaaatg | gggcgtgatt | cagcggacga | 840 |
| cgttcaagga | caagacgttt | ccggagtcag | acgatcagac | ggggttggct | tatctgatcc | 900 |
| tgaaagagag | agaaaatgg | gggaacaaaa | tttacatgga | ggatgaatat | tattttgagg | 960 |
| ggtactggat | ggaaatcgtg | gggacgctgg | agaacatcac | cgacgcgtac | acggggatcg | 1020 |
| agaagcggga | gaggaggttg | aggaggaggc | atgcagagag | agtgggggag | agttatggta | 1080 |
| aggtgtggga | ggagcacctt | aaggacgctg | ggtatgggag | ggggagttgg | aggagaccgt | 1140 |
| tcatgactca | cttcacgggg | tgtcagcctt | gtagcgggga | ccacaaccag | atgtactctg | 1200 |
| gacagtcttg | ctgggatgcg | atgcaaattg | ctctgaattt | tgcagataat | caggtgctta | 1260 |
| ggagatatgg | gttcgtgcac | cgggatttat | tggatacgtc | caccgtcccg | cctctgccgt | 1320 |
| tcgattaccc | agcatcggac | cttgttggag | gcgcttccta | gaaatatttt | attctaacca | 1380 |
| actgttaagt | agttttgtac | catcatcgga | ggctttacta | gtagtatcat | tattgattta | 1440 |
| tgaaacggtt | agtatcatat | agaaagaagg | tatatcatat | ttatgaaact | atactactgt | 1500 |
| tacttaacta | gtatcatttt | gaaggttatg | ggctcttaat | agtaagtgat | tgcatatgta | 1560 |
| tttcgttttt | cattttttg | ggcaccctgg | agatgtattt | tctctgttgt | aagttaaaag | 1620 |
| tcgggg | | | | | | 1626 |

<210> SEQ ID NO 14
<211> LENGTH: 1695
<212> TYPE: DNA
<213> ORGANISM: Coffea canephora

<400> SEQUENCE: 14

| | | | | | |
|---|---|---|---|---|---|
| ctctctcttt | ggcaaaaaaa | caagaagcaa | cagtaaagcc | ggccagccat | gtctagagct | 60 |
| aaagctcaga | ccaaacaatc | atcatatatt | tccagagata | gcagcaggtc | gtacttcctc | 120 |
| gctgtatttg | tctccatggt | actcgtcttt | gtcatatgtt | ccttgacaga | aactttgccc | 180 |
| agtttccaaa | ataggatttc | aactaccggt | gctgatacct | gtaacggcga | accaccagcc | 240 |

```
gtaaatcgaa cccacgaccc taaagaagcc acttttacg acgaacccga gctaacctac      300
acgctaggca aaaccatcaa agactgggac aagaagagaa agtcctggct aaaccttcat     360
ccctcgttcg ccgcgggtgc cgacacacgt attctcatcg tgacggggtc tcagccttcg     420
ccatgcaaga atcccatcgg ggatcatcta ctcctgaggt gtttcaagaa caaggctgat     480
tattccagaa tccacggcta cgatatcttt tacaacaccg catgtttaga ccccaagctg     540
tgcaacgttt gggctaaggt agctttaatt cgggctgcca tggtggccca cccggaagca     600
gagtggatct ggtggatgga ctccgatgct gtctttactg acatgtactt aaagttccg      660 ttacagaggt acaagcagca taatctggtt gttcccggct ggcccgacat ggtttacgag     720
aagaagagtt gggtttctct aaataccggg agtttcttca cgagaaattg tcagtggtct     780
ttggattttt tggatgcctg ggctcgtatg agccccgaa gccctgatta caagttctgg      840
agtgaaactt taatgtctac gctttcggat aagatgttcc cgggagcaga tgagcagtcg     900
tctttggttt atttgctgtt gacagaaaag aagaaatggg gggataagat ttatttagag     960
aatcagtacg acttgagctc ttattgggta ggcgtagttg gaaagcttga taaatttacg    1020
aggacggagg ctgacgcaga gaagaatttg cccttgctaa ggaggagaag ggcggaggtg    1080
gtgggcgaga gcgttggtga ggtgtgggag aagtacttgg aaaataatac cgctagcgag    1140
ggtaaacggc cgtttattac gcatttcacg ggatgccagc cctgcagcgg aaaccatgac    1200
ccctcctacg ttggaaatac ctgctgggat gcaatggaga ggactctgaa ttatgctgat    1260
aatcaggtcc ttcgtaactt gggttttgtg cacagggata taagccgtgg ctcttacgtt    1320
ttacccctag cctttgattt tccatcggaa gtgctgcaaa gaaagaaatc cggtgaagaa    1380
tataacaggt gaataaatcc ctccgtttta gtgctgttta tagattatag cagccagcag    1440
gacttgggcc ctgaaaattc agtatctcag aaaaaaaatg acagtgaaat tgagagagca    1500
aaaatgtttt cacaagcttg tcgtggtaaa ttcctcagta attgagtgaa tttcaagata    1560
cttatatttg ttgccacgaa atttgttgat gcttttcct gttggtcaac aaaatcgaat      1620
tgattgagtg tgctttttaa taaaaaaaaa aaaaaaaaaa aaaaaaaaaa aaaaaaaaa      1680 aaaaaaaaaa aaaaa                                                      1695
```

<210> SEQ ID NO 15
<211> LENGTH: 137
<212> TYPE: PRT
<213> ORGANISM: Coffea canephora

<400> SEQUENCE: 15

```
Tyr Tyr Phe Glu Gly Tyr Trp Met Glu Ile Val Gly Thr Leu Glu Asn
1               5                   10                  15

Ile Thr Asp Ala Tyr Thr Gly Ile Glu Lys Arg Glu Arg Arg Leu Arg
            20                  25                  30

Arg Arg His Ala Glu Arg Val Gly Glu Ser Tyr Gly Lys Val Trp Glu
        35                  40                  45

Glu His Leu Lys Asp Ala Gly Tyr Gly Arg Gly Ser Trp Arg Arg Pro
    50                  55                  60

Phe Met Thr His Phe Thr Gly Cys Gln Pro Cys Ser Gly Asp His Asn
65                  70                  75                  80

Gln Met Tyr Ser Gly Gln Ser Cys Trp Asp Ala Met Gln Ile Ala Leu
                85                  90                  95

Asn Phe Ala Asp Asn Gln Val Leu Arg Arg Tyr Gly Phe Val His Arg
            100                 105                 110

Asp Leu Leu Asp Thr Ser Thr Val Leu Pro Leu Pro Phe Asp Tyr Pro
```

```
                115                 120                 125

Ala Ser Asp Leu Val Glu Gly Ala Ser
        130                 135
```

<210> SEQ ID NO 16
<211> LENGTH: 196
<212> TYPE: PRT
<213> ORGANISM: Coffea canephora

<400> SEQUENCE: 16

```
Thr Phe Tyr Asp Glu Pro Glu Leu Thr Tyr Thr Leu Gly Lys Thr Ile
1               5                   10                  15

Lys Asp Trp Asp Lys Lys Arg Lys Ser Trp Leu Asn Leu His Pro Ser
            20                  25                  30

Phe Ala Ala Gly Ala Asp Thr Arg Ile Leu Ile Val Thr Gly Ser Gln
        35                  40                  45

Pro Ser Pro Cys Lys Asn Pro Ile Gly Asp His Leu Leu Leu Arg Cys
    50                  55                  60

Phe Lys Asn Lys Ala Asp Tyr Ser Arg Ile His Gly Tyr Asp Ile Phe
65                  70                  75                  80

Tyr Asn Thr Ala Cys Leu Asp Pro Lys Leu Cys Asn Val Trp Ala Lys
                85                  90                  95

Val Ala Leu Ile Arg Ala Ala Met Val Ala His Pro Glu Ala Glu Trp
            100                 105                 110

Ile Trp Trp Met Asp Ser Asp Ala Val Phe Thr Asp Met Tyr Phe Lys
        115                 120                 125

Val Pro Leu Gln Arg Tyr Lys Gln His Asn Leu Val Val Pro Gly Trp
    130                 135                 140

Pro Asp Met Val Tyr Glu Lys Lys Ser Trp Val Ser Leu Asn Thr Gly
145                 150                 155                 160

Ser Phe Phe Thr Arg Asn Cys Gln Trp Ser Leu Asp Phe Leu Asp Ala
                165                 170                 175

Trp Ala Arg Met Ser Pro Arg Ser Pro Asp Tyr Lys Phe Trp Ser Glu
            180                 185                 190

Thr Leu Met Ser
        195
```

<210> SEQ ID NO 17
<211> LENGTH: 448
<212> TYPE: PRT
<213> ORGANISM: Coffea arabica

<400> SEQUENCE: 17

```
Met Pro Lys His Asn Ser Leu Leu Arg Thr Lys Thr Ser Ser Phe Phe
1               5                   10                  15

Ser Ser Cys Phe Leu Tyr Ala Ala Gly Thr Ser Ala Ser Phe Leu Leu
            20                  25                  30

Ala Trp Ala Phe Trp Ser Phe Phe Ser Ser Pro Ala Pro Ser Ala Asn
        35                  40                  45

Pro Ser Phe Ser Arg Gly Leu Ala Ser Glu Ala Ala Leu Ser Cys Pro
    50                  55                  60

Ala Gly Lys Ala Gly His Asn Arg Ser Tyr Asp Pro Pro Asp Pro Thr
65                  70                  75                  80

Phe Tyr Asp Asp Pro Glu Leu Ser Tyr Thr Ile Glu Lys Thr Ile Lys
                85                  90                  95

Asn Trp Asp Glu Lys Arg Arg Glu Trp Leu Glu Lys His Pro Ser Phe
            100                 105                 110
```

```
Ala Ala Gly Ala Ala Asp Arg Ile Leu Met Val Thr Gly Ser Gln Ala
            115                 120                 125

Thr Pro Cys Lys Asn Pro Ile Gly Asp His Leu Leu Leu Arg Phe Phe
130                 135                 140

Lys Asn Lys Ala Asp Tyr Cys Arg Ile His Gly Tyr Asp Ile Phe Tyr
145                 150                 155                 160

Asn Thr Val Leu Leu Gln Pro Lys Met Phe Ser Phe Trp Ala Lys Met
                165                 170                 175

Pro Ala Val Lys Ala Val Met Leu Ala His Pro Glu Ala Glu Trp Ile
            180                 185                 190

Trp Trp Val Asp Ser Asp Thr Ala Phe Thr Asp Met Asp Phe Thr Leu
        195                 200                 205

Pro Leu Asp Arg Tyr Lys Ala His Asn Leu Val Val His Gly Trp Pro
210                 215                 220

His Leu Ile His Arg Glu Lys Ser Trp Thr Gly Leu Asn Ala Gly Val
225                 230                 235                 240

Phe Leu Met Arg Asn Cys Gln Trp Ser Met Asp Phe Met Glu Glu Trp
                245                 250                 255

Ala Ser Met Gly Pro Gln Ala Pro Glu Tyr Asp Lys Trp Gly Val Ile
            260                 265                 270

Gln Arg Thr Thr Phe Lys Asp Lys Thr Phe Pro Glu Ser Asp Asp Gln
        275                 280                 285

Thr Gly Leu Ala Tyr Leu Ile Leu Lys Glu Arg Glu Lys Trp Gly Asn
290                 295                 300

Lys Ile Tyr Met Glu Asp Glu Tyr Tyr Phe Glu Gly Tyr Trp Met Glu
305                 310                 315                 320

Ile Val Gly Thr Leu Glu Asn Ile Thr Asp Ala Tyr Thr Gly Ile Glu
                325                 330                 335

Lys Arg Glu Arg Arg Leu Arg Arg Arg His Ala Glu Arg Val Gly Glu
            340                 345                 350

Ser Tyr Gly Lys Val Trp Glu Glu His Leu Lys Asp Ala Gly Tyr Gly
        355                 360                 365

Arg Gly Ser Trp Arg Arg Pro Phe Met Thr His Phe Thr Gly Cys Gln
370                 375                 380

Pro Cys Ser Gly Asp His Asn Gln Met Tyr Ser Gly Gln Ser Cys Trp
385                 390                 395                 400

Asp Ala Met Gln Ile Ala Leu Asn Phe Ala Asp Asn Gln Val Leu Arg
                405                 410                 415

Arg Tyr Gly Phe Val His Arg Asp Leu Leu Asp Thr Ser Thr Val Pro
            420                 425                 430

Pro Leu Pro Phe Asp Tyr Pro Ala Ser Asp Leu Val Gly Gly Ala Ser
        435                 440                 445

<210> SEQ ID NO 18
<211> LENGTH: 447
<212> TYPE: PRT
<213> ORGANISM: Coffea canephora

<400> SEQUENCE: 18

Met Ser Arg Ala Lys Ala Gln Thr Lys Gln Ser Ser Tyr Ile Ser Arg
1               5                   10                  15

Asp Ser Ser Arg Ser Tyr Phe Leu Ala Val Phe Val Ser Met Val Leu
            20                  25                  30

Val Phe Val Ile Cys Ser Leu Thr Glu Thr Leu Pro Ser Phe Gln Asn
        35                  40                  45
```

```
Arg Ile Ser Thr Thr Gly Ala Asp Thr Cys Asn Gly Glu Pro Pro Ala
 50                  55                  60

Val Asn Arg Thr His Asp Pro Lys Glu Ala Thr Phe Tyr Asp Glu Pro
 65                  70                  75                  80

Glu Leu Thr Tyr Thr Leu Gly Lys Thr Ile Lys Asp Trp Asp Lys Lys
                 85                  90                  95

Arg Lys Ser Trp Leu Asn Leu His Pro Ser Phe Ala Ala Gly Ala Asp
                100                 105                 110

Thr Arg Ile Leu Ile Val Thr Gly Ser Gln Pro Ser Pro Cys Lys Asn
                115                 120                 125

Pro Ile Gly Asp His Leu Leu Leu Arg Cys Phe Lys Asn Lys Ala Asp
        130                 135                 140

Tyr Ser Arg Ile His Gly Tyr Asp Ile Phe Tyr Asn Thr Ala Cys Leu
145                 150                 155                 160

Asp Pro Lys Leu Cys Asn Val Trp Ala Lys Val Ala Leu Ile Arg Ala
                165                 170                 175

Ala Met Val Ala His Pro Glu Ala Glu Trp Ile Trp Trp Met Asp Ser
                180                 185                 190

Asp Ala Val Phe Thr Asp Met Tyr Phe Lys Val Pro Leu Gln Arg Tyr
        195                 200                 205

Lys Gln His Asn Leu Val Val Pro Gly Trp Pro Asp Met Val Tyr Glu
210                 215                 220

Lys Lys Ser Trp Val Ser Leu Asn Thr Gly Ser Phe Phe Thr Arg Asn
225                 230                 235                 240

Cys Gln Trp Ser Leu Asp Phe Leu Asp Ala Trp Ala Arg Met Ser Pro
                245                 250                 255

Arg Ser Pro Asp Tyr Lys Phe Trp Ser Glu Thr Leu Met Ser Thr Leu
                260                 265                 270

Ser Asp Lys Met Phe Pro Gly Ala Asp Glu Gln Ser Ser Leu Val Tyr
        275                 280                 285

Leu Leu Leu Thr Glu Lys Lys Trp Gly Asp Lys Ile Tyr Leu Glu
290                 295                 300

Asn Gln Tyr Asp Leu Ser Ser Tyr Trp Val Gly Val Gly Lys Leu
305                 310                 315                 320

Asp Lys Phe Thr Arg Thr Glu Asp Ala Glu Lys Asn Leu Pro Leu
                325                 330                 335

Leu Arg Arg Arg Arg Ala Glu Val Val Gly Glu Ser Val Gly Glu Val
                340                 345                 350

Trp Glu Lys Tyr Leu Glu Asn Asn Thr Ala Ser Glu Gly Lys Arg Pro
                355                 360                 365

Phe Ile Thr His Phe Thr Gly Cys Gln Pro Cys Ser Gly Asn His Asp
        370                 375                 380

Pro Ser Tyr Val Gly Asn Thr Cys Trp Asp Ala Met Glu Arg Thr Leu
385                 390                 395                 400

Asn Tyr Ala Asp Asn Gln Val Leu Arg Asn Leu Gly Phe Val His Arg
                405                 410                 415

Asp Ile Ser Arg Gly Ser Tyr Val Leu Pro Leu Ala Phe Asp Phe Pro
                420                 425                 430

Ser Glu Val Leu Gln Arg Lys Lys Ser Gly Glu Glu Tyr Asn Arg
        435                 440                 445

<210> SEQ ID NO 19
<211> LENGTH: 801
<212> TYPE: DNA
```

<213> ORGANISM: Coffea canephora

<400> SEQUENCE: 19

| | | |
|---|---|---|
| attttgaggg gtactggatg gaaatcgtgg ggacgctgga gaacatcacc gacgcgtaca | 60 |
| cggggatcga gaagcgggag aggagattga ggaggaggca tgcagagaga gtggggggaga | 120 |
| gttatggtaa ggtgtgggag gagcaccetta aggacgctgg gtatgggagg gggagttgga | 180 |
| ggagaccgtt catgactcac ttcacggggt gtcagccttg tagcggggac cacaaccaga | 240 |
| tgtactctgg gcagtcttgc tgggatgcga tgcaaattgc tctgaatttt gcagataatc | 300 |
| aggtgcttag gagatatggg ttcgtgcacc gggatctatt ggatacgtcc accgtcttgc | 360 |
| ctctgccgtt cgattacccg gcatcggacc ttgttgaagg cgcttcctag acatatttta | 420 |
| ttctaaccaa cagtttccta gttttgtacc atcatcggag gctttacgag tagtatcatt | 480 |
| tttttttttt ttttaatttc tgaaacgatt agtatcatat agaaagaagg tatatcagat | 540 |
| ttatgaaact atactactgt tactttacta gtatcatttt gacggttatg ggctcttttgt | 600 |
| agtgagtgat tgcatatata cttcgttttt cattttttttg ggcaccctgg agatgtattt | 660 |
| tctctgttgt aagttaaaag tcgggggtct tataaagtgt taatgcatgt actatatatg | 720 |
| ttgtacttgt ttttttttaa aaaaaaatt ctttttttgtt gggggtttaa aaaaaaaaa | 780 |
| aaaaaaaaaa aaaaaaaaaa a | 801 |

<210> SEQ ID NO 20
<211> LENGTH: 1120
<212> TYPE: DNA
<213> ORGANISM: Coffea canephora

<400> SEQUENCE: 20

| | | |
|---|---|---|
| agacagcagc caccatgcct aagcacaaca gcctcctccg caccaaaacc tcgtcgtttt | 60 |
| tctccagctg cttctttac gccgccggaa cttccgcttc cttttttgtta gcctgggcct | 120 |
| tctggtcctt cttcagtagc cccgcccccat ctgcgaatcc ctcttttctcg aggggcctag | 180 |
| cttccgaggc tgccctcagc tgccccgccg ggaaagcggg tcacaaccgg agctacgatc | 240 |
| cgcccgaccc gactttctat gacgacccgg tattgagcta caccattgag aagaccatca | 300 |
| agaactggga tgagaagagg cgggagtggc tcgagaagca tccctcgttc gccgccggag | 360 |
| cagctgacag gattttaatg gtcacgggtt ctcaggcgac gccctgcaag aacccgatcg | 420 |
| gggatcactt gctgttgagg ttcttcaaga gtaaggcgga ctactgcagg atccacggct | 480 |
| acgatatctt ctacaacacc gtgctgctgc agccgaggat gttctcgttt tgggcaaaaa | 540 |
| tgcctgccgt gaaagcggtc atgttggccc atccggaggc ggagtggatc tggtgggtag | 600 |
| attcagacgc agccttcacc gacatggact tcacgctgcc gctggatcgc tacaaggccc | 660 |
| ataatttagt ggtccacggc tggcctcact tgattcacag ggagaagagc tggacggggc | 720 |
| tgaacgcggg agtgtttctg atgcgcaact gtcagtggtc aatggatttc atggaagaat | 780 |
| gggcgagcat ggggcctcaa gcctcggagt acgacaaatg gggcgtgatt cagcggacga | 840 |
| cgttcaagga caagacgttt ccggagtcag acgatcagac ggggttggct tatctgatcc | 900 |
| tgaaagagag agagaaatgg gggaacaaaa tttacatgga ggatgaatat tattttgagg | 960 |
| ggtgctggat ggaaatcgtg gggacgctgg agaacatcac cgacgcgtac acggggatcg | 1020 |
| agaagcggga gaggagattg aggaggaggc atgcagagag agtgggggag agttatggta | 1080 |
| aggtgtggga ggagcacctt aaggacgctg ggtatgggag | 1120 |

<210> SEQ ID NO 21

<211> LENGTH: 526
<212> TYPE: PRT
<213> ORGANISM: Cyamopsis tetragonoloba

<400> SEQUENCE: 21

| | | | | | | | | | | | | | | |
|---|---|---|---|---|---|---|---|---|---|---|---|---|---|---|
| Met | Arg | Asn | Leu | Ile | Phe | Glu | Glu | Pro | Glu | Gly | Ile | Pro | Gly | Asn | Ser |
| 1 | | | | 5 | | | | | 10 | | | | | 15 | |
| Ser | Ser | Ser | Leu | Arg | Tyr | Ala | Trp | Gln | Ser | Ile | Arg | Ala | Pro | Val | Ile |
| | | | 20 | | | | | 25 | | | | | 30 | | |
| Ile | Pro | Leu | Leu | Lys | Leu | Ala | Val | Ile | Val | Cys | Ser | Val | Met | Ser | Ile |
| | | | 35 | | | | | 40 | | | | | 45 | | |
| Met | Leu | Phe | Val | Glu | Arg | Val | Ala | Met | Ala | Ala | Val | Ile | Leu | Ile | Val |
| | 50 | | | | | 55 | | | | | 60 | | | | |
| Lys | Val | Leu | Arg | Lys | Lys | Arg | Tyr | Thr | Lys | Tyr | Asn | Leu | Glu | Ala | Met |
| 65 | | | | | 70 | | | | | 75 | | | | | 80 |
| Lys | Gln | Lys | Leu | Glu | Arg | Ser | Lys | Lys | Tyr | Pro | Met | Val | Leu | Ile | Gln |
| | | | | 85 | | | | | 90 | | | | | 95 | |
| Ile | Pro | Met | Tyr | Asn | Glu | Lys | Glu | Val | Tyr | Lys | Leu | Ser | Ile | Gly | Ala |
| | | | 100 | | | | | 105 | | | | | 110 | | |
| Val | Cys | Gly | Leu | Ser | Trp | Pro | Ala | Asp | Arg | Phe | Ile | Val | Gln | Val | Leu |
| | | | 115 | | | | | 120 | | | | | 125 | | |
| Asp | Asp | Ser | Thr | Asn | Pro | Val | Leu | Arg | Glu | Leu | Val | Glu | Met | Glu | Cys |
| | 130 | | | | | 135 | | | | | 140 | | | | |
| Gln | Lys | Trp | Ile | Gln | Lys | Gly | Val | Asn | Val | Lys | Tyr | Glu | Asn | Arg | Arg |
| 145 | | | | | 150 | | | | | 155 | | | | | 160 |
| Asn | Arg | Asn | Gly | Tyr | Lys | Ala | Gly | Ala | Leu | Lys | Glu | Gly | Leu | Glu | Lys |
| | | | | 165 | | | | | 170 | | | | | 175 | |
| Gln | Tyr | Val | Glu | Asp | Cys | Glu | Phe | Val | Ala | Ile | Phe | Asp | Ala | Asp | Phe |
| | | | 180 | | | | | 185 | | | | | 190 | | |
| Gln | Pro | Asp | Ala | Asp | Phe | Leu | Trp | Asn | Thr | Ile | Pro | Tyr | Leu | Leu | Glu |
| | | | 195 | | | | | 200 | | | | | 205 | | |
| Asn | Pro | Lys | Leu | Gly | Leu | Val | Gln | Ala | Arg | Trp | Lys | Phe | Val | Asn | Ser |
| | 210 | | | | | 215 | | | | | 220 | | | | |
| Glu | Glu | Cys | Met | Met | Thr | Arg | Leu | Gln | Glu | Met | Ser | Leu | Asp | Tyr | His |
| 225 | | | | | 230 | | | | | 235 | | | | | 240 |
| Phe | Ser | Val | Glu | Gln | Glu | Val | Gly | Ser | Ser | Thr | Tyr | Ser | Phe | Phe | Gly |
| | | | | 245 | | | | | 250 | | | | | 255 | |
| Phe | Asn | Gly | Thr | Ala | Gly | Val | Trp | Arg | Ile | Gln | Ala | Ile | Lys | Asp | Ala |
| | | | 260 | | | | | 265 | | | | | 270 | | |
| Gly | Gly | Trp | Lys | Asp | Arg | Thr | Thr | Val | Glu | Asp | Met | Asp | Leu | Ala | Val |
| | | | 275 | | | | | 280 | | | | | 285 | | |
| Arg | Ala | Ser | Leu | His | Gly | Trp | Glu | Phe | Val | Phe | Val | Gly | Asp | Val | Lys |
| | 290 | | | | | 295 | | | | | 300 | | | | |
| Val | Lys | Asn | Glu | Leu | Pro | Ser | Thr | Phe | Lys | Ala | Tyr | Arg | Phe | Gln | Gln |
| 305 | | | | | 310 | | | | | 315 | | | | | 320 |
| His | Arg | Trp | Ser | Cys | Gly | Pro | Ala | Asn | Leu | Phe | Lys | Lys | Met | Thr | Lys |
| | | | | 325 | | | | | 330 | | | | | 335 | |
| Glu | Ile | Ile | Cys | Cys | Lys | Arg | Val | Pro | Leu | Leu | Lys | Arg | Leu | His | Leu |
| | | | 340 | | | | | 345 | | | | | 350 | | |
| Ile | Tyr | Ala | Phe | Phe | Phe | Val | Arg | Lys | Ile | Val | Ala | His | Trp | Val | Thr |
| | | | 355 | | | | | 360 | | | | | 365 | | |
| Phe | Phe | Phe | Tyr | Cys | Ile | Val | Ile | Pro | Ala | Cys | Val | Ile | Val | Pro | Glu |
| | 370 | | | | | 375 | | | | | 380 | | | | |
| Val | Asn | Leu | Lys | Lys | Gln | Ile | Ala | Ile | Tyr | Ile | Pro | Ala | Thr | Ile | Thr |
| 385 | | | | | 390 | | | | | 395 | | | | | 400 |

```
Ile Leu Asn Ala Val Ser Thr Pro Arg Ser Met His Leu Leu Val Leu
                405                 410                 415

Trp Ile Leu Phe Glu Asn Val Met Ser Leu His Arg Thr Lys Ala Ala
            420                 425                 430

Ile Ile Gly Leu Leu Glu Ala Asn Arg Val Asn Glu Trp Val Val Thr
        435                 440                 445

Glu Lys Leu Gly Asn Ala Met Lys Gln Arg Asn Asn Ala Arg Pro Ser
    450                 455                 460

Arg Ala Ser Arg Phe Arg Ile Ile Glu Arg Ile His Pro Leu Glu Ile
465                 470                 475                 480

Ile Val Gly Met Tyr Met Leu His Cys Ala Thr Tyr Asp Leu Leu Phe
                485                 490                 495

Gly His Asp His Phe Phe Val Tyr Leu Leu Gln Ala Gly Ala Phe
            500                 505                 510

Phe Thr Met Gly Phe Gly Leu Val Gly Thr Ile Val Pro Thr
            515                 520                 525

<210> SEQ ID NO 22
<211> LENGTH: 533
<212> TYPE: PRT
<213> ORGANISM: Arabidopsis thaliana

<400> SEQUENCE: 22

Met Glu Leu Gly Asp Thr Thr Ser Val Ile Pro Asp Ser Phe Met Gly
1               5                   10                  15

Tyr Arg Asp Asp Ile Thr Met Gln Met Ser Met Val Leu Asp Gln Ile
            20                  25                  30

Arg Ala Pro Leu Ile Val Pro Ala Leu Arg Leu Gly Val Tyr Ile Cys
        35                  40                  45

Leu Thr Met Ser Val Met Leu Phe Val Glu Arg Val Tyr Met Gly Ile
    50                  55                  60

Val Ile Ser Leu Val Lys Leu Phe Gly Arg Lys Pro Asp Lys Arg Phe
65                  70                  75                  80

Lys Tyr Glu Pro Ile Lys Asp Asp Ile Glu Leu Gly Asn Ser Ala Tyr
                85                  90                  95

Pro Met Val Leu Ile Gln Ile Pro Met Phe Asn Glu Arg Glu Val Tyr
            100                 105                 110

Gln Leu Ser Ile Gly Ala Ala Cys Gly Leu Ser Trp Pro Ser Asp Arg
        115                 120                 125

Ile Val Ile Gln Val Leu Asp Asp Ser Thr Asp Pro Thr Ile Lys Asp
    130                 135                 140

Leu Val Glu Met Glu Cys Ser Arg Trp Ala Ser Lys Gly Val Asn Ile
145                 150                 155                 160

Lys Tyr Glu Ile Arg Asp Asn Arg Asn Gly Tyr Lys Ala Gly Ala Leu
                165                 170                 175

Lys Glu Gly Met Lys Lys Ser Tyr Val Lys Ser Cys Asp Tyr Val Ala
            180                 185                 190

Ile Phe Asp Ala Asp Phe Gln Pro Glu Ala Asp Phe Leu Trp Arg Thr
        195                 200                 205

Val Pro Tyr Leu Leu His Asn Pro Lys Leu Ala Leu Val Gln Ala Arg
    210                 215                 220

Trp Lys Phe Val Asn Ser Asp Glu Cys Leu Met Thr Arg Met Gln Glu
225                 230                 235                 240

Met Ser Leu Asp Tyr His Phe Thr Val Glu Gln Glu Val Gly Ser Ser
                245                 250                 255
```

Thr Tyr Ala Phe Phe Gly Phe Asn Gly Thr Ala Gly Ile Trp Arg Ile
            260                 265                 270

Ser Ala Leu Asn Glu Ala Gly Gly Trp Lys Asp Arg Thr Thr Val Glu
        275                 280                 285

Asp Met Asp Leu Ala Val Arg Ala Ser Leu Lys Gly Trp Lys Phe Leu
290                 295                 300

Tyr Leu Gly Ser Leu Lys Val Lys Asn Glu Leu Pro Ser Thr Phe Lys
305                 310                 315                 320

Ala Tyr Arg Tyr Gln Gln His Arg Trp Ser Cys Gly Pro Ala Asn Leu
                325                 330                 335

Phe Arg Lys Met Ala Phe Glu Ile Met Thr Asn Lys Asn Val Thr Leu
            340                 345                 350

Trp Lys Lys Val His Val Ile Tyr Ser Phe Phe Val Val Arg Lys Leu
        355                 360                 365

Val Ala His Ile Val Thr Phe Ile Phe Tyr Cys Val Ile Leu Pro Ala
    370                 375                 380

Thr Val Leu Val Pro Glu Val Thr Val Pro Lys Trp Gly Ala Val Tyr
385                 390                 395                 400

Ile Pro Ser Val Ile Thr Leu Leu Asn Ala Val Gly Thr Pro Arg Ser
                405                 410                 415

Leu His Leu Met Val Phe Trp Ile Leu Phe Glu Asn Val Met Ser Leu
            420                 425                 430

His Arg Thr Lys Ala Thr Phe Ile Gly Leu Leu Glu Gly Gly Arg Val
        435                 440                 445

Asn Glu Trp Ile Val Thr Glu Lys Leu Gly Asp Val Lys Ala Lys Ser
    450                 455                 460

Ala Thr Lys Thr Ser Lys Lys Val Ile Arg Phe Arg Phe Gly Asp Arg
465                 470                 475                 480

Ile His Val Leu Glu Leu Gly Val Gly Met Tyr Leu Leu Phe Val Gly
                485                 490                 495

Cys Tyr Asp Ala Phe Phe Gly Lys Asn His Tyr Tyr Leu Tyr Leu Phe
            500                 505                 510

Ala Gln Ala Ile Ala Phe Phe Ile Ala Gly Phe Gly Gln Ile Gly Thr
        515                 520                 525

Ile Val Pro Asn His
    530

<210> SEQ ID NO 23
<211> LENGTH: 537
<212> TYPE: PRT
<213> ORGANISM: Ipomoea trifida

<400> SEQUENCE: 23

Met Ala Gly Glu Thr Ile Asn Glu Val Glu Leu Met Met Pro Glu Leu
1               5                   10                  15

Arg Gly Pro Gly Gly Asp Met Ala Ala Gln Met Arg Leu Met Tyr Asp
            20                  25                  30

Leu Val Lys Ala Pro Leu Ile Val Pro Val Leu Arg Leu Ala Val Tyr
        35                  40                  45

Val Cys Leu Thr Met Ser Met Met Leu Phe Val Glu Arg Leu Tyr Met
    50                  55                  60

Gly Ile Val Ile Ile Leu Val Lys Ile Phe Cys Gly Lys Pro Glu Lys
65                  70                  75                  80

Arg Tyr Lys Trp Glu Pro Met Arg Glu Asp Tyr Glu Ile Gly Thr Ser
                85                  90                  95

Val Phe Pro Ser Val Leu Ile Gln Ile Pro Met Phe Asn Glu Lys Glu
                100                 105                 110

Val Tyr Lys Ile Ser Ile Gly Ala Val Cys Asn Phe Ala Trp Pro Ser
            115                 120                 125

Asp Arg Leu Val Val Gln Val Leu Asp Asp Ser Thr Asp His Asn Ile
        130                 135                 140

Lys Glu Met Val Glu Lys Glu Cys Leu Arg Trp Ala Ser Lys Gly Ile
145                 150                 155                 160

Asn Ile Thr Tyr Gln Thr Arg Val Thr Arg Gly Gly Tyr Lys Ala Gly
                165                 170                 175

Ala Leu Lys Glu Gly Leu Thr His Asp Tyr Val Gln Asp Cys Glu Tyr
            180                 185                 190

Val Ala Ile Phe Asp Ala Asp Phe Arg Pro Glu Pro Asp Phe Leu Leu
        195                 200                 205

Arg Ser Ile Pro Phe Leu Ile His Asn Pro Glu Ile Ala Leu Ile Gln
    210                 215                 220

Ala Arg Trp Arg Phe Val Asn Ala Asp Glu Cys Leu Leu Thr Arg Met
225                 230                 235                 240

Gln Glu Met Ser Leu Asp Tyr His Phe Lys Val Glu Gln Glu Val Gly
                245                 250                 255

Ser Ser Thr His Ala Phe Phe Gly Phe Asn Gly Thr Gly Gly Ile Trp
            260                 265                 270

Arg Ile Ala Ala Ile Asn Glu Ala Gly Gly Trp Lys Asp Arg Thr Thr
        275                 280                 285

Val Glu Asp Met Asp Leu Ala Val Arg Ala Gly Leu Lys Gly Trp Lys
    290                 295                 300

Phe Leu Tyr Leu Gly Asp Leu His Val Lys Ser Glu Leu Pro Ser Thr
305                 310                 315                 320

Phe Lys Ala Phe Arg Phe Gln Gln His Arg Trp Ser Cys Gly Pro Ala
                325                 330                 335

Asn Leu Phe Arg Lys Met Phe Met Glu Ile Val Arg Asn Lys Arg Val
            340                 345                 350

Asn Val Trp Lys Lys Val Tyr Val Ile Tyr Ser Phe Phe Leu Val Arg
        355                 360                 365

Lys Ile Thr Ala His Met Val Thr Phe Phe Phe Tyr Cys Val Val Leu
    370                 375                 380

Pro Leu Thr Ile Leu Val Pro Glu Val Glu Val Pro Lys Trp Gly Ala
385                 390                 395                 400

Ile Tyr Ile Pro Cys Ile Ile Thr Ile Leu Asn Ser Val Gly Thr Pro
                405                 410                 415

Arg Ser Ile His Leu Leu Phe Tyr Trp Ile Leu Phe Glu Asn Val Met
            420                 425                 430

Ser Phe His Arg Thr Lys Ala Thr Leu Ile Gly Leu Leu Glu Phe Lys
        435                 440                 445

Arg Ala Asn Glu Trp Val Val Thr Glu Lys Leu Gly Asp Ala Ile Asn
    450                 455                 460

Asn Asn Asn Lys Ser Asn Ser Lys Pro Ala Pro Lys Lys Thr Lys Ser
465                 470                 475                 480

Ile Phe Lys Asp Arg Ile Leu Leu His Glu Leu Gly Phe Ala Val Phe
                485                 490                 495

Leu Phe Val Cys Gly Val Tyr Asp Tyr Leu His Gly Lys Asn His Tyr
            500                 505                 510

Tyr Ile Tyr Leu Phe Leu Gln Val Ile Thr Phe Thr Ile Ala Gly Val

Gly Trp Val Gly Thr Ile Val Pro Ser
            530                 535

<210> SEQ ID NO 24
<211> LENGTH: 437
<212> TYPE: PRT
<213> ORGANISM: Lotus japonicus

<400> SEQUENCE: 24

Met Ala Arg Leu Gly Ser Arg Asn Lys Ser Leu Trp Leu Ser Asp
1               5                   10                  15

Gly Cys Cys Phe Leu Thr Gly Ala Leu Ser Ala Leu Leu Val Trp
                20                  25                  30

Gly Leu Cys Ser Phe Ile Ile Pro Phe Pro Asn Thr Asp Pro Lys Leu
                35                  40                  45

Asn Ser Val Ala Ala Lys Leu Lys Ser Leu Asn Leu Pro Arg Asn Gln
50                      55                      60

Ile Thr Thr Ser Ser Ala Gln Asp Leu Leu Tyr Asp Ser Pro Glu Thr
65                      70                  75                  80

Thr Phe Tyr Asp Asp Pro Glu Met Ser Tyr Thr Met Asp Lys Pro Val
                    85                  90                  95

Thr Asn Trp Asp Glu Lys Arg Arg Gln Trp Leu Leu His His Pro Ser
                100                 105                 110

Phe Ala Ala Gly Ala Ser Asp Arg Ile Leu Leu Val Thr Gly Ser Gln
                115                 120                 125

Pro Lys Arg Cys His Asn Pro Ile Gly Asp His Leu Leu Leu Arg Phe
            130                 135                 140

Phe Lys Asn Lys Val Asp Tyr Cys Arg Ile His Asp Ile Asp Ile Ile
145                 150                 155                 160

Tyr Asn Asn Ala Leu Leu His Pro Lys Met Asn Ser Tyr Trp Ala Lys
                    165                 170                 175

Tyr Pro Val Val Lys Ala Ala Met Ile Ala His Pro Glu Val Glu Trp
                180                 185                 190

Ile Trp Trp Val Asp Ser Asp Ala Val Ile Thr Asp Met Glu Phe Lys
                195                 200                 205

Leu Pro Leu Asn Arg Tyr Asn Glu Phe Asn Leu Ile Ile His Gly Trp
210                 215                 220

Glu Asp Leu Val Lys Lys Lys His Ser Trp Thr Gly Leu Asn Ala Gly
225                 230                 235                 240

Val Phe Leu Met Arg Asn Cys Gln Trp Ser Leu Asp Phe Met Asp Val
                    245                 250                 255

Trp Ala Ala Met Gly Pro Ser Ser Pro Asp Tyr Lys Lys Trp Gly Glu
                260                 265                 270

Lys Leu Met Ala Thr Phe Lys Asp Lys Val Ile Pro Asp Ser Asp Asp
                275                 280                 285

Gln Thr Ala Leu Ala Tyr Leu Ile Ala Met Gly Glu Asp Lys Trp Thr
            290                 295                 300

Glu Lys Ile Tyr Leu Glu Lys Asp Tyr Tyr Phe Glu Gly Tyr Trp Val
305                 310                 315                 320

Glu Leu Ala Lys Met Tyr Glu Asn Val Ser Val Arg Tyr Asp Glu Val
                    325                 330                 335

Glu Arg Arg Val Gly Gly Leu Arg Arg Arg His Ala Glu Lys Val Ser
                340                 345                 350

Glu Arg Tyr Gly Glu Met Arg Glu Glu His Val Lys Tyr Phe Gly Gln

```
                   355                 360                 365
Trp Arg Arg Pro Phe Ile Thr His Phe Thr Gly Cys Gln Pro Cys Asn
    370                 375                 380

Gly His His Asn Pro Ala Tyr Ala Ala Asp Asp Cys Trp Asn Gly Met
385                 390                 395                 400

Asp Arg Ala Leu Asn Phe Ala Asp Asn Gln Val Leu Arg Thr Tyr Gly
                405                 410                 415

Tyr Val Arg Arg Ser Leu Asn Asp Lys Ala Val Thr Pro Ile Pro Tyr
            420                 425                 430

Asp Tyr Pro Ala Ala
            435

<210> SEQ ID NO 25
<211> LENGTH: 438
<212> TYPE: PRT
<213> ORGANISM: Trigonella foenum-graecum

<400> SEQUENCE: 25

Ala Thr Lys Phe Gly Ser Lys Asn Lys Ser Ser Pro Trp Leu Ser Asn
1               5                   10                  15

Gly Cys Ile Phe Leu Leu Gly Ala Met Ser Ala Leu Leu Met Ile Trp
            20                  25                  30

Gly Leu Asn Ser Phe Ile Ala Pro Ile Pro Asn Ser Asn Pro Lys Phe
        35                  40                  45

Asn Ser Phe Thr Thr Lys Leu Lys Ser Leu Asn Phe Thr Thr Asn Thr
    50                  55                  60

Asn Phe Ala Gly Pro Asp Leu Leu His Asp Pro Ser Asp Lys Thr Phe
65                  70                  75                  80

Tyr Asp Asp Pro Glu Thr Cys Tyr Thr Met Met Asp Lys Pro Met Lys
                85                  90                  95

Asn Trp Asp Glu Lys Arg Lys Glu Trp Leu Phe His His Pro Ser Phe
            100                 105                 110

Ala Ala Gly Ala Thr Glu Lys Ile Leu Val Ile Thr Gly Ser Gln Pro
        115                 120                 125

Thr Lys Cys Asp Asn Pro Ile Gly Asp His Leu Leu Leu Arg Phe Tyr
    130                 135                 140

Lys Asn Lys Val Asp Tyr Cys Arg Ile His Asn His Asp Ile Ile Tyr
145                 150                 155                 160

Asn Asn Ala Leu Leu His Pro Lys Met Asp Ser Tyr Trp Ala Lys Tyr
                165                 170                 175

Pro Met Val Arg Ala Ala Met Leu Ala His Pro Glu Val Glu Trp Ile
            180                 185                 190

Trp Trp Val Asp Ser Asp Ala Ile Phe Thr Asp Met Glu Phe Lys Leu
        195                 200                 205

Pro Leu Trp Arg Tyr Lys Asp His Asn Leu Val Ile His Gly Trp Glu
    210                 215                 220

Glu Leu Val Lys Thr Glu His Ser Trp Thr Gly Leu Asn Ala Gly Val
225                 230                 235                 240

Phe Leu Met Arg Asn Cys Gln Trp Ser Leu Asp Phe Met Asp Val Trp
                245                 250                 255

Ala Ser Met Gly Pro Asn Ser Pro Glu Tyr Glu Lys Trp Gly Glu Arg
            260                 265                 270

Leu Arg Glu Thr Phe Lys Thr Lys Val Val Arg Asp Ser Asp Asp Gln
        275                 280                 285

Thr Ala Leu Ala Tyr Leu Ile Ala Met Gly Glu Asp Lys Trp Thr Lys
```

```
            290                 295                 300
Lys Ile Tyr Met Glu Asn Glu Tyr Tyr Phe Glu Gly Tyr Trp Leu Glu
305                 310                 315                 320

Ile Ser Lys Met Tyr Asp Lys Met Gly Glu Arg Tyr Asp Glu Ile Glu
                325                 330                 335

Lys Arg Val Glu Gly Leu Arg Arg His Ala Glu Lys Val Ser Glu
            340                 345                 350

Arg Tyr Gly Glu Met Arg Glu Glu Tyr Val Lys Asn Leu Gly Asp Met
                355                 360                 365

Arg Arg Pro Phe Ile Thr His Phe Thr Gly Cys Gln Pro Cys Asn Gly
370                 375                 380

His His Asn Pro Ile Tyr Ala Ala Asp Asp Cys Trp Asn Gly Met Glu
385                 390                 395                 400

Arg Ala Leu Asn Phe Ala Asp Asn Gln Val Leu Arg Lys Phe Gly Phe
                405                 410                 415

Ile His Pro Asn Leu Leu Asp Lys Ser Val Ser Pro Leu Pro Phe Gly
                420                 425                 430

Tyr Pro Ala Ala Ser Pro
                435

<210> SEQ ID NO 26
<211> LENGTH: 438
<212> TYPE: PRT
<213> ORGANISM: Trigonella foenum-graecum

<400> SEQUENCE: 26

Ala Thr Lys Phe Gly Ser Lys Asn Lys Ser Ser Pro Trp Leu Ser Asn
1               5                   10                  15

Gly Cys Ile Phe Leu Leu Gly Ala Met Ser Ala Leu Leu Met Ile Trp
            20                  25                  30

Gly Leu Asn Ser Phe Ile Ala Pro Ile Pro Asn Ser Asn Pro Lys Phe
        35                  40                  45

Asn Ser Phe Thr Thr Lys Leu Lys Ser Leu Asn Phe Thr Thr Asn Thr
    50                  55                  60

Asn Phe Ala Gly Pro Asp Leu Leu His Asp Pro Ser Asp Lys Thr Phe
65                  70                  75                  80

Tyr Asp Asp Pro Glu Thr Cys Tyr Thr Met Met Asp Lys Pro Met Lys
                85                  90                  95

Asn Trp Asp Glu Lys Arg Lys Glu Trp Leu Phe His His Pro Ser Phe
            100                 105                 110

Ala Ala Gly Ala Thr Glu Lys Ile Leu Val Ile Thr Gly Ser Gln Pro
        115                 120                 125

Thr Lys Cys Asp Asn Pro Ile Gly Asp His Leu Leu Leu Arg Phe Tyr
    130                 135                 140

Lys Asn Lys Val Asp Tyr Cys Arg Ile His Asn His Asp Ile Ile Tyr
145                 150                 155                 160

Asn Asn Ala Leu Leu His Pro Lys Met Asp Ser Tyr Trp Ala Lys Tyr
                165                 170                 175

Pro Met Val Arg Ala Ala Met Leu Ala His Pro Glu Val Glu Trp Ile
            180                 185                 190

Trp Trp Val Asp Ser Asp Ala Ile Phe Thr Asp Met Glu Phe Lys Leu
        195                 200                 205

Pro Leu Trp Arg Tyr Lys Asp His Asn Leu Val Ile His Gly Trp Glu
    210                 215                 220

Glu Leu Val Lys Thr Glu His Ser Trp Thr Gly Leu Asn Ala Gly Val
```

```
                        225                 230                 235                 240
Phe Leu Met Arg Asn Cys Gln Trp Ser Leu Asp Phe Met Asp Val Trp
                    245                 250                 255

Ala Ser Met Gly Pro Asn Ser Pro Glu Tyr Glu Lys Trp Gly Glu Arg
                260                 265                 270

Leu Arg Glu Thr Phe Lys Thr Lys Val Val Arg Asp Ser Asp Asp Gln
            275                 280                 285

Thr Ala Leu Ala Tyr Leu Ile Ala Met Gly Glu Asp Lys Trp Thr Lys
        290                 295                 300

Lys Ile Tyr Met Glu Asn Glu Tyr Tyr Phe Glu Gly Tyr Trp Leu Glu
305                 310                 315                 320

Ile Ser Lys Met Tyr Asp Lys Met Gly Glu Arg Tyr Asp Glu Ile Glu
                325                 330                 335

Lys Arg Val Glu Gly Leu Arg Arg His Ala Glu Lys Val Ser Glu
            340                 345                 350

Arg Tyr Gly Glu Met Arg Glu Glu Tyr Val Lys Asn Leu Gly Asp Met
        355                 360                 365

Arg Arg Pro Phe Ile Thr His Phe Thr Gly Cys Gln Pro Cys Asn Gly
    370                 375                 380

His His Asn Pro Ile Tyr Ala Ala Asp Asp Cys Trp Asn Gly Met Glu
385                 390                 395                 400

Arg Ala Leu Asn Phe Ala Asp Asn Gln Val Leu Arg Lys Phe Gly Phe
                405                 410                 415

Ile His Pro Asn Leu Leu Asp Lys Ser Val Ser Pro Leu Pro Phe Gly
            420                 425                 430

Tyr Pro Ala Ala Ser Pro
        435

<210> SEQ ID NO 27
<211> LENGTH: 443
<212> TYPE: PRT
<213> ORGANISM: Solanum tuberosum

<400> SEQUENCE: 27

Met Ala His Asn Val Phe Arg Ala Lys Gln Gln Ser Ser Ser Pro Arg
1               5                   10                  15

Asp Lys Ser Leu Phe Ala Ala Ile Val Ala Leu Leu Val Cys
            20                  25                  30

Ala Ile Trp Ser Phe Thr Asp Pro Leu Pro Asn Leu Ser Gly Leu Leu
        35                  40                  45

Tyr Ser Gln Ser Ile Ser Ser Pro Asp Tyr Cys Pro Pro Gly Arg Glu
    50                  55                  60

Ala Val Asp Arg Ser Ser Asp Pro Leu Glu Lys Thr Phe Tyr Asp Glu
65                  70                  75                  80

Pro Glu Leu Ser Tyr Thr Ile Asn Lys Pro Ile Lys Asn Trp Asp Glu
                85                  90                  95

Lys Arg Val Gln Trp Leu Lys Leu His Pro Ser Phe Ala Ala Gly Arg
            100                 105                 110

Val Asn Arg Val Leu Leu Ser Gly Ser Gln Pro Thr Pro Cys Lys
        115                 120                 125

Asn Ala Arg Gly Asp His Leu Leu Leu Arg Phe Phe Lys Asn Lys Val
    130                 135                 140

Asp Tyr Cys Arg Ile His Gly Tyr Asp Ile Phe Tyr Gly Asn Thr Phe
145                 150                 155                 160

Phe His Pro Lys Met Arg Ser Tyr Trp Ala Lys Ile Pro Leu Val Arg
```

```
                165                 170                 175
Ala Ala Met Leu Ala His Pro Glu Ser Glu Trp Ile Leu Trp Ile Asp
            180                 185                 190

Ser Asp Ala Ile Phe Thr Asp Met Asp Phe Lys Ile Pro Leu His Lys
            195                 200                 205

Tyr Asn Asp Tyr Asn Phe Ile Val His Gly Trp Pro Asp Leu Ile Phe
            210                 215                 220

Lys Lys Lys Ser Trp Val Ala Ile Asn Ala Gly Ile Phe Leu Ile Arg
225                 230                 235                 240

Asn Cys Gln Trp Ser Met Asp Phe Leu Asp Val Trp Ala Asn Met Gly
                245                 250                 255

Pro Lys Ser Pro Glu Tyr Lys Gln Trp Gly Lys Ile Leu Arg Thr Thr
            260                 265                 270

Phe Lys Asp Lys Thr Phe Pro Glu Ser Asp Asp Gln Ser Ala Leu Ser
            275                 280                 285

Tyr Leu Ile Leu Lys Gly Glu Arg Lys Trp Arg Ser Lys Ile His Ala
            290                 295                 300

Ile Thr Asp Tyr Ser Leu His Gly Tyr Trp Leu Gly Ile Val Asn Arg
305                 310                 315                 320

Phe Asp Lys Ile Thr Glu Asn Tyr Thr Lys Ile Glu Arg Asp Val Pro
                325                 330                 335

Lys Leu Arg Arg Arg His Ala Glu Ala Val Ser Asp Ser Tyr Ala Glu
            340                 345                 350

Ala Arg Glu Pro Leu Leu Ala Glu Gly Ala Asp Gly Lys Gly Gly Trp
            355                 360                 365

Arg Arg Pro Phe Ile Thr His Phe Thr Gly Cys Gln Pro Cys Ser Gly
            370                 375                 380

Asp His Ala Ala Glu Tyr Val Gly Asp Ser Cys Trp Val Gly Met Glu
385                 390                 395                 400

Arg Ala Leu Asn Phe Ala Asp Asn Gln Val Leu Arg Asn Phe Gly Phe
                405                 410                 415

Met His Asp Asp Ile Lys Ser Asn Ser Pro Val Ser Pro Leu Asn Phe
            420                 425                 430

Asp Phe Pro Ala Glu Asp Ser Glu Glu Phe Val
            435                 440

<210> SEQ ID NO 28
<211> LENGTH: 443
<212> TYPE: PRT
<213> ORGANISM: Nicotiana benthamiana

<400> SEQUENCE: 28

Met Ala His Asn Val Phe Arg Ala Lys Gln Gln Ser Ser Ser Leu Arg
1               5                   10                  15

Asp Lys Ser Leu Phe Leu Ala Ile Val Ala Leu Leu Leu Ala Cys
            20                  25                  30

Ala Ile Trp Ser Phe Thr Asp Pro Phe Pro Asn Phe Ser Asn Leu Leu
            35                  40                  45

Ser Lys Gln Asn Val Thr Ser Pro Glu Tyr Cys Pro Pro Asp Arg Glu
        50                  55                  60

Ala Val Asp Arg Ile Tyr Asp Pro Pro Glu Lys Thr Phe Tyr Asp Asp
65                  70                  75                  80

Pro Asp Leu Ser Tyr Thr Ile Asn Lys Pro Ile Lys Asn Trp Glu Glu
                85                  90                  95

Lys Arg Ile Glu Trp Leu Lys Leu His Pro Ser Phe Ala Ala Gly Arg
```

```
        100                 105                 110
Ala Lys Arg Val Leu Leu Thr Gly Ser Gln Pro Thr Pro Cys Lys
        115                 120                 125

Tyr Pro Ile Gly Asp His Leu Leu Arg Phe Phe Lys Asn Lys Val
        130                 135             140

Asp Tyr Cys Arg Ile His Gly Tyr Asp Ile Phe Tyr Gly Asn Thr Leu
145                 150                 155                 160

Leu His Pro Lys Met Arg Ser Tyr Trp Ala Lys Ile Pro Leu Val Arg
                    165                 170                 175

Ala Ala Met Leu Ala His Pro Glu Ser Glu Trp Ile Leu Trp Ile Asp
                180                 185                 190

Ser Asp Ala Ile Phe Thr Asp Met Asp Phe Lys Ile Pro Leu His Lys
            195                 200                 205

Tyr Lys Glu Tyr Asn Phe Ile Val His Gly Trp Pro Asp Leu Ile Phe
        210                 215                 220

Lys Lys Lys Ser Trp Val Ala Ile Asn Ala Gly Ile Phe Leu Ile Arg
225                 230                 235                 240

Asn Cys Gln Trp Ser Met Asp Phe Leu Asp Val Trp Ala Asn Met Gly
                    245                 250                 255

Pro Lys Ser Pro Glu Tyr Lys Lys Trp Gly Lys Ile Leu Arg Ser Thr
                260                 265                 270

Phe Lys Asp Lys Thr Phe Pro Glu Ser Asp Asp Gln Ser Ala Leu Ser
            275                 280                 285

Tyr Val Ile Met Lys Gly Glu Glu Lys Trp Arg Ser Lys Ile His Ala
        290                 295                 300

Ile Thr Asp Tyr Ser Leu His Gly Tyr Trp Leu Gly Ile Val Asp Arg
305                 310                 315                 320

Phe Asp Asn Ile Thr Gly Asn Tyr Glu Lys Ile Asp Arg Asp Val Pro
                    325                 330                 335

Lys Leu Arg Arg Arg His Ala Glu Ser Val Ser Glu Tyr Ala Ala
                340                 345                 350

Ala Arg Glu Pro Leu Val Ala Glu Gly Gly Asp Trp Lys Gly Gly Trp
            355                 360                 365

Arg Arg Pro Phe Ile Thr His Phe Thr Gly Cys Gln Pro Cys Ser Gly
370                 375                 380

Asp His Val Ser Glu Tyr Val Gly Asp Lys Cys Trp Val Gly Met Glu
385                 390                 395                 400

Arg Ala Leu Asn Phe Ala Asp Asn Gln Val Leu Arg Asn Phe Gly Phe
                    405                 410                 415

Met His Val Asp Ile Lys Ser Asn Ser Pro Val Thr Pro Val Asn Phe
                420                 425                 430

Asp Phe Pro Ala Glu Glu Val Glu Glu Phe Val
            435                 440

<210> SEQ ID NO 29
<211> LENGTH: 438
<212> TYPE: PRT
<213> ORGANISM: Medicago truncatula

<400> SEQUENCE: 29

Met Ala Pro Lys Phe Gly Ser Lys Asn Lys Ser Ser Ser Trp Leu Ser
1               5                   10                  15

Ser Gly Cys Ile Phe Ile Leu Gly Ala Met Ala Ala Leu Leu Phe Ile
            20                  25                  30

Trp Gly Leu Ser Ser Phe Ile Thr Pro Ile Ser Asn Thr Asn Pro Lys
```

```
                 35                  40                  45
Phe Asn Ser Ile Thr Thr Lys Leu Lys Ser Phe Asn Phe Thr Thr Asn
 50                  55                  60

Thr Asp Phe Ala Gly Pro Asp Phe Leu His Asp Pro Ser Asp Lys Thr
 65                  70                  75                  80

Phe Tyr Asp Asp Pro Gln Thr Cys Tyr Thr Met Asp Lys Pro Val Lys
                 85                  90                  95

Asn Trp Asp Glu Lys Arg Lys Glu Trp Leu Leu His His Pro Ser Phe
                100                 105                 110

Val Val Gly Ala Ser Glu Lys Ile Leu Val Ile Thr Gly Ser Gln Pro
                115                 120                 125

Thr Lys Cys Asp Asn Pro Ile Gly Asp His Leu Leu Leu Arg Phe Phe
                130                 135                 140

Lys Asn Lys Val Asp Tyr Cys Arg Ile His Asn His Asp Ile Ile Tyr
145                 150                 155                 160

Asn Asn Ala Leu Leu Asp Pro Lys Met Asp Thr Tyr Trp Ala Lys Tyr
                165                 170                 175

Pro Met Val Arg Ala Ala Met Leu Ala His Pro Glu Val Glu Trp Ile
                180                 185                 190

Trp Trp Val Asp Ser Asp Ala Ile Phe Thr Asp Met Glu Phe Lys Leu
                195                 200                 205

Pro Leu Trp Arg Tyr Asn Asp His Asn Leu Val Ile His Gly Trp Glu
                210                 215                 220

Glu Leu Val Lys Lys Glu His Ser Trp Thr Gly Leu Asn Ala Gly Val
225                 230                 235                 240

Phe Leu Ile Arg Asn Cys Gln Trp Ser Leu Asp Phe Met Asp Val Trp
                245                 250                 255

Ala Ser Met Gly Pro Asn Ser Pro Glu Tyr Glu Lys Trp Gly Glu Arg
                260                 265                 270

Leu Arg Ala Thr Phe Lys Thr Lys Val Val Pro Asp Ser Asp Asp Gln
                275                 280                 285

Thr Ala Leu Ala Tyr Leu Ile Ala Met Gly Glu Asp Lys Trp Thr Lys
                290                 295                 300

Lys Ile Tyr Met Glu Asn Glu Tyr Tyr Phe Glu Gly Tyr Trp Met Glu
305                 310                 315                 320

Ile Ser Lys Met Tyr Asp Lys Met Gly Lys Tyr Asp Glu Ile Glu
                325                 330                 335

Lys Arg Val Glu Gly Leu Arg Arg His Ala Glu Lys Val Ser Glu
                340                 345                 350

Arg Tyr Gly Glu Met Arg Glu Glu Tyr Val Lys Asn Leu Gly Asp Met
                355                 360                 365

Arg Arg Pro Phe Ile Thr His Phe Thr Gly Cys Gln Pro Cys Asn Gly
                370                 375                 380

His His Asn Pro Met Tyr Ala Asp Asp Cys Trp Asn Gly Met Glu
385                 390                 395                 400

Arg Ala Leu Asn Phe Ala Asp Asn Gln Val Leu Arg Lys Phe Gly Phe
                405                 410                 415

Ile His Pro Asn Leu Leu Asp Lys Ser Val Ser Pro Leu Pro Phe Gly
                420                 425                 430

Tyr Pro Ala Lys Ser Pro
                435

<210> SEQ ID NO 30
<211> LENGTH: 422
```

```
<212> TYPE: PRT
<213> ORGANISM: Medicago truncatula

<400> SEQUENCE: 30
```

| | | | | | | | | | | | | | | |
|---|---|---|---|---|---|---|---|---|---|---|---|---|---|---|
| Met | Thr | Asn | Ala | Lys | Arg | Lys | Arg | Gly | Cys | Ser | Ile | Pro | Asn | Arg | Asn |
| 1 | | | | 5 | | | | | 10 | | | | | 15 | |

Gly Tyr Gly Glu Phe Pro Ile Leu Lys Ala Thr Leu Phe Val Leu Leu
                    20                  25                  30

Leu Leu Leu Cys Ala Leu Trp Phe Lys Arg Asn Gln Leu Thr Ile Leu
            35                  40                  45

Cys Pro Asn Lys Thr Met Ser Glu Ala Ile Gln Asp Pro Pro Glu Lys
        50                  55                  60

Thr Phe Tyr Asp Asp Pro Thr Leu Ser Tyr Ser Val Glu Glu Pro Met
65                  70                  75                  80

Lys Gln Trp Asp Lys Lys Arg Ser His Trp Leu Gln Leu His Pro Ser
                85                  90                  95

Phe Ala Ala Gly Ala Ser Asp Arg Ile Leu Val Leu Thr Gly Ser Gln
            100                 105                 110

Pro Thr Pro Cys Lys Asn Pro Ile Gly Asp His Leu Leu Leu Arg Cys
        115                 120                 125

Phe Lys Asn Lys Val Asp Tyr Cys Arg Ile His Asn Cys Glu Val Tyr
130                 135                 140

Tyr Ser Asn Leu His Leu His Pro Lys Met Asp Ser Tyr Trp Ser Lys
145                 150                 155                 160

Leu Pro Ile Ile Arg Ser Thr Met Met Ala His Pro Glu Val Glu Trp
                165                 170                 175

Ile Trp Trp Met Asp Ala Asp Ala Val Phe Ser Asp Met Glu Phe Lys
            180                 185                 190

Val Pro Leu Asp Arg Tyr Lys Asp His Asn Leu Val Val His Gly Trp
        195                 200                 205

Ser Asn Met Val Tyr Asp Asp Ser Glu Asn Lys Ser Trp Thr Gly Leu
210                 215                 220

Asn Ala Gly Ser Ile Leu Val Arg Asn Cys Gln Trp Ser Met Asp Leu
225                 230                 235                 240

Leu His Val Trp Ala Gln Met Gly Pro Leu Thr Ser Asn Tyr Ala Lys
                245                 250                 255

Trp Gly Lys Ile Leu Thr Ser Ile Phe Lys Asp Lys Pro Phe Pro Leu
            260                 265                 270

Pro Asp Asp Gln Ser Ser Leu Ile Tyr Leu Leu Ser Arg Gln Arg Arg
        275                 280                 285

Lys Trp Gly Ala Lys Thr Phe Leu Glu Glu Gly Tyr Asp Leu Glu Gly
    290                 295                 300

Tyr Trp Ile Ala Thr Met Gly Lys Leu Glu Gly Ile Gln Asn Lys Tyr
305                 310                 315                 320

Asp Glu Ile Glu Lys Lys Ala Arg Val Leu Arg Arg His Ser Glu
                325                 330                 335

Lys Val Ser Val Trp Tyr Gly Glu Met Arg Glu Pro Tyr Leu Lys Trp
            340                 345                 350

Ser Glu Arg Arg Pro Phe Val Lys His Phe Thr Gly Cys Gln Pro Cys
        355                 360                 365

Ser Gly Asp His Asn Pro Ser Tyr Lys Gly Asp Val Cys Trp Lys Glu
    370                 375                 380

Met Glu Arg Ala Leu Asn Phe Ala Asp Asn Gln Val Leu Arg Asn Tyr
385                 390                 395                 400

```
Gly Phe Val Arg Lys Asn Leu Met Thr Ser Val Tyr Glu Val Pro
                405                 410                 415

Phe Gly Tyr Pro Arg Asp
            420
```

<210> SEQ ID NO 31
<211> LENGTH: 435
<212> TYPE: PRT
<213> ORGANISM: Cyamopsis tetragonoloba

<400> SEQUENCE: 31

```
Met Ala Lys Phe Gly Ser Arg Asn Lys Ser Pro Lys Trp Ile Ser Asn
1               5                   10                  15

Gly Cys Cys Phe Leu Leu Gly Ala Phe Thr Ala Leu Leu Leu Leu Trp
                20                  25                  30

Gly Leu Cys Ser Phe Ile Ile Pro Ile Pro Asn Thr Asp Pro Lys Leu
            35                  40                  45

Asn Ser Val Ala Thr Ser Leu Arg Ser Leu Asn Phe Pro Lys Asn Pro
        50                  55                  60

Ala Ala Thr Leu Pro Pro Asn Leu Gln His Asp Pro Pro Asp Thr Thr
65                  70                  75                  80

Phe Tyr Asp Asp Pro Glu Thr Ser Tyr Thr Met Asp Lys Pro Met Lys
                85                  90                  95

Asn Trp Asp Glu Lys Arg Lys Glu Trp Leu Leu His Pro Ser Phe
            100                 105                 110

Gly Ala Ala Ala Arg Asp Lys Ile Leu Leu Val Thr Gly Ser Gln Pro
            115                 120                 125

Lys Arg Cys His Asn Pro Ile Gly Asp His Leu Leu Leu Arg Phe Phe
130                 135                 140

Lys Asn Lys Val Asp Tyr Cys Arg Leu His Asn Tyr Asp Ile Ile Tyr
145                 150                 155                 160

Asn Asn Ala Leu Leu His Pro Lys Met Asn Ser Tyr Trp Ala Lys Tyr
                165                 170                 175

Pro Val Ile Arg Ala Ala Met Met Ala His Pro Glu Val Glu Trp Val
            180                 185                 190

Trp Trp Val Asp Ser Asp Ala Val Phe Thr Asp Met Glu Phe Lys Leu
        195                 200                 205

Pro Leu Lys Arg Tyr Lys Asn His Asn Leu Val Val His Gly Trp Glu
    210                 215                 220

Gly Leu Val Arg Leu Asn His Ser Trp Thr Gly Leu Asn Ala Gly Val
225                 230                 235                 240

Phe Leu Ile Arg Asn Cys Gln Trp Ser Leu Glu Phe Met Asp Val Trp
                245                 250                 255

Val Ser Met Gly Pro Gln Thr Pro Glu Tyr Glu Lys Trp Gly Glu Arg
            260                 265                 270

Leu Arg Glu Thr Phe Lys Asp Lys Val Leu Pro Asp Ser Asp Gln
        275                 280                 285

Thr Ala Leu Ala Tyr Leu Ile Ala Thr Asp Asn Lys Asp Thr Trp Arg
    290                 295                 300

Glu Lys Ile Phe Leu Glu Ser Glu Tyr Tyr Phe Glu Gly Tyr Trp Leu
305                 310                 315                 320

Glu Ile Val Lys Thr Tyr Glu Asn Ile Ser Glu Arg Tyr Asp Glu Val
                325                 330                 335

Glu Arg Lys Val Glu Gly Leu Arg Arg His Ala Glu Lys Val Ser
            340                 345                 350
```

-continued

```
Glu Lys Tyr Gly Ala Met Arg Glu Glu Tyr Leu Lys Asp Asn Lys Arg
            355                 360                 365

Arg Pro Phe Ile Thr His Phe Thr Gly Cys Gln Pro Cys Asn Gly His
        370                 375                 380

His Asn Pro Ala Tyr Asn Ala Asn Asp Cys Trp Asn Gly Met Glu Arg
385                 390                 395                 400

Ala Leu Asn Phe Ala Asp Asn Gln Ile Leu Arg Thr Tyr Gly Tyr His
                405                 410                 415

Arg Gln Asn Leu Leu Asp Lys Ser Val Ser Pro Leu Pro Phe Gly Tyr
            420                 425                 430

Pro Ala Ala
        435

<210> SEQ ID NO 32
<211> LENGTH: 449
<212> TYPE: PRT
<213> ORGANISM: Senna occidentalis

<400> SEQUENCE: 32

Met Ala Lys Ser Val Arg Asn Lys Ser Ser Leu Trp Phe Ser Asp Gly
1               5                   10                  15

Cys Leu Phe Leu Gly Gly Ala Phe Ser Ala Leu Leu Leu Val Trp Gly
                20                  25                  30

Phe Trp Ser Phe Ile Ala Pro Ile Pro Ile Thr Asp Pro Asn Phe Asp
            35                  40                  45

Ser Val Ser Thr Lys Leu Lys Thr Leu Lys Asn Pro Arg Thr Val Pro
        50                  55                  60

Ser Thr Val Ile Cys Ser Thr Ser Ala Ala Glu Thr Thr Thr Val Pro
65                  70                  75                  80

Asn Leu Arg His Asp Pro Pro Glu Ala Thr Phe Tyr Asp Asp Pro Glu
                85                  90                  95

Thr Ser Tyr Thr Leu Asp Lys Pro Met Lys Asn Trp Asp Glu Lys Arg
            100                 105                 110

Gln Glu Trp Leu Asn Arg His Pro Ser Phe Ser Ala Gly Ala Lys Ser
        115                 120                 125

Arg Ile Leu Leu Val Thr Gly Ser Gln Pro Thr Pro Cys Lys Asn Pro
130                 135                 140

Ile Gly Asp His Leu Leu Leu Arg Phe Phe Lys Asn Lys Val Asp Tyr
145                 150                 155                 160

Cys Arg Leu His Gly Tyr Asp Ile Phe Tyr Asn Asn Ala Leu Leu Gln
                165                 170                 175

Pro Lys Met His Thr Tyr Trp Ala Lys Tyr Pro Val Val Arg Ala Ala
            180                 185                 190

Met Met Ala His Pro Glu Ala Glu Trp Ile Trp Trp Val Asp Ser Asp
        195                 200                 205

Ala Leu Phe Thr Asp Met Glu Phe Lys Leu Pro Leu Asn Arg Tyr Lys
    210                 215                 220

Asn His Asn Leu Ile Val His Gly Trp Pro Thr Leu Ile His Glu Ala
225                 230                 235                 240

Lys Ser Trp Thr Gly Leu Asn Ala Gly Val Phe Leu Ile Arg Asn Cys
                245                 250                 255

Gln Trp Ser Leu Asp Phe Met Asp Val Trp Ala Ser Met Gly Pro Gln
            260                 265                 270

Thr Pro Ser Tyr Glu Lys Trp Gly Glu Lys Leu Arg Thr Thr Phe Lys
        275                 280                 285
```

```
Asp Lys Ala Phe Pro Glu Ser Asp Asp Gln Thr Gly Leu Ala Tyr Leu
            290                 295                 300

Ile Ala Val Glu Lys Glu Lys Trp Ala Asp Arg Ile Tyr Leu Glu Ser
305                 310                 315                 320

Glu Tyr Tyr Phe Glu Gly Tyr Trp Lys Glu Ile Val Glu Thr Tyr Glu
                        325                 330                 335

Asn Ile Thr Asp Lys Tyr His Glu Val Glu Arg Lys Val Arg Ser Leu
                340                 345                 350

Arg Arg Arg His Ala Glu Lys Val Ser Glu Ser Tyr Gly Ala Val Arg
            355                 360                 365

Glu Pro Tyr Val Met Val Ala Gly Ser Gly Arg Gly Ser Trp Arg Arg
            370                 375                 380

Pro Phe Ile Thr His Phe Thr Gly Cys Gln Pro Cys Ser Gly Asn His
385                 390                 395                 400

Asn Ala Met Tyr Ser Pro Asp Ala Cys Trp Asn Gly Met Asn Lys Ala
                405                 410                 415

Leu Ile Phe Ala Asp Asn Gln Val Leu Arg Lys Phe Gly Tyr Val His
                    420                 425                 430

Pro Asp Leu Gln Asp Asn Ser Val Ser Pro Ile Pro Phe Asp Tyr Pro
            435                 440                 445

Ala

<210> SEQ ID NO 33
<211> LENGTH: 437
<212> TYPE: PRT
<213> ORGANISM: Lotus japonicus

<400> SEQUENCE: 33

Met Ala Arg Leu Gly Ser Arg Asn Lys Ser Ser Leu Trp Leu Ser Asp
1               5                   10                  15

Gly Cys Cys Phe Leu Thr Gly Ala Leu Ser Ala Leu Leu Leu Val Trp
                20                  25                  30

Gly Leu Cys Ser Phe Ile Ile Pro Phe Pro Asn Thr Asp Pro Lys Leu
            35                  40                  45

Asn Ser Val Ala Ala Lys Leu Lys Ser Leu Asn Leu Pro Arg Asn Gln
50                  55                  60

Ile Thr Thr Ser Ser Ala Gln Asp Leu Leu Tyr Asp Ser Pro Glu Thr
65                  70                  75                  80

Thr Phe Tyr Asp Asp Pro Glu Met Ser Tyr Thr Met Asp Lys Pro Val
                85                  90                  95

Thr Asn Trp Asp Glu Lys Arg Arg Gln Trp Leu Leu His His Pro Ser
                100                 105                 110

Phe Ala Ala Gly Ala Ser Asp Arg Ile Leu Leu Val Thr Gly Ser Gln
            115                 120                 125

Pro Lys Arg Cys His Asn Pro Ile Gly Asp His Leu Leu Leu Arg Phe
130                 135                 140

Phe Lys Asn Lys Val Asp Tyr Cys Arg Ile His Asp Ile Asp Ile Ile
145                 150                 155                 160

Tyr Asn Asn Ala Leu Leu His Pro Lys Met Asn Ser Tyr Trp Ala Lys
                165                 170                 175

Tyr Pro Val Val Lys Ala Ala Met Ile Ala His Pro Glu Val Glu Trp
            180                 185                 190

Ile Trp Trp Val Asp Ser Asp Ala Val Ile Thr Asp Met Glu Phe Lys
            195                 200                 205

Leu Pro Leu Asn Arg Tyr Asn Glu Phe Asn Leu Ile Ile His Gly Trp
```

```
                210                 215                 220
Glu Asp Leu Val Lys Lys His Ser Trp Thr Gly Leu Asn Ala Gly
225                 230                 235                 240

Val Phe Leu Met Arg Asn Cys Gln Trp Ser Leu Asp Phe Met Asp Val
                245                 250                 255

Trp Ala Ala Met Gly Pro Ser Ser Pro Asp Tyr Lys Lys Trp Gly Glu
                260                 265                 270

Lys Leu Met Ala Thr Phe Lys Asp Lys Val Ile Pro Asp Ser Asp Asp
                275                 280                 285

Gln Thr Ala Leu Ala Tyr Leu Ile Ala Met Gly Glu Asp Lys Trp Thr
290                 295                 300

Glu Lys Ile Tyr Leu Glu Lys Asp Tyr Phe Glu Gly Tyr Trp Val
305                 310                 315                 320

Glu Leu Ala Lys Met Tyr Glu Asn Val Ser Val Arg Tyr Asp Glu Val
                325                 330                 335

Glu Arg Arg Val Gly Gly Leu Arg Arg His Ala Glu Lys Val Ser
                340                 345                 350

Glu Arg Tyr Gly Glu Met Arg Glu Glu His Val Lys Tyr Phe Gly Gln
                355                 360                 365

Trp Arg Arg Pro Phe Ile Thr His Phe Thr Gly Cys Gln Pro Cys Asn
370                 375                 380

Gly His His Asn Pro Ala Tyr Ala Ala Asp Asp Cys Trp Asn Gly Met
385                 390                 395                 400

Asp Arg Ala Leu Asn Phe Ala Asp Asn Gln Val Leu Arg Thr Tyr Gly
                405                 410                 415

Tyr Val Arg Arg Ser Leu Asn Asp Lys Ala Val Thr Pro Ile Pro Tyr
                420                 425                 430

Asp Tyr Pro Ala Ala
                435

<210> SEQ ID NO 34
<211> LENGTH: 36
<212> TYPE: DNA
<213> ORGANISM: Artificial Sequence
<220> FEATURE:
<223> OTHER INFORMATION: primer or probe
<220> FEATURE:
<221> NAME/KEY: modified_base
<222> LOCATION: (24)..(25)
<223> OTHER INFORMATION: I
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (29)..(30)
<223> OTHER INFORMATION: I
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (34)..(35)
<223> OTHER INFORMATION: I
<220> FEATURE:
<221> NAME/KEY: misc_feature
<222> LOCATION: (34)..(35)
<223> OTHER INFORMATION: n is a, c, g, or t

<400> SEQUENCE: 34
ggccacgcgt cgactagtac gggnngggnn gggnng                                36
```

<210> SEQ ID NO 35
<211> LENGTH: 20
<212> TYPE: DNA
<213> ORGANISM: Artificial Sequence
<220> FEATURE:
<223> OTHER INFORMATION: primer or probe

<400> SEQUENCE: 35
ggccacgcgt cgactagtac                                               20

<210> SEQ ID NO 36
<211> LENGTH: 18
<212> TYPE: DNA
<213> ORGANISM: Artificial Sequence
<220> FEATURE:
<223> OTHER INFORMATION: primer or probe

<400> SEQUENCE: 36
gaacatgttg acgagcct                                                 18

<210> SEQ ID NO 37
<211> LENGTH: 24
<212> TYPE: DNA
<213> ORGANISM: Artificial Sequence
<220> FEATURE:
<223> OTHER INFORMATION: primer or probe

<400> SEQUENCE: 37
gcccgcagga cttcattcgt ggag                                          24

<210> SEQ ID NO 38
<211> LENGTH: 24
<212> TYPE: DNA
<213> ORGANISM: Artificial Sequence
<220> FEATURE:
<223> OTHER INFORMATION: primer or probe

<400> SEQUENCE: 38
atacttggta tatcgtttcc ttcc                                          24

<210> SEQ ID NO 39
<211> LENGTH: 21
<212> TYPE: DNA
<213> ORGANISM: Artificial Sequence
<220> FEATURE:
<223> OTHER INFORMATION: primer or probe

<400> SEQUENCE: 39
tgacacatcc aatcacatcg c                                             21

<210> SEQ ID NO 40
<211> LENGTH: 17
<212> TYPE: DNA
<213> ORGANISM: Artificial Sequence
<220> FEATURE:
<223> OTHER INFORMATION: primer or probe

<400> SEQUENCE: 40
ctgctcattg ccctcag                                                  17

<210> SEQ ID NO 41
<211> LENGTH: 19
<212> TYPE: DNA
<213> ORGANISM: Artificial Sequence
<220> FEATURE:
<223> OTHER INFORMATION: primer or probe

```
<400> SEQUENCE: 41
gacttgctgt actcgtcta                                          19

<210> SEQ ID NO 42
<211> LENGTH: 21
<212> TYPE: DNA
<213> ORGANISM: Artificial Sequence
<220> FEATURE:
<223> OTHER INFORMATION: primer or probe

<400> SEQUENCE: 42
aatgtcatgt ccctccatcg a                                       21

<210> SEQ ID NO 43
<211> LENGTH: 23
<212> TYPE: DNA
<213> ORGANISM: Artificial Sequence
<220> FEATURE:
<223> OTHER INFORMATION: primer or probe

<400> SEQUENCE: 43
aactcggctg gcttctaaaa gtc                                     23

<210> SEQ ID NO 44
<211> LENGTH: 15
<212> TYPE: DNA
<213> ORGANISM: Artificial Sequence
<220> FEATURE:
<223> OTHER INFORMATION: primer or probe
<220> FEATURE:
<221> NAME/KEY: modified_base
<222> LOCATION: (1)..(1)
<223> OTHER INFORMATION: FAM-modified
<220> FEATURE:
<221> NAME/KEY: modified_base
<222> LOCATION: (15)..(15)
<223> OTHER INFORMATION: MGB-modified

<400> SEQUENCE: 44
caaagcagca attat                                              15

<210> SEQ ID NO 45
<211> LENGTH: 21
<212> TYPE: DNA
<213> ORGANISM: Artificial Sequence
<220> FEATURE:
<223> OTHER INFORMATION: primer or probe

<400> SEQUENCE: 45
gaacaggccc atcccttatt g                                       21

<210> SEQ ID NO 46
<211> LENGTH: 17
<212> TYPE: DNA
<213> ORGANISM: Artificial Sequence
<220> FEATURE:
<223> OTHER INFORMATION: primer or probe

<400> SEQUENCE: 46
cggcgcttgg cattgta                                            17

<210> SEQ ID NO 47
<211> LENGTH: 21
<212> TYPE: DNA
<213> ORGANISM: Artificial Sequence
<220> FEATURE:
<223> OTHER INFORMATION: primer or probe
<220> FEATURE:
```

```
<221> NAME/KEY: modified_base
<222> LOCATION: (1)..(1)
<223> OTHER INFORMATION: VIC-modified
<220> FEATURE:
<221> NAME/KEY: modified_base
<222> LOCATION: (21)..(21)
<223> OTHER INFORMATION: MGB-modified

<400> SEQUENCE: 47
tgacacatcc aatcacatcg c                                              21

<210> SEQ ID NO 48
<211> LENGTH: 36
<212> TYPE: DNA
<213> ORGANISM: Artificial Sequence
<220> FEATURE:
<223> OTHER INFORMATION: primer or probe
<220> FEATURE:
<221> NAME/KEY: modified_base
<222> LOCATION: (24)..(25)
<223> OTHER INFORMATION: I
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (29)..(30)
<223> OTHER INFORMATION: I
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (34)..(35)
<223> OTHER INFORMATION: I
<220> FEATURE:
<221> NAME/KEY: misc_feature
<222> LOCATION: (34)..(35)
<223> OTHER INFORMATION: n is a, c, g, or t

<400> SEQUENCE: 48
ggccacgcgt cgactagtac gggnngggnn gggnng                              36

<210> SEQ ID NO 49
<211> LENGTH: 20
<212> TYPE: DNA
<213> ORGANISM: Artificial Sequence
<220> FEATURE:
<223> OTHER INFORMATION: primer or probe

<400> SEQUENCE: 49
ggccacgcgt cgactagtac                                                20

<210> SEQ ID NO 50
<211> LENGTH: 23
<212> TYPE: DNA
<213> ORGANISM: Artificial Sequence
<220> FEATURE:
<223> OTHER INFORMATION: primer or probe

<400> SEQUENCE: 50
ctcccatacc cagcgtcctt aag                                            23

<210> SEQ ID NO 51
<211> LENGTH: 18
<212> TYPE: DNA
<213> ORGANISM: Artificial Sequence
<220> FEATURE:
<223> OTHER INFORMATION: primer or probe
```

```
<400> SEQUENCE: 51
ttctccagcg tccccacg                                              18

<210> SEQ ID NO 52
<211> LENGTH: 19
<212> TYPE: DNA
<213> ORGANISM: Artificial Sequence
<220> FEATURE:
<223> OTHER INFORMATION: primer or probe

<400> SEQUENCE: 52
agacagcagc caccatgcc                                             19

<210> SEQ ID NO 53
<211> LENGTH: 24
<212> TYPE: DNA
<213> ORGANISM: Artificial Sequence
<220> FEATURE:
<223> OTHER INFORMATION: primer or probe

<400> SEQUENCE: 53
ccccgacttt taacttacaa caga                                       24

<210> SEQ ID NO 54
<211> LENGTH: 21
<212> TYPE: DNA
<213> ORGANISM: Artificial Sequence
<220> FEATURE:
<223> OTHER INFORMATION: primer or probe

<400> SEQUENCE: 54
gaacaggccc atcccttatt g                                          21

<210> SEQ ID NO 55
<211> LENGTH: 17
<212> TYPE: DNA
<213> ORGANISM: Artificial Sequence
<220> FEATURE:
<223> OTHER INFORMATION: primer or probe

<400> SEQUENCE: 55
cggcgcttgg cattgta                                               17

<210> SEQ ID NO 56
<211> LENGTH: 16
<212> TYPE: DNA
<213> ORGANISM: Artificial Sequence
<220> FEATURE:
<223> OTHER INFORMATION: primer or probe

<400> SEQUENCE: 56
atgcgcactg acaaca                                                16

<210> SEQ ID NO 57
<211> LENGTH: 16
<212> TYPE: DNA
<213> ORGANISM: Artificial Sequence
<220> FEATURE:
<223> OTHER INFORMATION: primer or probe

<400> SEQUENCE: 57
cgcctctgcc gttcga                                                16

<210> SEQ ID NO 58
<211> LENGTH: 21
<212> TYPE: DNA
```

```
<213> ORGANISM: Artificial Sequence
<220> FEATURE:
<223> OTHER INFORMATION: primer or probe

<400> SEQUENCE: 58
atttctagga agcgcctcca a                                              21

<210> SEQ ID NO 59
<211> LENGTH: 15
<212> TYPE: DNA
<213> ORGANISM: Artificial Sequence
<220> FEATURE:
<223> OTHER INFORMATION: primer or probe

<400> SEQUENCE: 59
ccagcatcgg acctt                                                     15
```

NUCLEIC ACIDS AND PROTEINS ASSOCIATED WITH GALACTOMANNAN SYNTHESIS IN COFFEE

This is a U.S. National Phase of International Application No. PCT/US2006/040556, filed Oct. 16, 2006, which claims benefit of U.S. Provisional Application No. 60/726,602, filed Oct. 14, 2005, the entire contents of each of which are incorporated by reference herein.

FIELD OF THE INVENTION

The present invention relates to the field of agricultural biotechnology. More particularly, the invention relates to enzymes from coffee plants that participate in polysaccharide metabolism, including galactomannan synthesis, and the nucleic acid sequences that encode the same.

BACKGROUND OF THE INVENTION

Various publications, including patents, published applications and scholarly articles, are cited throughout the present specification. The entire contents of each of these publications are incorporated herein, in their entireties. Citations not fully set forth within the specification may be found at the end of the specification.

A key step in coffee processing is the roasting of the green grain. The roasting step is usually carried out in the range of 170° to 230° C. for 5 to 15 minutes and it is responsible for generating most of the aroma, flavor, and color associated with the coffee beverage (Yeretzian, et al., 2005). Depending on the degree of roasting, from 12-40% of the polysaccharides can be degraded at this step (Redgwell, et al., 2002). The roasting step has been reported to alter the length of many of the complex polysaccharide polymers, which can increase their solubility (Redgwell, et al., 2002). Fragmentation of the coffee polysaccarides is thought to favourably affect beverage organoleptic properties such as mouthfeel (Illy and Viani 1995) and foam stability (Nunes, et al., 1997). Breakdown of the polysaccharides is also thought to influence the binding of volatile aroma compounds indirectly because some complex carbohydrate degradation products participate in the formation of the roasted grain melanoidins, a class of poorly defined compounds that constitute over 20% of the roasted grain dry weight (Charles-Bernard, et al., 2005). The roasting induced cleavage of the polysaccharides may also produce an increase in the amount of solids extracted from the coffee grain, a property of critical importance for the production of soluble coffee. Additionally, the fragmentation/degradation of the carbohydrates in the coffee grain also contribute to the generation of an important group of coffee flavor and aroma molecules via the Maillard reaction associated with coffee roasting (Yeretzian, et al, 2005).

Carbohydrates make up a large proportion of the mature green coffee grain (green bean). Approximately 48-55% of the dry weight in arabica (*Coffea arabica*) and robusta (*C. canephora*) green grain is composed of carbohydrate, some of which is in the form of complex polysacchaccarides, while other forms include free mono- and di-saccharides (Clifford M. N., 1985 In Coffee: Botany, Biochemistry, and Production, pp 374, ed. Clifford, M. and Willson, K., Croom Melm Ltd, London; Fischer, et al. 2001, Carbohydrate Research, 330, 93-101). Three main types of complex carbohydrate-based polymers have been identified in the coffee grain. The most abundant grain polysaccharides are the galactomannans, which are reported to represent up to 25% of the mass in the mature green coffee grain, i.e., approximately 50% of the grain carbohydrates. (Oosterveld et al., 2003 Carbohydrate Polymers 52, 285-2960). The next most abundant group of polysaccharides are the arabinogalactans which comprise up to 35% of the green grain polysaccharides (Oosterveld et al., 2003, supra). The remaining approximately 16% of the Arabica green grain polysaccharides consist primarily of cellulose and xyloglucans (Oosterveld et al., 2003)

Mannan containing hemicelluloses are composed of a backbone of beta 1-4 linked mannose molecules, and although they can be widely found in plants the mannans have been considered to be a relatively minor constituent in the walls of most plant cell types (Bacic, Harris, and Stone 1988; Fry 2004; Somerville, et al., 2004b). Some endosperm containing seeds, such as those of Leguminosae, Palmae, and the commercially important *Coffea* species, have quite large amounts of galactomannans in the seed endosperm cell walls (Matheson 1990; Buckeridge, et. al., 2000; Pettolino, et al., 2001; Redgwell, et al., 2002; Hanford, et al., 2003). Galactomannans are characterized by mannan chains that have single galactosyl molecules attached by a (1-6) alpha linkage. The galactomannans of the seed endosperm appear to be associated with the secondary cell wall thickening of the endosperm cell wall (Pettolino, et al., 2001; Sunderland, et al., 2004; Somerville, et al., 2004a) and are believed to form part of the energy reserve of the mature seed, which is analogous to role played by starch in cereal endosperms (Reid 1985). Other functions that have been theorized for the endosperm galactomannans include facilitating imbibition/germination and the protection of the seed embryo from dessication (Reid and Bewley 1979). Other main mannan based cell wall polymers include the glucomannans which have some of the mannose units substituted by beta-1,4-linked glucose residues, and the galactoglucomannans which are glucomannans with alpha-1,6-linked galactose residues. Galactoglucomannans with low levels of galactose are important constituents of thickened lignified secondary cell walls of gymnosperms (Lundqvist, J., et al., 2002) and have also been found in kiwi fruit (*Actinidia deliciosa*) and tissue cultured tobacco (*Nicotiana plumbaginifolia*) cells (Schroder, R., et al., 2001; Sims, I., et al., 1997). Recently studies have purported that mannan polymers exist in the thickened secondary cell walls of xylem elements, xylem parenchyma and interfasicular fibers of the model angiosperm *Arabidopsis thaliana* (Handford et al 2003). They also detected significant levels of mannans in the thickened epidermal cell walls of leaves and stem, and lower levels of mannans in most other tissues examined indicating the widespread presence of mannans in arabidopsis.

While the cellulose polymers are known to be synthesized at the plasma membrane, most non-cellulosic polysaccharides are believed to be made in the golgi apparatus and then transported outside the cell membrane into the apoplastic space (Keegstra and Raikhel 2001; Somerville, Bauer, Brininstool, Facette, Hamann, Milne, Osborne, Paredez, Persson, Raab, Vorwerk, and Youngs 2005; Liepman, Wilkerson, and Keegstra 2005b). Two membrane bound glycosyltransferases are known to be involved in synthesizing the galactomannans: a Mg++0 dependant, GDP-Man dependant (1,4)-beta-D-mannosyltransferase or mannan synthase (MS) and a Mn++ dependant, UDP-Gal dependant mannan specific (1,6)-alpha-D-galactosyltransferase (GMGT), and these enzymes are believed to work together very closely to determine the statistical distribution of galactosyl residues along the mannan polymer (Edwards, Choo, Dickson, Scott, Gridley, and Reid 2004). Confirmation that mannans are synthesized in the golgi apparatus has recently been obtained by using mannan specific antibodies to detect mannan synthesis in vitro, and this further supports the overall model in which the hemicellulose type polysaccharides such as the galactomannans are made in the golgi and then transported to the cell membrane and secreted into the apoplast region (Handford, Baldwin, Goubet, Prime, Miles, Yu, and Dupree 2003; Somerville, Bauer, Brininstool, Facette, Hamann, Milne, Osborne, Paredez, Persson, Raab, Vorwerk, and Youngs 2005). The importance of a golgi bound GMGT protein in the synthesis of seed endosperm galactomannans, and more precisely in controlling the level of galactose modification, has recently been demonstrated by showing that either over-, or under-expressing the *Lotus japonicus* GMGT protein causes predicable changes in the galactose/mannose ratios in the seed (Edwards, Choo, Dickson, Scott, Gridley, and Reid 2004).

Until recently, the genes responsible for the synthesis of the plant cell mannans were not known. The first gene isolated that encodes a biochemically demonstrated mannan synthase was the ManS from *Cyamopsis tetragonoloba* (guar) seeds (Dhugga, et al., 2004). The cDNA for CtManS was isolated from EST libraries made from three different seed developmental stages of guar, a seed which makes very large quantities of galactomannans. The CtManS related ESTs were identified by searching for sequences with strong similarities to plant CelA (cellulose synthases generating beta-1,3-glucans) and Csl (cellulose synthase-like proteins). The Csl genes have significant similarity to the CelA genes, and have been previously proposed as candidate genes for enzymes involved in the synthesis of hemicelluoses like galactomannans (Cutler and Somerville 1997; Richmond and Somerville 2000; Hazen, et al., 2002). The abundance of the candidate mannan synthase ESTs in each guar seed library corresponded to the levels of mannan synthase activity biochemically measured at each stage, suggesting these ESTs represented a mannan synthase. The putative guar mannan synthase cDNA was shown to encode a functional enzyme by showing that soybean somatic embryos, which normally have no detectable mannan synthase activity, exhibited significant mannan synthase activity when they over-express the CtManS cDNA sequence (Dhugga, et al., 2004). The functional recombinant enzyme was found to be located in the golgi apparatus. In the arabidopsis genome, there are over 25 genes annoted as Csl genes and these are subdivided into families based on their sequence homologies. Recently, a functional evaluation has been carried out on recombinant proteins generated from a number of the arabidopsis Csl gene sequences and it was determined that several members of the CslA gene family encoded proteins with beta-mannan synthase activity (Liepman, et al., 2005).

There is little information available directed to the metabolism of mannan related polymers in coffee. Several highly related cDNA encoding an alpha-galalactosidase found in coffee grain have been obtained and the expression of this gene in developing grain indicates that this gene is induced during the formation and expansion of the endosperm (approximately 22-27 WAF (Weeks After Fertilization) and expression can also be detected in leaves, flowers, zygotic embryos, and weakly in roots (Marraccini, et al., 2005). The galactose/mannose ratio of the coffee grain galactomannans falls from a ratio of approximately 1:2 to 1:7 at an early stage of grain development (11 WAF; weeks after fertilization) to a ratio of 1:7 to 1:40 near maturity at 31 WAF (Redgwell, et al., 2003). This information, together with the developmental expression data for the alpha-galactosidase presented above, led to the theory that this particular alph-galactosidase gene product could be directly involved in lowering the galactose content of the coffee grain galactomannans that begin around 21-26 WAF and continues to grain maturity (Redgwell, et al., 2003). Support for this model was found in the developing seeds of senna (*Senna occidentalis*) where a significant increase in alpha-galactosidase activity was found to coincide with the reduction of the galactose content of seed galactomannans (Edwards, et al., 1992). Further support for the involvement of an alpha-galactosidase in the reduction of the galactose content was subsequently obtained when the senna alpha-galactosidase was expressed in developing *Cyamopsis tetragonoloba* (guar) seeds with the aid of a seed specific promoter (Joersbo, et al., 2001). Guar seeds normally have high levels of galactomannans that possess a very high galactose/mannan ratio, but guar seeds produced from the plants expressing senna alpha-galactosidase showed significant reductions in the level of galactose/mannose ratio in the modified guar seeds. Two cDNA encoding distinct endo-beta mannanases (manA and manB) have also been isolated from germinating coffee grain (Marraccini, et al., 2001). The corresponding genes were not expressed in the developing grain, but both were expressed during germination, with transcripts being detected starting at 10-15 days after imbibition. This observation suggests that both of these mananases are associated with the degradation of galactomannans during germination and result in the liberation of free sugars that then act as both a source of energy and reduced carbon for the germinating seed. The expression of manA was examined and no expression was detected in leaves, somatic embryos, flower buds or roots (Marraccini, et al., 2001).

Despite the abundance of galactomannans in coffee grain and the implicit importance of enzymes that participate in galactomannan synthesis, little information is available on these genes in coffee. Thus, there is a need to identify, isolate and characterize the enzymes, genes, and genetic regulatory elements involved in the galactomannan biosynthetic pathway in coffee. Such information will enable galactomannan synthesis to be genetically manipulated, with the goal of imparting desirable phenotypic advantages associated with altered galactomannan production.

SUMMARY OF THE INVENTION

One aspect of the invention features a nucleic acid molecule isolated from *Coffea* spp. comprising a coding sequence that encodes a galactomannan synthesis enzyme, which can be a galactosyltransferase or a mannan synthase. In certain embodiments, the mannan synthase comprises a conserved domain having amino acid sequence QHRWS. In other embodiments, the mannan synthase comprises an amino acid sequence greater than about 75% identical to that of any one of SEQ ID NOS: 4-6, and preferably comprises any one of SEQ ID NOS: 4-6. Specifically, the coding sequence comprises SEQ ID NO:2 or SEQ ID NO:3.

In other embodiments, the enzyme is a galactosyltransferase that has at least about 54% amino acid sequence identity with a fenugreek galactosyltransferase or a *Lotus japonicus* galactosyltransferase. In other embodiments, the galactosyltransferase comprises an amino acid sequence greater than about 75% identical to any one of SEQ ID NOS: 15-18, and preferably comprises any one of SEQ ID NOS: 15-18. Specifically, the coding sequence comprises any one of SEQ ID NOS: 11-14.

In certain embodiments, the coding sequence is an open reading frame of a gene, or an mRNA molecule produced by transcription of a gene, or a cDNA molecule produced by reverse transcription of the mRNA molecule.

Another aspect of the invention features an oligonucleotide between 8 and 100 bases in length, which is complementary to a segment of the aforementioned nucleic acid molecule.

Another aspect of the invention features a vector comprising the coding sequence of the nucleic acid molecule described above. The vector can be an expression vector selected from plasmid, phagemid, cosmid, baculovirus, bacmid, bacterial, yeast and viral vectors. In certain embodiments, the coding sequence of the nucleic acid molecule is operably linked to a constitutive promoter. Alternatively, it is operably linked to an inducible promoter. In another alternative, the coding sequence of the nucleic acid molecule is operably linked to a tissue specific promoter, which may a seed specific promoter in certain embodiments, and more particularly a coffee seed-specific promoter.

Another aspect of the invention features a host cell transformed with the aforementioned vector. The host cell can be selected from plant cells, bacterial cells, fungal cells, insect cells and mammalian cells. A fertile plant produced from a transformed plant cell is also provided.

Another aspect of the invention features a method of modulating extractability of solids from coffee beans, comprising modulating production or activity of galactomannan synthesis enzyme within coffee seeds. Specifically, the enzymes are galactosyltransferase or mannan synthase, or a combination thereof. In one embodiment, production or activity of the galactomannan synthesis enzyme is increased, e.g., by increasing expression of a gene encoding the enzyme, or by introducing a transgene encoding the enzyme. In another embodiment, production or activity of the galactomannan synthesis enzyme is decreased, e.g., by interfering with expression of a gene encoding the enzyme.

Other features and advantages of the invention will be understood by reference to the drawings, detailed description and examples that follow.

Figure 1:
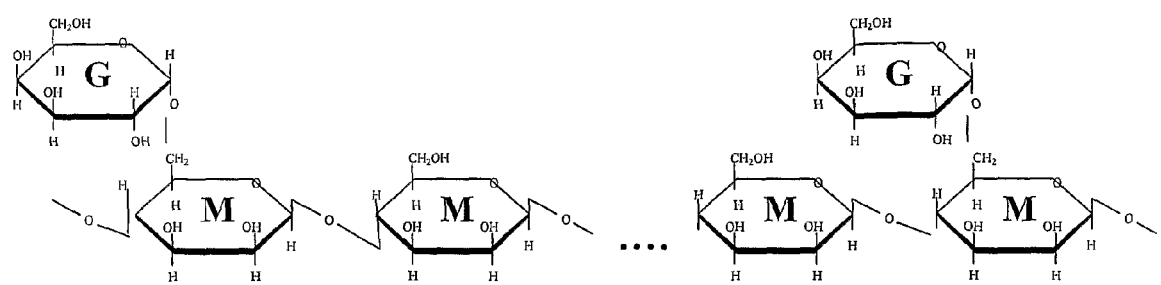
FIG. 1. Illustration of the structure of galactomannan polymer.

(A) Overview of the clones used to identify the complete ORF sequence for the *C. canephora* mannan synthase-encoding CcManS and the *C. arabica*-encoding mannan synthase CaManS. Four partial cDNA clones were obtained that covered the complete ORF of CcManS (see Examples): two 5' RACE products, pVC2 and pVC3 which contain the 5' end coding sequence of CcManS, and two partial cDNA clones (pcccs46w24c19 and pcccs46w16i11), which contain the remaining 3' end of CcManS. The cDNA clones pVC4, pVC6 and pVC7 contain PCR amplified sequences that contain the complete open reading frames encoding the coffee mannan synthase (Note: pVC4 contains a stop codon at 1118 bp due to an error introduced during the PCR amplification step, as discussed in the examples). Notations are as follows: pcccs46w16i11=insert sequences of cDNA clone cccs46w16i11 (with two introns and 3' end non coding sequences in the clone removed) from *Coffea canephora* (SEQ ID NO:7); pcccs46w24c19=insert sequences of cDNA clone cccs46w24c19 from *Coffea canephora* (SEQ ID NO:8); pVC2 (SEQ ID NO:9)=first RACE fragment *Coffea canephora*, var. *Robusta* (BP409), cloned into pCR-4-Topo; pVC3 (SEQ ID NO:10)=second RACE fragment, cloned into pCR-4-Topo; pVC4 (SEQ ID NO:1)=full length amplification of mannan synthase encoding polynucleotide from *Coffea canephora*, var. *Robusta* (BP409), cloned into pCR-4-Topo (this fragment has a stop codon in ORF); pVC6 (SEQ ID NO:2) =full length amplification of CcManS, a mannan synthase-encoding polynucleotide from *Coffea canephora*, var. *Robusta* (BP409), cloned into pCR-4-Topo; pVC7 (SEQ ID NO:3)=full length amplification of CaManS, a mannan synthase-encoding polynucleotide from *Coffea arabica*, var. *Arabica* (T2308), cloned into pCR-4-Topo.

(B-E) Alignment of all sequences for CcManS (SEQ ID NO:1 and SEQ ID NO:2) and CaManS (SEQ ID NO:3) performed using the CLUSTALW program (Lasergene package, DNASTAR) and manually optimized. The circled nucleotide in the pVC4 sequence marked the mutated base leading to the stop codon in the ORF of this clone. However, it is clear that the other three cDNA sequences encoding this region, all of which are from independent PCR reactions, have an A instead of a T at this position leading to the expected protein. Therefore, we believe this T in pVC4 is due to a PCR or cloning anomaly. Sequences in gray match pVC6. Intron sequences are noted by the presence of a black line above these sequences. A deletion in the pVC3 sequence at position 325 induces a change in the open reading frame and is believed to be an error generated during the RT-PCR cloning of this sequence.

FIG. 3. Shows the complete protein sequence of CcManS from *Coffea canephora* (SEQ ID NO:5) This protein sequence was deduced from the cDNA sequence encoded by pVC6 (SEQ ID NO:2).

FIG. 4. Protein sequence alignment of coffee mannan synthase sequences with other mannan synthase sequences. The protein sequences of CcManS (SEQ ID NO: 5) deduced from the pVC4 and pVC6 sequences and the protein sequence of CaManS (SEQ ID NO: 6) deduced from the pVC7 sequence were aligned with other plant mannan synthase proteins available in the NCBI database using CLUSTALW, followed by a manual optimization step (Note: the stop codon in pVC4 at position 345 is marked by a red circle). Regions reported to be conserved in β-glycosyltransferases are either marked by an * or are boxed (as in Dhugga et al. 2004). Amino acids marked in gray match represent the most frequently found amino acid found at that position. Accession numbers for the sequences used are the biochemically characterized CtManS (*Cyamopsis tetragonoloba*, AAR23313, SEQ ID NO:21), AtManS (*Arabidpsis thaliana*, CAB82941, SEQ ID NO:22), and IbManS (*Ipomoea trifida*, AAQ62572; SEQ ID NO:23).

Figure 5:
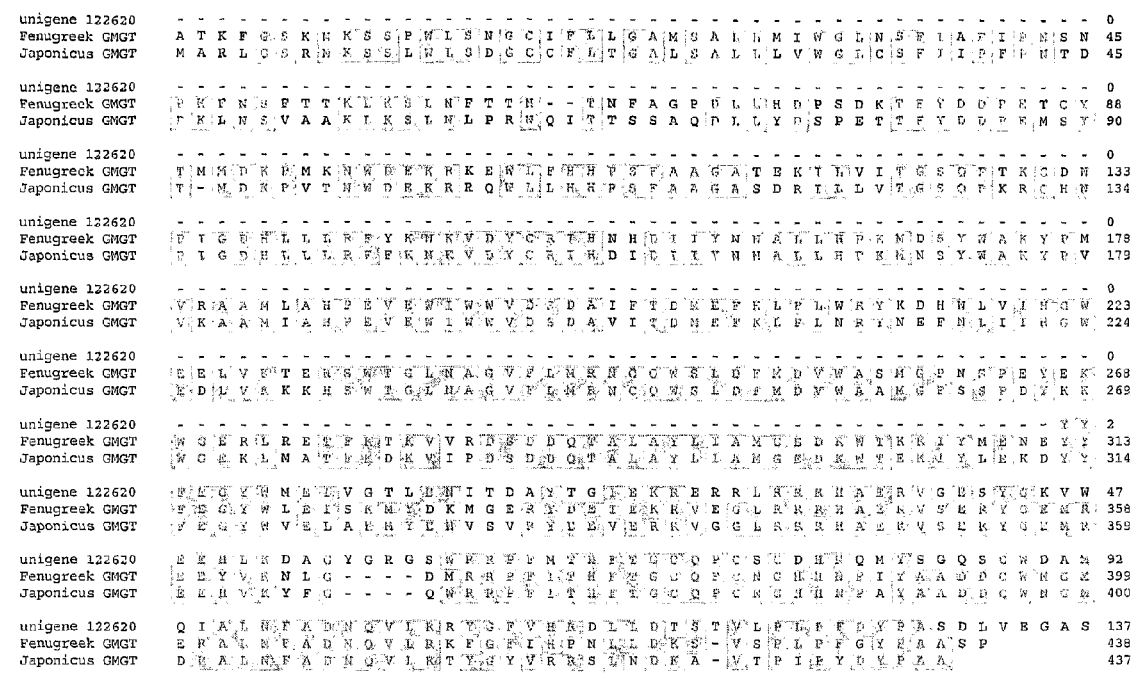

FIG. 5. Shows the sequence alignment of the protein sequence (SEQ ID NO:15) of unigene 122620 (SEQ ID NO:11) with two biochemically characterized plant GMGT sequences. The partial ORF of unigene 122620 (CcGMGT1) was aligned with the protein sequences of the *Lotus japonicus* GMGT (accession number AJ567668, SEQ ID NO: 24) and fenugreek (*Trigonella foenum-graecum*) GMGT (accession number AJ245478, SEQ ID NO: 25; noted to be a partial cDNA) using ClustalW. Amino acids found in two or more sequences are in grey.

FIG. 6. Shows the sequence alignment of the protein sequence (SEQ ID NO: 16) of unigene 122567 (SEQ ID NO:12) with two biochemically characterized plant GMGT sequences. The partial ORF of unigene 122567 (CcGMGT2) was aligned with the protein sequences of the *Lotus japonicus* GMGT (accession number AJ567668, SEQ ID NO: 24) and fenugreek (*Trigonella foenum-graecum*) GMGT (accession number AJ245478, SEQ ID NO:25); noted to be a partial cDNA) using ClustalW. Amino acids found in two or more sequences are in grey.

Figure 7:
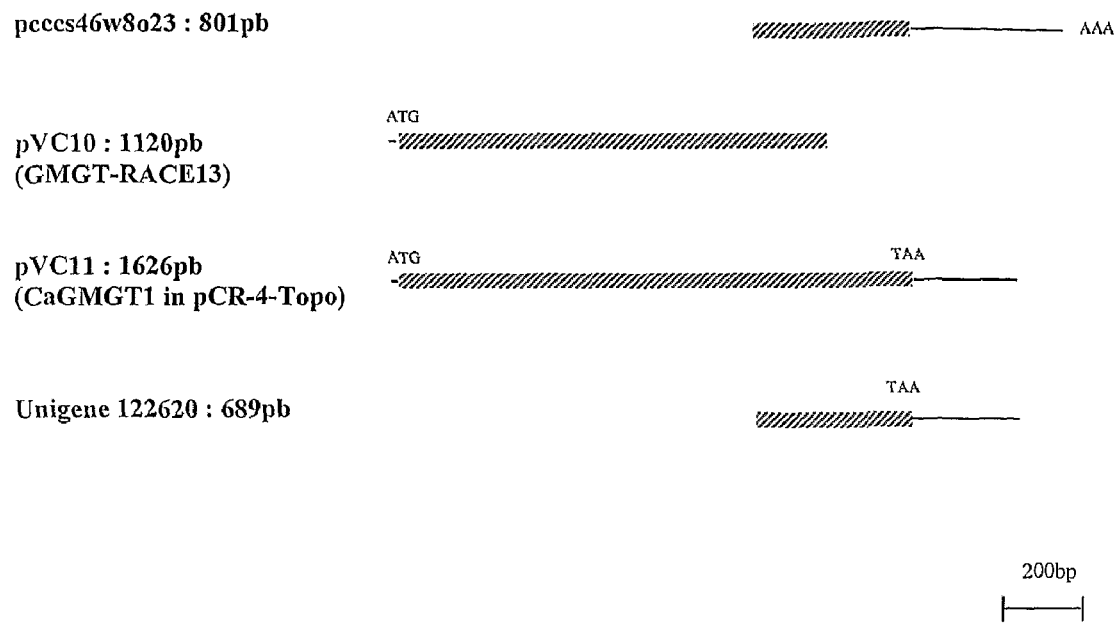

FIG. 7. Schematic representation of the three clones encoding partial or complete ORF sequence data for the coffee GMGTase 1. pcccs46w8o23 (SEQ ID NO:19) is a *C. canephora* EST library clone, pVC10 (SEQ ID NO:20) contains the isolated 5' RACE sequence, and pVC11 (SEQ ID NO: 13)

contains the arabica genomic fragment containing the complete polypeptide sequence of an arabica GMGTase 1.

Figure 8:
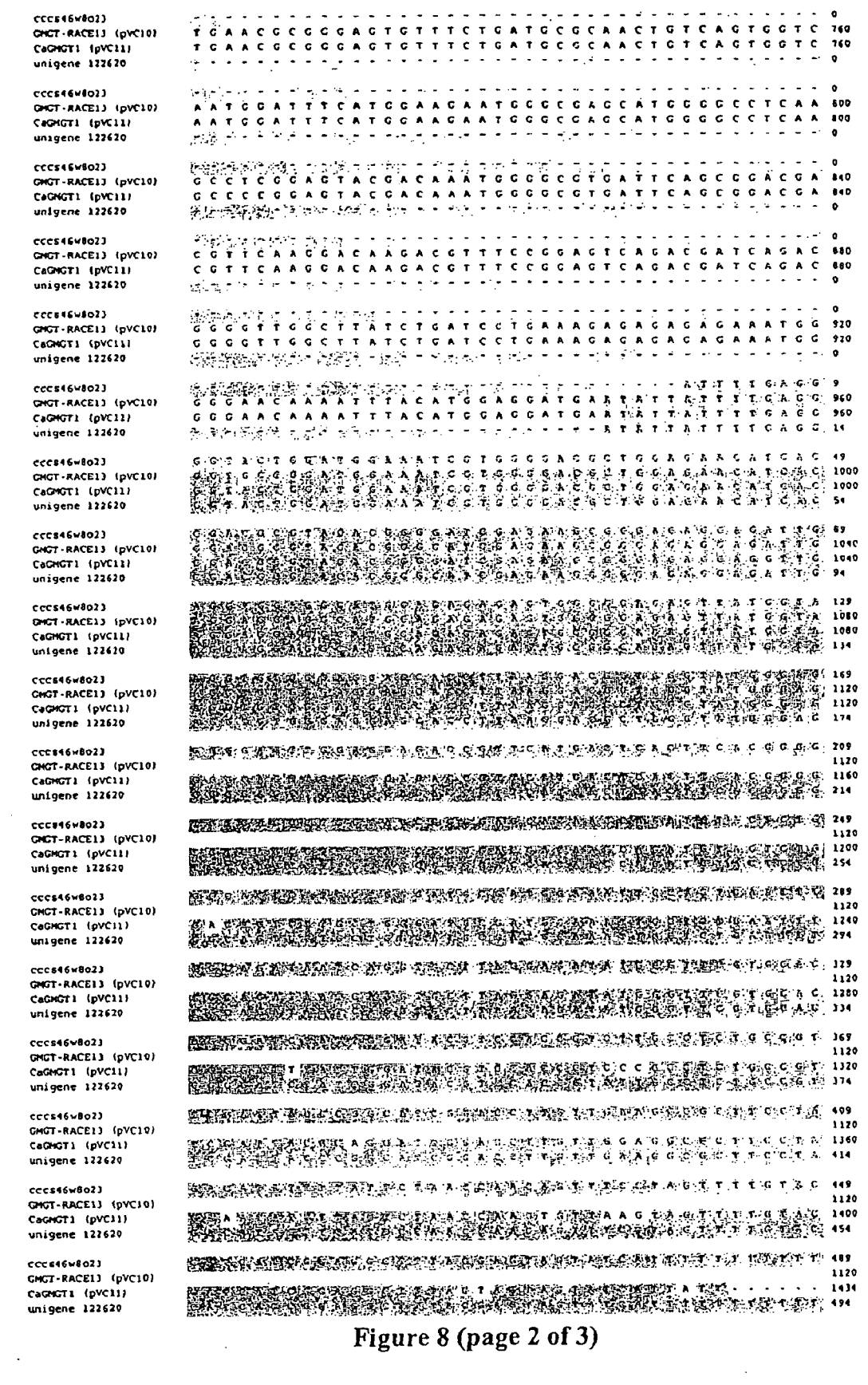
Figure 8:
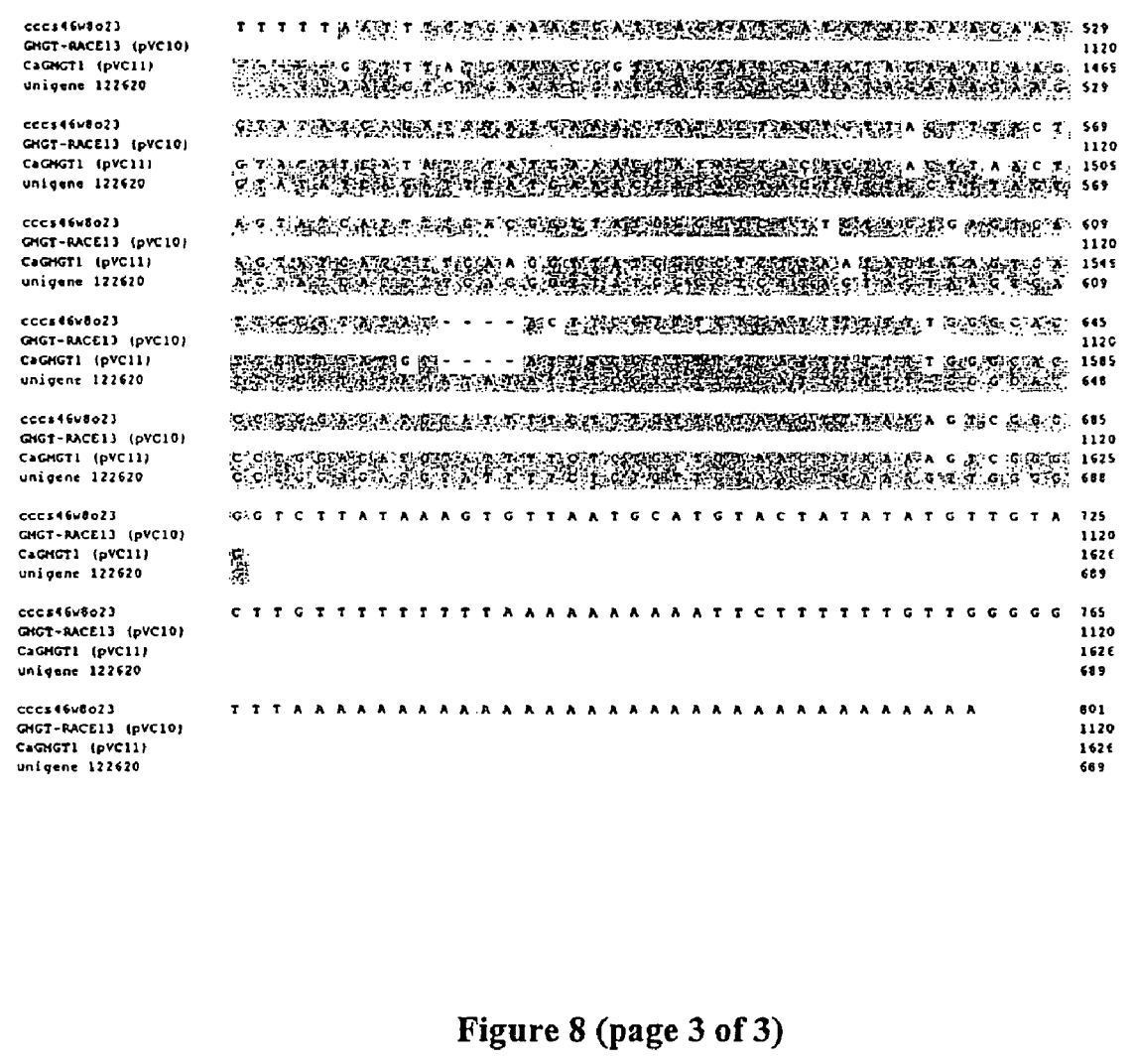

FIG. 8. Alignment of the GMGTase 1 DNA sequences of pcccs46w8o23 (SEQ ID NO:19), pVC10 (SEQ ID NO:20), and pVC11 (SEQ ID NO:13) with the "in-silico" generated sequence of unigene #122620 (SEQ ID NO:11). The alignment was made using CLUSTALW and manually adjusted.

Figure 9:
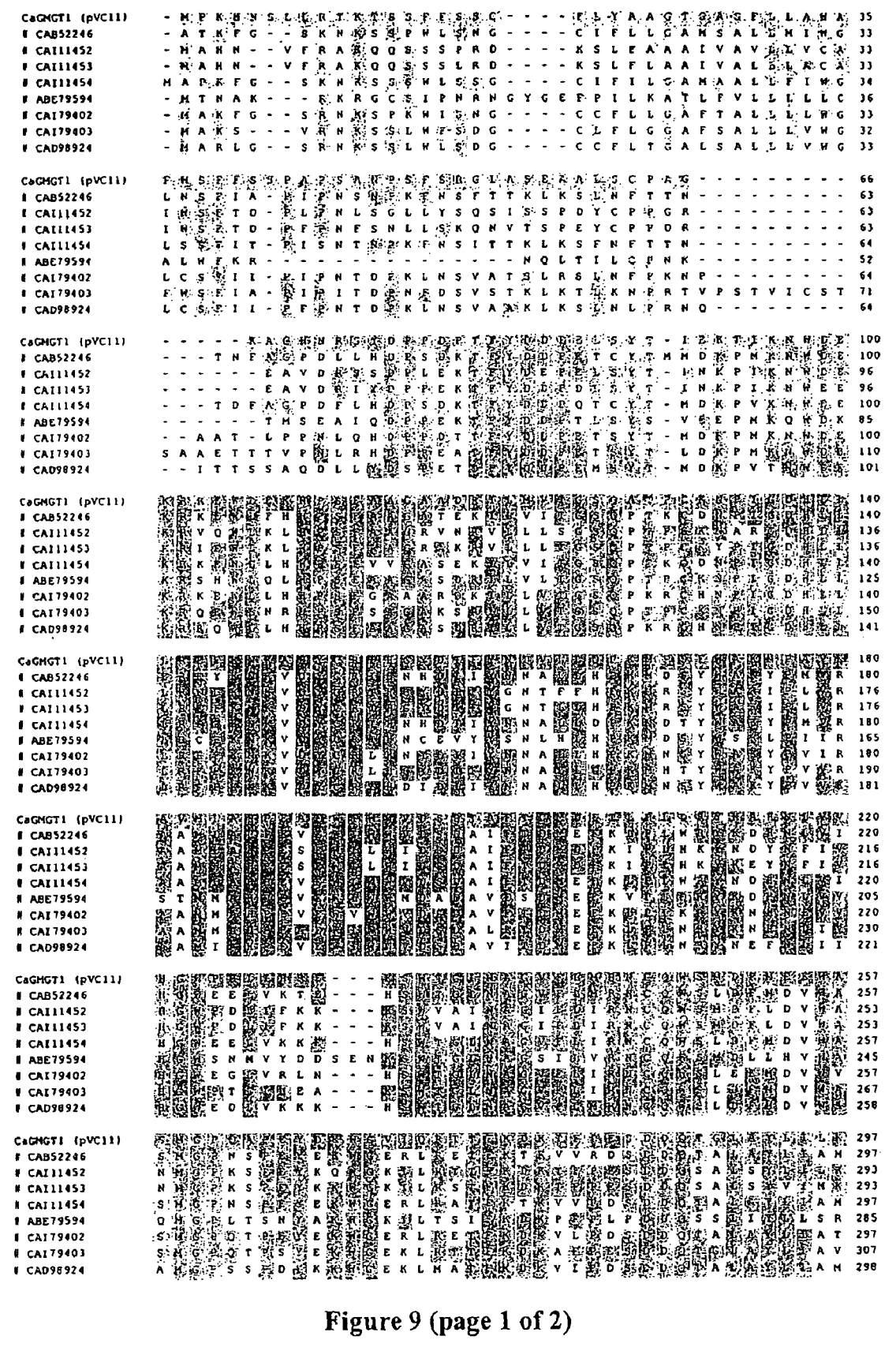

FIG. 9. Alignment of the protein sequence of CaGMGTase 1 (SEQ ID NO:17) with the most homologous protein sequences found in the GenBank public database. The alignment was made using CLUSTALW. Accession numbers: CAB52246: [*Trigonella foenum-graecum*] Alpha galactosyltransferase (SEQ ID NO:26); CAI11452: [*Solanum tuberosum*] Alpha-6-galactosyltransferase (SEQ ID NO:27); CAI11453: [*Nicotiana benthamiana*] Alpha-6-galactosyltransferase (SEQ ID NO:28); CAI11454: [*Medicago truncatula*] Alpha-6-galactosyltransferase (SEQ ID NO:29); ABE79594: [*Medicago truncatula*] Galactosyl transferase (SEQ ID NO:30); CAI79402: [*Cyamopsis tetragonoloba*] Galactomannan galactosyltransferase (SEQ ID NO:31); CAI79403: [*Senna occidentalis*] Galactomannan galactosyltransferase (SEQ ID NO:32); CAD98924: [*Lotus corniculatus* var. *japonicus*] Galactomannan galactosyltransferase (SEQ ID NO:33).

Figure 10:
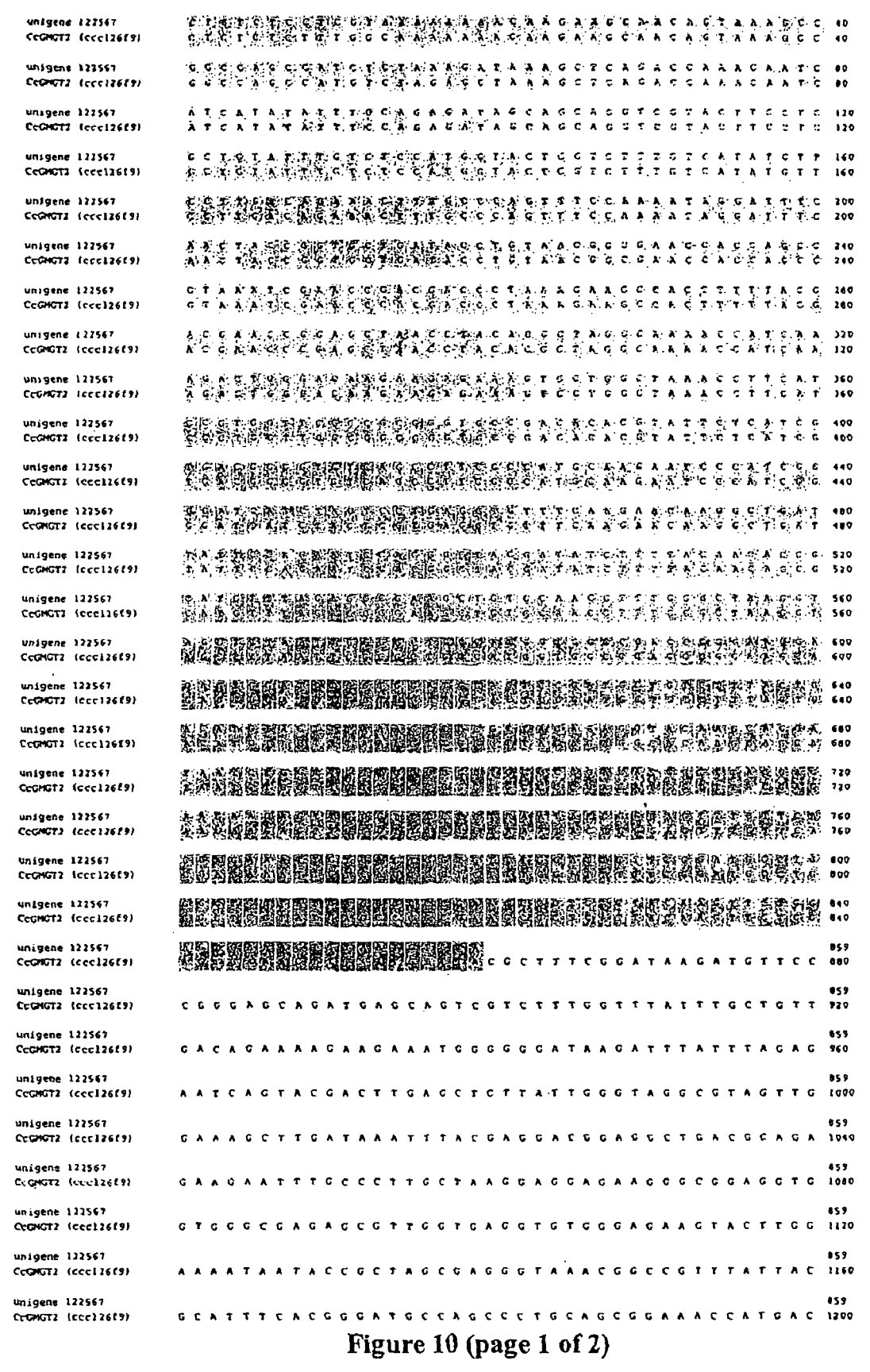

FIG. 10. Alignment of the GMGTase 2 DNA sequences of unigene #122567 (SEQ ID NO: 12 with the DNA sequence of *C. canephora* GMGTase 2 cDNA clone pccc126f9 (CcGMGTase 2; SEQ ID NO:14) using CLUSTALW.

Figure 11:
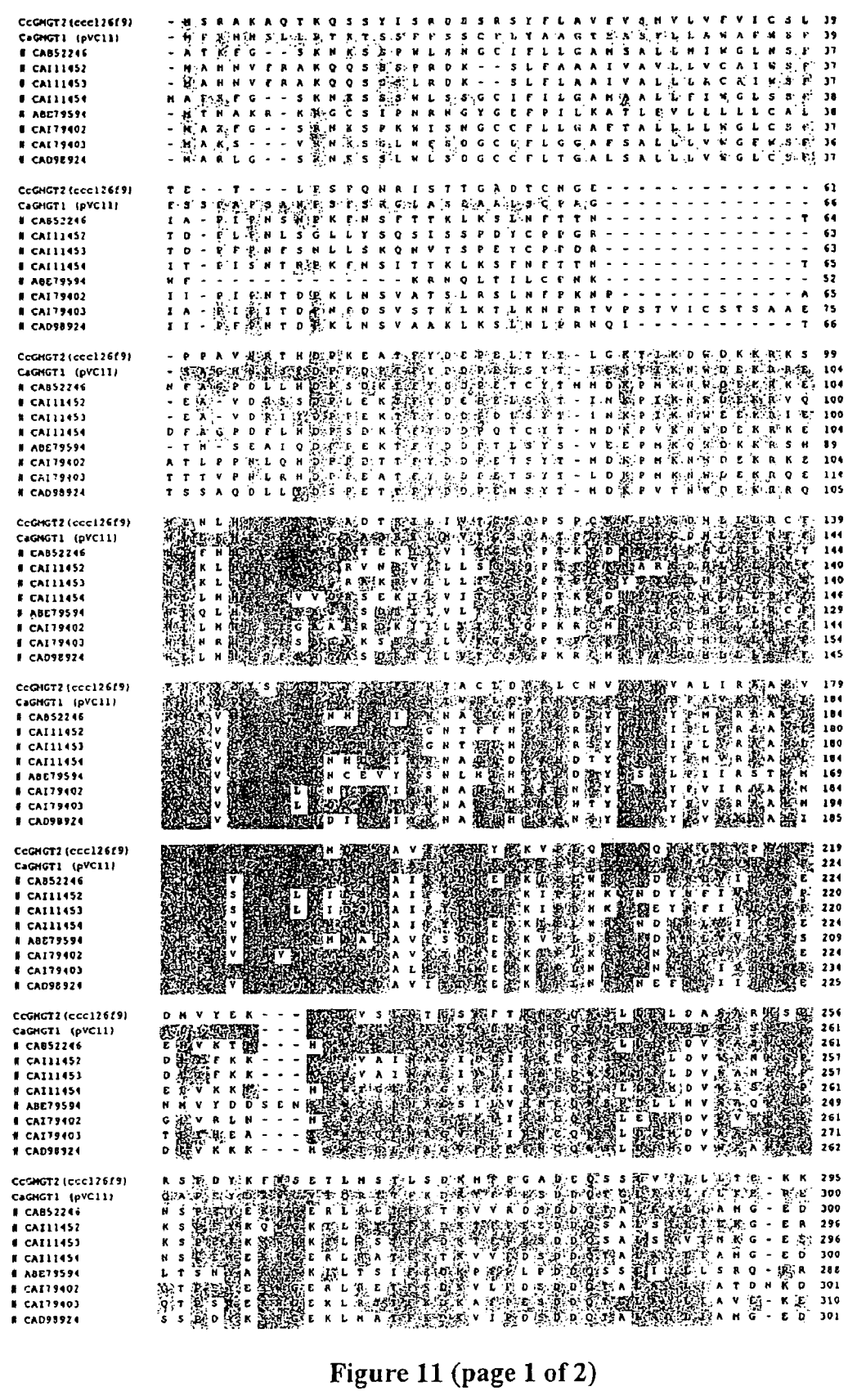
Figure 11:
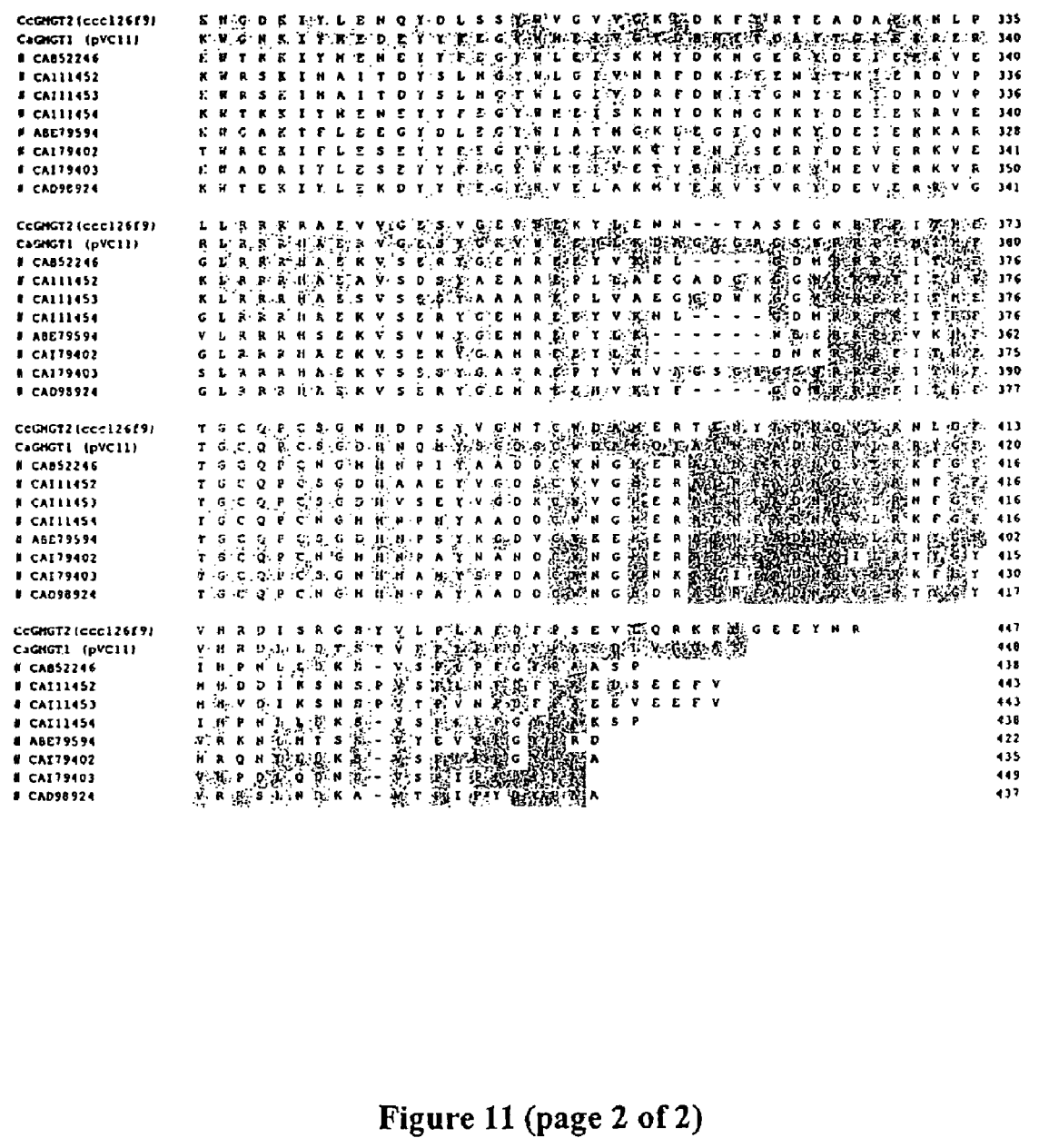

FIG. 11. Alignment of the protein sequence of CcGMGTase 2 (SEQ ID NO: 18) with CaGMGTase 1 (SEQ ID NO:17) and the most homologous protein sequences found in the GenBank public database. The alignment was made using CLUSTALW. Accession numbers: CAB52246: [*Trigonella foenum-graecum*] Alpha galactosyltransferase (SEQ ID NO:26); CAI11452: [*Solanum tuberosum*] Alpha-6-galactosyltransferase (SEQ ID NO:27); CAI11453: [*Nicotiana benthamiana*] Alpha-6-galactosyltransferase (SEQ ID NO:28); CAI11454: [*Medicago truncatula*] Alpha-6-galactosyltransferase (SEQ ID NO:29); ABE79594: [*Medicago truncatula*] Galactosyl transferase (SEQ ID NO:30); CAI79402: [*Cyamopsis tetragonoloba*] Galactomannan galactosyltransferase (SEQ ID NO:31); CAI79403: [*Senna occidentalis*] Galactomannan galactosyltransferase (SEQ ID NO:32); CAD98924: [*Lotus corniculatus* var. *japonicus*] Galactomannan galactosyltransferase (SEQ ID NO:33).

FIG. 12. Quantitative RT-PCR expression data for CaGMGT1 in various tissues of *Coffea canephora* and *Coffea Arabica*.

DETAILED DESCRIPTION OF ILLUSTRATIVE EMBODIMENTS

Definitions

Various terms relating to the biological molecules and other aspects of the present invention are used through the specification and claims. The terms are presumed to have their customary meaning in the field of molecular biology and biochemistry unless they are specifically defined otherwise herein.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid molecule", generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for Protein Modifications and Nonprotein Cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis.

Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

"Galactomannan synthesis enzyme" and "galactomannan synthesis gene" refers to a protein, or enzyme, and the gene that encodes the same, involved in the synthesis of galactomannan polymers. Galactomannan synthesis enzymes include mannan synthases and galactosyltransferases. Likewise, galactomannan synthesis genes include genes that encode mannan synthases and galactosyltransferases.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description

Galactomannan is an abundant polysaccharide and a significant component of the mature coffee grain. Its great presence in the mature coffee grain supports the thought that its role is to maintain the integrity of the grain. Consistent with that, galactomannans, along with other saccharide components in coffee grain, are thought to play a role in the extraction characteristics of coffee grain in water, which can affect the physical and chemical characteristics of the resulting coffee. Key enzymes involved in the metabolism of this polysaccharide are galactomannan synthesis enzymes, such as mannan synthases and galactosyltransferases.

One aspect of the present invention features nucleic acid molecules from coffee that encode mannan synthases and galactosyltransferases. cDNAs encoding a complete mannan synthases from *Coffea canephora* (pVC4, pVC6) are set forth herein as SEQ ID NOS: 1 and 2, respectively, and are referred to as CcManS. A cDNA encoding a complete mannan synthase from *Coffea arabica* (pVC7) is set forth herein as SEQ ID NO:3, and is referred to as CaManS. Partial genomic clones are set forth as SEQ ID NOS: 7, 8, 9 and 10, respectively, as discussed in the description of FIG. 2A and in the examples. Additionally, the present nucleic acid molecules include cDNAs that encode galactomannan galactosyltransferases, which in some cases are sequences that provide about 54% identity with a galactosyltransferases from fenugreek, and in some cases sequences that provide about 54% identity with a galactosyltransferases from *Japonicus*. In some embodiments these cDNAs include the sequences provided in SEQ ID NOS: 11 or 13, which are referred to as CcGMGT1, and SEQ ID NOS: 12 or 14, referred to as CcGMGT2.

Another aspect of the invention relate to the proteins produced by expression of these nucleic acid molecules and their uses. The deduced amino acid sequences of the CcManS protein produced by translation of SEQ ID NO:1 or SEQ ID NO:2 are set forth herein as SEQ ID NOS: 4 and 5, respectively. The deduced amino acid sequence of the CaManS protein produced by translation of SEQ ID NO:3 is set forth herein as SEQ ID NO:6. The deduced amino acid sequences of the CcGMGT1 protein produced by translation of SEQ ID NO:11 or SEQ ID NO:13 are set forth herein as SEQ ID NOS: 15 and 17, respectively. The deduced amino acid sequences of the CcGMGT2 protein produced by translation of SEQ ID NO:12 or SEQ ID NO:14 are set forth herein as SEQ ID NOS: 16 and 18, respectively. The table below lists the above-referenced polynucleotides and encoded proteins.

breeding and in genetic manipulation of plants, and ultimately in the manipulation of properties of the coffee grain.

Although polynucleotides encoding galactomannan synthesis enzymes from *Coffea canephora* and *Coffea arabica* are described and exemplified herein, this invention is intended to encompass nucleic acids and encoded proteins from other *Coffea* species that are sufficiently similar to be used interchangeably with the *C. canephora* and *Coffea arabica* polynucleotides and proteins for the purposes described below. Accordingly, when the galactomannan synthesis enzymes "mannan synthase" and "galactomannan galactosyltransferase" (or "galactosyltransferase") are referred to herein, these terms are intended to encompass all *Coffea* mannan synthases and galactosyltransferase having the general physical, biochemical and functional features described herein, and polynucleotides encoding them, unless specifically stated otherwise.

Considered in terms of their sequences, mannan synthase polynucleotides of the invention include allelic variants and natural mutants of SEQ ID NOS: 1-3, which are likely to be found in different varieties of *C. canephora* and *Coffea arabica*, and homologs of SEQ ID NOs: 1-3 are likely to be found in different coffee species. The galactosyltransferase polynucleotides include allelic variants and natural mutants of SEQ ID NOS: 11-14, which are likely to be found in different varieties of *C. canephora* and *Coffea arabica*, and homologs of SEQ ID NOs: 11-14 are likely to be found in different coffee species. Because such variants and homologs are expected to possess certain differences in nucleotide and amino acid sequence, there are isolated mannan synthase-encoding nucleic acid molecules and galactosyltransferase-encoding nucleic acid molecules that encode respective polypeptides having at least about 75% (and, with increasing order of preference, 76%, 77%, 78%, 79%, 70%, 81%, 82%, 83%, 84%, 85%, 86%, 87%, 88%, 89%, 90%, 91%, 92%, 93%, 94%, 95%, 96%, 97%, 98% and 99%) identity with the

| Polynucleotides and Polypeptides Involved in Galactomannan Synthesis | | | | |
|---|---|---|---|---|
| Enzyme | DNA | (SEQ ID NO:) | encoded protein | (SEQ ID NO:) |
| Mannan synthase - *C. canephora* | CcManS cDNA (pVC4) (full length) | 1 | CcManS | 4 |
| Mannan synthase - *C. canephora* | CcManS cDNA (pVC6) (full length) | 2 | CcManS | 5 |
| Mannan synthase - *C. arabica* | CaManS cDNA (pVC7) (full length) | 3 | CaManS | 6 |
| Mannan synthase - *C. canephora* | cccs46w16i11 insert (partial genomic) | 7 | | |
| Mannan synthase - *C. canephora* | cccs46w24c19 insert (partial genomic) | 8 | | |
| Mannan synthase - *C. canephora* | pVC2 (genomic RACE fragment) | 9 | | |
| Mannan synthase - *C. canephora* | pVC3 (genomic RACE fragment) | 10 | | |
| Galactomannan galactosyltransferase - *C. canephora* | CcGMGT1 (unigene 122620) | 11 | CcGMGT1 | 15 |
| Galactomannan galactosyltransferase - *C. canephora* | CcGMGT2 (unigene 122657) | 12 | CcGMGT2 | 16 |
| Galactomannan galactosyltransferase - *C. arabica* | CaGMGT1 (pVC11) (full length) | 13 | CaGMGT1 | 17 |
| Galactomannan galactosyltransferase - *C. canephora* | CcGMGT2 (ccc126f9) | 14 | CcGMGT2 | 18 |
| Galactomannan galactosyltransferase - *C. canephora* | ccccs46w8o23 (longest EST in unigene 122620) | 19 | | |
| Galactomannan galactosyltransferase - *C. arabica* | pVC10 (genomic RACE fragment) | 20 | | |

Still other aspects of the invention relate to uses of the nucleic acid molecules and encoded polypeptides in plant encoded polypeptide of SEQ ID NOS: 4, 5 or 6 in the case of mannan synthases, and SEQ ID NOS: 15, 16, 17 or 18 in the case of galactosyltransferase. Because of the natural sequence variation likely to exist among mannan synthases and galactosyltransferases, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOS: 1-3 (or fragments represented by SEQ ID NOS: 7-10) or 11-14 (or fragments represented by SEQ ID NOS: 19 and 20) enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level of sequence homology with part or all of the coding and/or regulatory regions of galactomannan synthesis enzyme-encoding polynucleotides may be identified by using hybridization and washing conditions of appropriate stringency. It will be appreciated by those skilled in the art that the aforementioned strategy, when applied to genomic sequences, will, in addition to enabling isolation of polysaccharide metabolizing enzyme-coding sequences, also enable isolation of promoters and other gene regulatory sequences associated with polysaccharide metabolizing enzyme genes, even though the regulatory sequences themselves may not share sufficient homology to enable suitable hybridization.

As a typical illustration, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm=81.5° C.+16.6 \log [Na+]+0.41(\% G+C)-0.63(\% \text{formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting galactomannan synthesis enzyme-encoding genes or mRNA in test samples of plant tissue, e.g., by PCR amplification, or for the positive or negative regulation of expression of galactomannan synthesis enzyme-encoding genes at or before translation of the mRNA into proteins. Methods in which galactomannan synthesis enzyme-encoding oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

The oligonucleotides having sequences capable of hybridizing with at least one sequence of a nucleic acid molecule of the present invention include antisense oligonucleotides. The antisense oligonucleotides are targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the mannan synthase- or galactosyltransferase-encoding sequence antisense strand is expressed by a transgene. In another embodiment, hybridizing sense and antisense strands of part or all of the mannan synthase-encoding sequence or galactosyltransferase-encoding sequence are transgenically expressed. In another embodiment, mannan synthase genes or galactosyltransferase genes or both may be silenced by use of small interfering RNA (siRNA; Elbashir et al., 2001, Genes Dev. 15 (2):188-200) using commercially available materials and methods (e.g., Invitrogen, Inc., Carlsbad Calif.).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides may be produced by expression in a suitable procaryotic or eucaryotic system. For example, part or all of a DNA molecule, such as the cDNA having SEQ ID NO:2 or SEQ ID NO:3, or any of SEQ ID NOS:11-14, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, and, thereafter, purified from the surrounding medium. An alternative approach involves purifying the recombinant protein by affinity separation, e.g., via immunological interaction with antibodies that bind specifically to the recombinant protein.

The polypeptides of the invention, prepared by the aforementioned methods, may be analyzed according to standard procedures.

Polypeptides purified from coffee or recombinantly produced, may be used to generate polyclonal or monoclonal antibodies, antibody fragments or derivatives as defined herein, according to known methods. In addition to making antibodies to the entire recombinant protein, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Vectors, Cells, Tissues and Plants:

Also featured in accordance with the present invention are vectors and kits for producing transgenic host cells that contain a galactomannan synthesis enzyme-encoding polynucleotide or oligonucleotide, or variants thereof in a sense or antisense orientation, or reporter gene and other constructs under control of polysaccharide metabolizing enzyme-promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a galactomannan synthesis enzyme-encoding gene, or nucleic acid sequences that inhibit the production or function of a plant's endogenous galactomannan synthesis enzyme. This is accomplished by transforming plant cells with a transgene that comprises part of all of a galactomannan synthesis enzyme coding sequence, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruweniiensis, C. bengalensis, C. canephora, C. congensis C. Dewevrei, C. excelsa, C. eugenioides,* and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' (e.g., promoters and translational regulatory sequences) and 3' regulatory sequences (e.g., terminators). In one embodiment, galactomannan synthesis enzyme-encoding sequences under control of its own 5' and 3' regulatory elements can be utilized. In other embodiments, galactomannan synthesis enzyme-encoding and regulatory sequences are swapped to alter the polysaccharide profile of the transformed plant for a phenotypic improvement, e.g., in flavor, aroma or other feature, such as froth of coffee produced.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants expressing galactomannan synthesis enzyme coding sequences under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin, beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999)1 See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. US2006/026121, the dehydrin gene promoter described in commonly-owned, co-pending PCT Application No. US2006/026234, and the 9-cis-epoxycarotenoid dioxygenase gene promoter described in commonly-owned, co-pending PCT Application No. US2006/034402. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll alb binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not used, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomaimose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby production of the protein products in coffee plants can be modulated to affect various phenotypic traits, e.g., for enhancement of the flavor, froth (physical property) and/or aroma of the coffee beverage or coffee products ultimately produced from the bean, or for improvement in the production qualities of the beans. For instance, a decrease in galactomannan content, or an alteration of galactomannan structure, is expected to greatly improve recovery of solids in the process of making instant coffee.

Improvement of coffee grain polysaccharide profile or other characteristics can be obtained by (1) classical breeding or (2) genetic engineering techniques, and by combining these two approaches. Both approaches have been considerably improved by the isolation and characterization of a galactomannan synthesis enzyme-encoding gene in coffee, in accordance with the present invention. For example, the mannan synthase- or galactosyltransferase-encoding genes may be genetically mapped and Quantitative Trait Loci (QTL) involved in coffee flavor can be identified. It would be then be possible to determine if such QTL correlate with the position of mannan synthase or galactosyltransferase related genes. Alleles (haplotypes), for genes affecting polysaccharide metabolism may also be identified and examined to determine if the presence of specific haplotypes are strongly correlated with galactomannan synthesis. These markers can be used to advantage in marker assisted breeding programs. A third advantage of isolating polynucleotides involved in galactomannan synthesis is to generate expression data for these genes during coffee bean maturation in varieties with high and low galactomannan levels. This information can be used to direct the choice of genes to use in genetic manipulation aimed at generating novel transgenic coffee plants that have increased or decreased galactomannan levels in the mature bean.

In one aspect, the present invention features methods to alter the galactomannan profile in a plant, preferably coffee, comprising increasing or decreasing an amount or activity of one or more galactomannan synthesis enzyme in the plant. Specific embodiments of the present invention provide methods for increasing or decreasing production of mannan synthase.

In one embodiment coffee plants can be transformed with a mannan synthase-encoding polynucleotide, such as a cDNA comprising SEQ ID NO: 2 or 3, or 11-14, for the purpose of over-producing mannan synthase or galactosyltransferase, respectively, in various tissues of coffee. In one embodiment, coffee plants are engineered for a general increase in mannan synthase production, e.g., through the use of a promoter such as the RuBisCo small subunit (SSU) promoter or the CaMV35S promoter functionally linked to a mannan synthase gene. In another embodiment, coffee plants are engineered for a general increase in galactosyltransferase production, e.g., through the use of a promoter such as the RuBisCo small subunit (SSU) promoter or the CaMV35S promoter functionally linked to a galactosyltransferase gene. In some embodiments, the modification of coffee plants can be engineered to increase both mannan synthase and galactosyltransferase production. In another embodiment designed to limit production of the mannan synthase, or galactosyltransferase, only to the sink organ of interest, i.e., the grain, a grain-specific promoter may be utilized, particularly one of the *Coffea* grain-specific promoters described above.

Plants exhibiting altered galactomannan profiles can be screened for naturally-occurring variants of mannan synthase or galactosyltransferase. For instance, loss-of-function (null) mutant plants may be created or selected from populations of plant mutants currently available: It will also be appreciated by those of skill in the art that mutant plant populations may also be screened for mutants that under or over-express a particular polysaccharide metabolizing enzyme, such as a galactomannan synthesis enzyme, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135 (2): 630-636; Gilchrist & Haughn, 2005, Curr. Opin. Plant Biol. 8 (2): 211-215). The methods to make mutant populations are well known in the art.

The nucleic acids of the invention can be used to identify mutant forms of galactomannan synthesis enzymes in various plant species. In species such as maize or *Arabidopsis*, where transposon insertion lines are available, oligonucleotide primers can be designed to screen lines for insertions in the galactomannan synthesis enzyme genes. Through breeding, a plant line may then be developed that is heterozygous or homozygous for the interrupted gene.

A plant also may be engineered to display a phenotype similar to that seen in null mutants created by mutagenic techniques. A transgenic null mutant can be created by expressing a mutant form of galactomannan synthesis enzyme to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al, 1997, Genetics 145: 163-171; Kolch et al., 1991, Nature 349: 426-428).

Another kind of transgenic null mutant can be created by inhibiting the translation of galactomannan synthesis enzyme-encoding mRNA by "post-transcriptional gene silencing." These techniques may be used to down-regulate mannan synthase in a plant grain, thereby altering the polysaccharide profile. For instance, a galactomannan synthesis enzyme-encoding gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the mannan synthase-encoding sequence antisense strand is expressed by a transgene. In another embodiment, part or all of the mannan synthase-encoding sequence antisense strand is expressed by a transgene.

In another embodiment, galactomannan synthesis-encoding genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, Differentiation 72: 65-73; Baulcombe, 2004, Nature 431: 356-363; Herr, 2004, Biochem. Soc. Trans. 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by an common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16 (6): 651-659). Plant cells are transformed with a copy of the endogenous gene targeted for repression. In many cases, this results in the complete repression of the native gene as well as the transgene. In one embodiment, a galactomannan synthesis enzyme-encoding gene from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of polysaccharide metabolizing enzymes and its affects on polysaccharide profiles, thereby affecting the flavor, aroma and other features of coffee seeds. Plants containing one transgene or a specified mutation may also be crossed with plants containing a complementary transgene or genotype in order to produce plants with enhanced or combined phenotypes.

The following examples are provided to describe the invention in greater detail. The examples are for illustrative purposes, and are not intended to limit the invention.

EXAMPLE 1

Materials and Methods for Subsequent Examples

Plant Material. *Coffea canephora* (BP409, 2001) cherries were harvested from trees in the field at the Indonesian Coffee and Cacao Research Center (ICCRI), Indonesia. Immediately after harvesting, the cherries were frozen in liquid nitrogen and then sent frozen on dry ice to the location designated for further processing. Samples were frozen at −25° C. for transportation, then stored at −80° C. until use.

DNA Sequence Analysis. For DNA sequencing, recombinant plasmid DNA was prepared and sequenced according to standard methods. Computer analysis was performed using DNA Star (Lasergene) software. Sequence homologies were verified against GenBank databases using BLAST programs (Altschul et al. 1990).

cDNA Preparation. cDNA was prepared from total RNA and oligo dT(18) (Sigma) as follows: 1 μg total RNA sample plus 50 ng oligo dT was made up to 12 μl final volume with DEPC-treated water. This mixture was subsequently incubated at 70° C. for 10 min and then rapidly cooled on ice. Next, 4 μl of first strand buffer (5×, Invitrogen), 2 μl of DTT (0.1 M, Invitrogen) and 1 μl of dNTP mix (10 mM each, Invitrogen) were added. These reaction mixes were preincubated at 42° C. for 2 min before adding 1 μl-SuperScript III Rnase H-Reverse transcriptase (200 U/μl, Invitrogen). Subsequently, the tubes were incubated at 25° C. for 10 min and then at 42° C. for 50 min, followed by enzyme inactivation by heating at 70° C. for 10 min. The cDNA samples generated were then diluted ten-fold in sterile water and stored at −20° C. for use in some of the following experiments, such as 5' RACE, isolating full length cDNA clones, and QRT-PCR.

5' RACE Reactions (Rapid Amplification of cDNA Ends)

To recover the 5' coding sequence of the coffee mannan synthase, two rounds of 5' RACE were carried out. The RNA used for the synthesis of cDNA in 5' RACE experiments is *Coffea canephora* (BP409) grain at the yellow stage. The 5' RACE experiments were carried out using methods that closely follow the methods described in the kit for the 5' RACE system for Rapid Amplification of cDNA Ends kit (Invitrogen). Briefly, the cDNA used in this experiment was first purified to remove any unincorporated nucleotides (as they would interfere in the dC tailing reaction). This step was accomplished by purifying the 5' RACE cDNA on S.N.A.P. columns (Invitrogen) precisely according to the instructions given by the manufacturer. Once purified, the cDNA were recovered in 50 μL of sterilized water and then were stored at −20° C. before being used for 5' RACE PCR.

The 5' RACE experiments all began with a TdT tailing of the S.N.A.P. purified cDNA. The poly dC tailing reaction was as follows: 25 μl reactions were set up with 5 μl of the purified cDNA, 11.5 μl DEPC treated water, 5 μl 5× TdT tailing buffer (Invitrogen), and 2.5 μl 2 mM dCTP. The reactions were then incubated at 94° C. 3 minutes, followed by chilling on ice. 1 μl of TdT was then added and the reaction was incubated for 10 minutes at 37° C. The reactions were terminated by heating 10 minutes at 65° C. and again placed on ice.

The first round of 5' RACE reactions were performed in a final 50 μl volume, as follows: 5 μL of each tailed cDNA, 5 μl 10×PCR buffer (ThermoPol buffer), 400 nM of both Gene Specific Primer 1 and AAP primers (see Tables 1 and 2 for primers), 200 μM each dNTP, and 2.5 U of Taq DNA polymerase (BioLabs). The first round PCR cycling conditions were: 94° C. for 2 min; then 40 cycles of 94° C. for 1 min, annealing temperature noted in Table 2 for 1 min, and 72° C. for 2 min for 40 cycles. An additional final step of elongation was done at 72° C. for 7 min. The PCR products were then analyzed by agarose gel electrophoresis and ethidium bromide staining.

The second round PCR reactions were performed in a final 50 μl volume, as follows: 5 μL of 1% diluted First Round PCR product; 5 μl 10×PCR buffer (LA buffer II Mg$^{++}$ plus), 200 nM of both Gene Specific Primer 2 and AUAP primers (see Tables 1 and 2 for specific primers used), 200 μM each dNTP, 0.5 U of DNA polymerase Takara LA Taq (Cambrex Bio Science). The cycling protocol was: 94° C. for 2 min; then 40 cycles of 94° C. for 1 min, the annealing temperature noted in Table 2 for 1 mM, and 72° C. for 1 min 30 seconds. An additional final step of elongation was done at 72° C. for 7 min. PCR products were then analyzed by agarose gel electrophoresis and ethidium bromide staining.

TABLE 2

Primers and PCR Conditions Used for the Different 5' RACE Experiments.

| Experiment | Gene specific primer | Annealing temperature | Number of cycles |
|---|---|---|---|
| CcManS Race1 | | | |
| First round RACE PCR | RNAi-Pr2 | 55° C. | 40 |
| Second round RACE PCR | ManSynt GWR249 | 55° C. | 40 |
| CcManS Race2 | | | |
| First round RACE PCR | ManSRace2 | 55° C. | 40 |
| Second round RACE PCR | ManSRace1 | 62° C. | 40 |

The primers, annealing temperatures, and the number of cycles are given for the various 5' RACE PCR reactions. The DNA sequences of the primers are given above, Table 1.

Isolation of cDNA Containing the Complete Coding Sequences (Complete ORF's) for ManS from *coffea canephora* and *coffea arabica* Using Gene Specific Primers.

The existing cDNA sequences, and the new 5' sequences obtained from 5' RACE, were used to design 2 gene specific primers in the 5' and 3' UTR sequences to amplify the complete ORF sequences of ManS (pVC4, pVC6, and pVC7). The cDNA used to isolate the complete ORF sequences are noted in Table 3 (Seed, yellow stage, BP409; and Seed, yellow stage, T2308), and the sequences of the specific primers for each PCR reaction are given in Table 4. The PCR reactions were performed in 50 μl reactions as follows: 5 μL of cDNA (Table 3 and 4), 5 μl 10×PCR buffer (La PCR Buffer II Mg$^{++}$ plus), 800 nM of the each gene specific primer, 200 μM of each dNTP, and 0.5 U of DNA polymerase Takara LA Taq (Cambrex Bio Science). After denaturing at 94° C. for 2 min, the amplification consisted of 35 cycles of 1 min at 94° C., 1 min 30 seconds at annealing temperature (47° C.), and 3 min at 72° C. An additional final step of elongation was done at 72° C. for 7 min. The PCR products were then analyzed by agarose gel electrophoresis and ethidium bromide staining. Fragments of the expected size were then cloned in pCR4-TOPO using TOPO TA Cloning Kit for Sequencing (Invitrogen) according to the instructions given by the manufacturer. The inserts of the plasmids generated were then sequenced entirely.

TABLE 1

List of primers used for 5'RACE PCR experiments

| Primers | Sequences | SEQ ID NO: |
|---|---|---|
| AAP (Abridged Anchor Primer) | 5' GGCCACGCGTCGACTAGTACGGGIIGGGIIGGGIIG 3' | 34 |
| AUAP (Abridged Universal Amplification Primer) | 5' GGCCACGCGTCGACTAGTAC 3' | 35 |
| RNAi-Pr2 | 5' GAACATGTTGACGAGCCT 3' | 36 |
| ManSynGWR249 | 5' GCCCGCAGGACTTCATTCGTGGAG 3' | 37 |
| ManSRace2 | 5' ATACTTGGTATATCGTTTCCTTCC 3' | 38 |
| ManSRace1 | 5' TGACACATCCAATCACATCGC 3' | 39 |

TABLE 3

Isolation of cDNA sequences encoding the full length protein sequences for *Coffea canephora* Mannan Synthase (CcManS) and *Coffea arabica* Mannan Synthase (CaManS).

| Gene | CDNA tissue and genotype | Gene specific primer | Annealing temperature |
|---|---|---|---|
| CcManS | BP409 Seed, yellow stage | ManS-Am3/ ManS-Am2 | 47° C. |
| CaManS | *C. arabica* T2308 Seed, yellow stage | ManS-Am3/ ManS-Am2 | 47° C. |

The specific cDNA, primers, and PCR annealing temperatures used to amplify the complete ORF sequences are presented. These cDNAs were synthesized as described in the methods.

TABLE 4

Sequences of the primers used for the amplification of cDNA sequences encoding the full length protein sequences of CcManS and CaManS.

| PRIMERS | SEQUENCES | SEQ ID NO: |
|---|---|---|
| ManS-Am3 | 5' CTGCTCATTGCCCTCAG 3' | 40 |
| ManS-Am2 | 5' GACTTGCTGTACTCGTCTA 3' | 41 |

Expression Analysis of CcManS Using Quantitative RT-PCR (Q-RT-PCR)

The cDNA used for these experiments was prepared according to the methods described above (robusta; *C. canephora* BP 409 1/1000 dilution; arabica cDNA sample; *C. arabica* T-2308 1/1000 dilution, cDNA sample). TaqMan-PCR was performed as recommended by the manufacturer (Applied Biosystems, Perkin-Elmer). Briefly, 25 ul reactions were set up in reaction plates (MicroAmp Optical 96-well Reaction plate Applied Biosystems ref: N801-0560). Each reaction contained 12.5 ul of AmpliTaq Gold Master mix, 2.5 ul of the two primers (8 uM stock, 800 nM final in reaction), 2.5 ul MGB TaqMan probe (2 uM stock, 200 nM final in reaction), and 5 ul of DNA sample plus water. The water and DNA is added to the plates first, then the "Specific Mix" (AmpliTaq Gold Master mix+primers and TaqMan probe) is added. The reactions are made up at room temperature and the Taq amplifications begin only when the Taq is activated by releasing the bound antibody at high temperatures, ie. Hot-Start. The TaqMan buffer contains AmpErase® UNG (Uracil-N-glycosylase), which is active during the first 2 min at 50° C. and is then inactivated at 95° C. at the start of the PCR cycling. The cycling conditions used (7500 Real Time PCR System—Applied Biosystems) were 50° C. 2 minutes, 95° C. 10 minutes, then 40 cycles of 95° C. 15 seconds and 60° C. 1 minute. Each reaction was done in triplicate and the average Ct value for the three reactions were calculated.

The primers and TaqMan probes used were designed with the PRIMER EXPRESS software (Applied Biosystems). The primers and mannan synthase MGB probe used for Q-PCR experiments are 124613-F1, 124613-R1 and 124613MGB1 (see table 5). Quantification was carried out using the method of relative quantification (RQ), using the constitutively expressed coffee ribosomal protein gene CcRp139 as the reference. In this case, the average Ct is calculated for the CcManSyn (test gene) and CcRp139 (reference gene) genes from the replicates done for each gene in each tissue sample. The RQ value ($2^{-deltaCt}$; with delta Ct=CcManS Ct−CcRp139 Ct), which is a measure of the difference between the two samples, is then calculated. In order to use the method of relative quantification, it is necessary to show that the amplification efficiency for the test gene is equivalent to the amplification efficiency of the reference sequence (rp139 cDNA sequence) using the specified primer and probe sets (efficiency of amplification near 1, ie. 100%). To determine this relative equivalence, plasmid DNA containing the appropriate cDNA sequences were diluted 1/1000, 1/10,000, 1/100,000, and 1/1,000,000 fold, and using the Q-PCR conditions described above, the slope of the curve Ct=$f$ (Log quantity of DNA) was calculated for each plasmid/primer/TaqMan probe set. Plasmid/primer/TaqMan probe sets giving curves with slopes close to 3.32, representing an efficiency of 100%, are considered acceptable. The plasmid/primer/TaqMan probe sets used here have acceptable values for Ct=$f$ (Log quantity of DNA).

TABLE 5

List of primers used for Q-PCR experiments.

| Primers | Sequences | SEQ ID NO: |
|---|---|---|
| 124613-F1 | 5' AATGTCATGTCCCTCCATCGA 3' | 42 |
| 124613-R1 | 5' AACTCGGCTGGCTTCTAAAAGTC 3' | 43 |
| 124613MGB1 | 5' FAM-CAAAGCAGCAATTAT-MGB 3' | 44 |
| rp139-F1 | 5' GAACAGGCCCATCCCTTATTG 3' | 45 |
| rp139-R1 | 5' CGGCGCTTGGCATTGTA 3' | 46 |
| rp139-MGB1 | 5' VIC-TGACACATCCAATCACATCGC-MGB 3' | 47 |

EXAMPLE 2

Identification of cDNA Encoding Mannan Synthase in *C. canephora*

More than 47,000 EST sequences were identified from several coffee libraries made with RNA isolated from young leaves and from the grain and pericarp tissues of cherries harvested at different stages of development. Overlapping ESTs were subsequently "clustered" into "unigenes" (i.e., contigs) and the unigene sequences were annotated by doing a BLAST search of each individual sequence against the NCBI non-redundant protein database.

Galactomannans contribute greatly to the dry weight of the mature coffee grain and is thought to play an important role in the access or extractability of molecules within the grain, e.g., sugars. Methods were taken to isolate one of the key genes involved in galactomannan synthesis, i.e., mannan synthase, and to study the expression of this gene in developing coffee grain. The protein sequence of the biochemically characterized mannan synthase from guar (CtManS, *Cyamopsis tetragonoloba*, accession number AAR23313; Dhugga, et. al., 2004) was used to search our 'unigene' set of DNA sequences using the tblastn algorithm (Altschul, et. al., 1990). This search uncovered one unigene with a very high level of homology (unigene #124613). See Table 6. The two longest EST's in this unigene were isolated and completely sequenced: one, the insert in pcccs46w16i11, was found to be 1779 bp long; while the second, an insert in pcccs46w24c19, was found to be 1349 bp long. An alignment analysis between these two sequences indicated that two intron sequence existed in the cDNA of pcccs46w16i11. As noted graphically in FIG. 2A, one of the introns was at the 5' end of this clone, while the other, much smaller, intron sequence was found buried in the ORF of the cDNA. When the intron sequences were spliced out of the consensus sequence for these two cDNA clones, a partial ORF of 423 amino acids was uncovered; however, the full length guar protein is 526 amino acids long. Thus the coffee ManS cDNA was not complete and lacked over 309 base pairs (i.e., encoding 103 amino acids plus the 5' UTR).

TABLE 6

In silico distribution of coffee mannan synthase ESTs.

| Gene | Unigene | ESTs fully sequenced | cccl | cccp | cccwc22w | cccs18w | cccs30w | cccs46w |
|---|---|---|---|---|---|---|---|---|
| CcManS | 124613 | Cccs46w16i11 (with 2 introns) Cccs46w24c19 | | | | | 4 | 13 |

The number of mannan synthase EST's (unigene 124613) found in each of the different *Coffea canephora* EST libraries.

EXAMPLE 3

Full Length ManS Sequence

The clone pccs46w16i11 encodes a significant part of the coffee ManS sequence, thus, it was used to design specific primers for use in the well-established technique of primer assisted genome walking. The first experiment yielded a 1084 bp long fragment (pJMc2), which lengthened the intronic region by a further 1000 bp more. However, as the new sequence did not contain any sequence information on the next exon, this fragment did not yield any new sequence data on the ORF. Further genome walking experiments did not generate new upstream sequences.

Figure 2A:
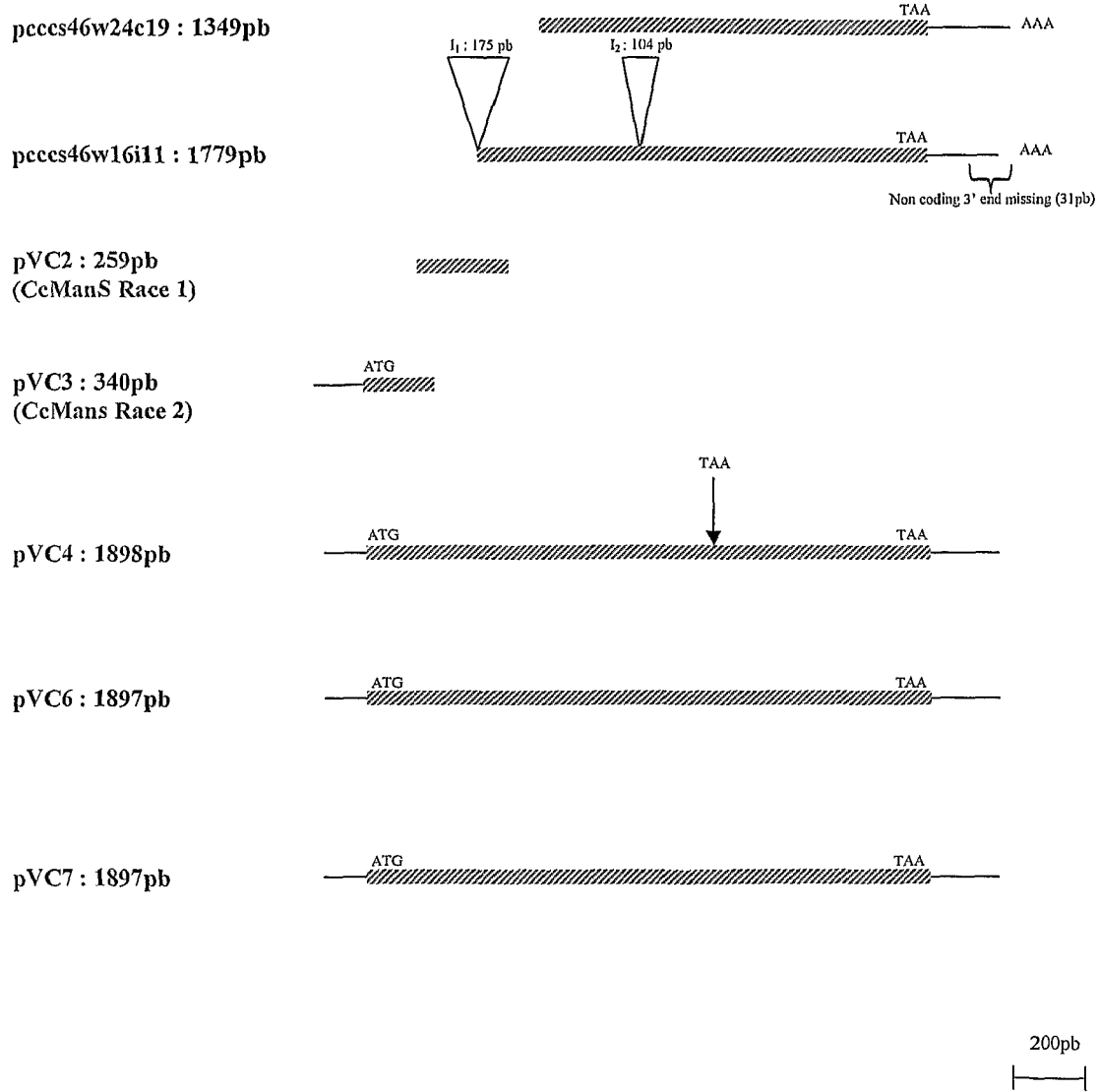
FIG. 2. Isolation and characterization of the complete coding sequences for nucleic acids encoding mannan synthases from *Coffea canephora* and from *Coffea arabica*.

5' RACE PCR, as described in Example 1, was carried out to isolate the missing 5' coding region of this gene. This was accomplished using the gene specific primers RNAi-Pr2-GSP1 and ManSynt GWR249-GSP2. The result was a 300 base pair PCR fragment, which was cloned into pCR-4-TOPO vector and then sequenced. The sequence obtained (pVC2; CcManS Race1) was 259 pb long and overlapped the 5' end of the cDNA clone pccs46w16i11 (FIG. 2, showing 99 bp of overlapping sequence). However, this RACE fragment was determined to be missing the 5' end of this gene. Therefore, a new 5' RACE PCR were carried out using gene specific primers ManSRace2 and ManSRace1. This produced an approximately 400 base pair PCR fragment, which was cloned into pCR-4-TOPO vector and then sequenced. The sequence obtained (pVC3 CcManS Race2) was 340 bp long and overlapped the 5' end of the CcManS Race1 fragment (FIG. 2A, showing 38 bp of overlapping sequence).

Figure 2B:
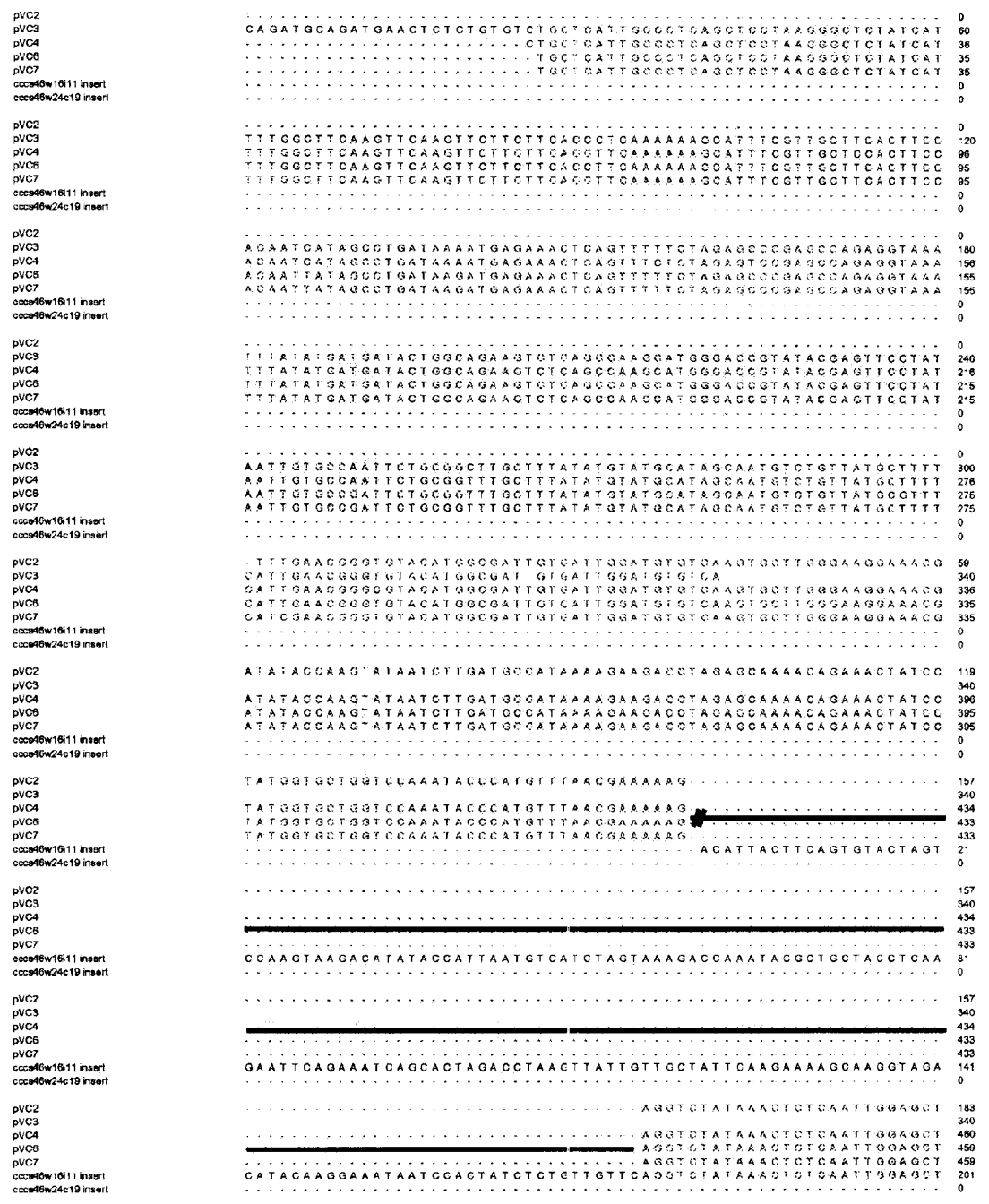
Figure 2C:
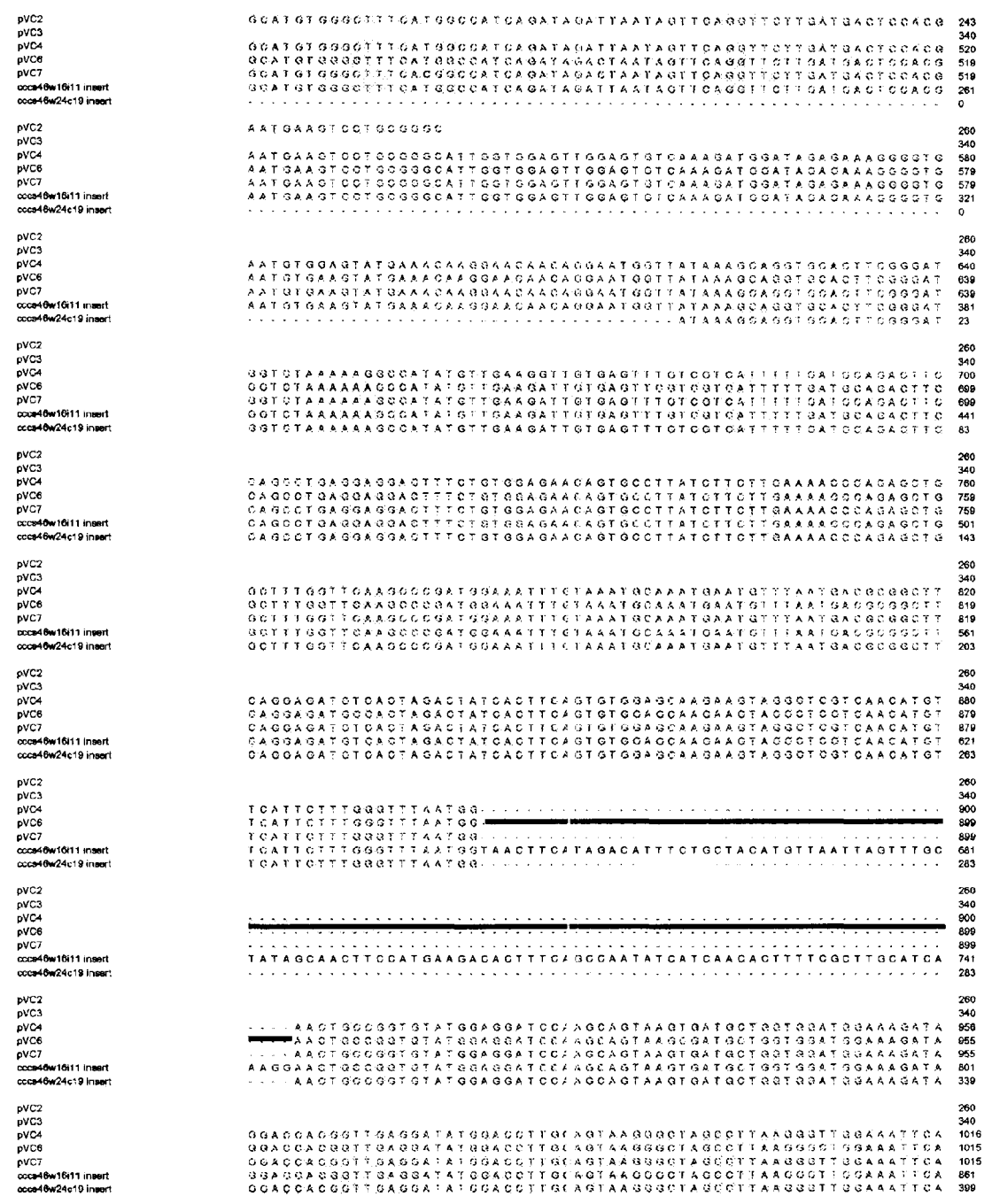
Figure 2D:
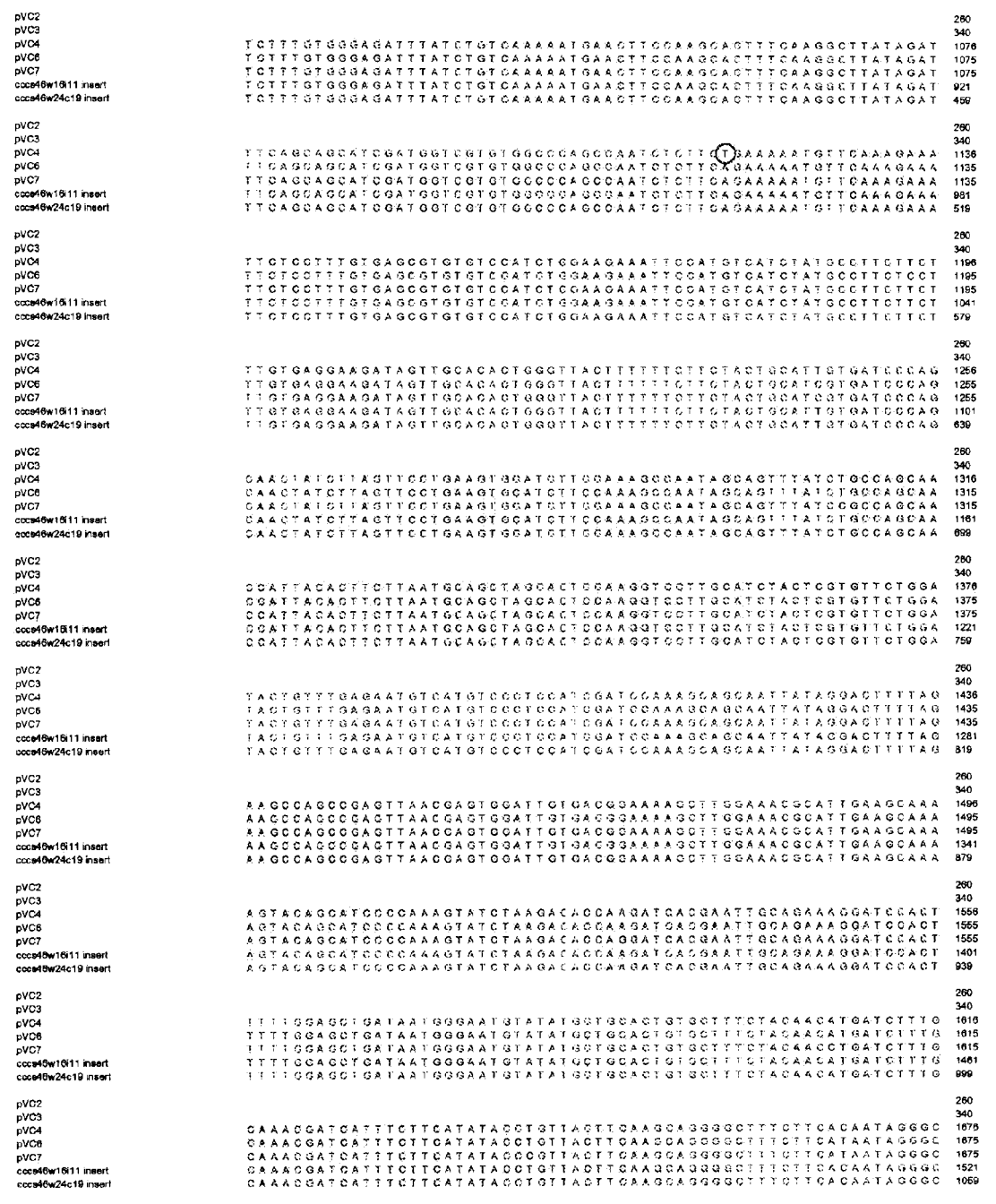

The various clones, as shown in FIG. 2A, allowed the generation of the DNA alignment shown in FIGS. 2B-2E, which shows the overlapping sequences of these clones. This DNA sequence information was used to find the complete ORF for the coffee mannan synthase CcManS. From the newly isolated coffee 5' end ManS sequence (CcManS Race2), and the nearly full length coding sequence in the cDNA pccs46w16i11, two new primers (ManS-Am3 and ManS-Am2, Table 7) were designed, which were capable of specifically amplifying the complete ORF sequence of the coffee mannan synthase using cDNA made from RNA of *C. canephora* (BP-409) or *Coffea arabica* (T2308) isolated from grain at the yellow development stage (Table 7). This PCR amplification experiment resulted in the generation of the cDNA sequences that are contained in the plasmids pVC4 (robusta cDNA), pVC6 (robusta cDNA), and pVC7 (Arabica cDNA), respectively (FIGS. 2B-2E). Sequence analysis of the pVC4 insert indicated that this cDNA was 1898 bp, and encoded a polypeptide of 530 amino acids (estimated molecular weight of 61.29 kDa). Note: the DNA sequence of the insert in pVC4 was found to have a base change causing a stop codon in the ORF. As explained in the legend of FIGS. 2B-2E, this base change is a PCR error and is not coded by the corresponding genomic sequence. Sequence analysis of the inserts of pVC6 and pVC7 demonstrated that these cDNA sequences were 1897 bp long and each had a complete ORF of 1590 bp, encoding polypeptides of 530 amino acids estimated molecular weights of 61.3 kDa and 61.15 kDa, respectively.

TABLE 7

Sequences of the primers used for the amplification of cDNA sequences encoding the full length protein sequences of CcManS.

| PRIMERS | SEQUENCES | SEQ ID NO: |
|---|---|---|
| ManS-Am3 | 5' CTGCTCATTGCCCTCAG 3' | 40 |
| ManS-Am2 | 5' GACTTGCTGTACTCGTCTA 3' | 41 |

These protein sequences were then aligned with the protein sequence of the biochemically characterized guar mannan synthase (CtManS), as well as two of the most closely related sequences found in the GenBank database, the product of one of which has not been characterized (i.e., *I. Trifida*). The result of this alignment (FIG. 4) shows that *Coffea canephora* ManS (CcManS; pVC6) sequence exhibits 74.7%, 65.9%, and 58.7% identity with the *C. tetragonoloba*, *A. thaliana*, and *I. Trifida* sequences, respectively. The arabidopsis sequence in this alignment is also called AtCSLA9 (arabidopsis cellulose synthase like protein family A gene #9) and the protein encoded by this gene has very recently been shown to have mannan synthesis activity, and to a lessor extent glucomannan synthesis activity (Liepman, A., Wilkerson, C., Keegstra, K. 2005 Expression of cellulose synthase-like (Csl) genes in insect cells reveals the CslA family members encode mannan synthases. Proc. Natl. Acad. Sci. 102, 2221-2226). The high levels of identity between the coffee and guar protein sequences strongly supports the argument that the CcManS and CaManS sequences encodes the protein responsible for mannan synthsesis in the coffee grain. It is also noted that the ManS sequences of *Coffea canephora* (pVC6) and *Coffea arabica* (pVC7) share 98.5% identity, and have only 12 nucleotide differences, which translated into an 8 amino acid difference. It may be that these subtle differences in mannan synthase proteins contribute to the difference of extraction rates generally known to exist between these two types of coffee.

An alignment of the insert DNA sequences of pVC4 (Cc-ManS), pVC6 (CcManS), and pVC7 (CaManS) was made with the MansS cDNA sequences of *C. tetragonoloba* (AAR23313) and *A. thaliana* (CAB82941) using ClustalW. This DNA alignment showed that the coffee sequences were, as noted above, nearly identical. In contrast, the *C. tetragonoloba* sequence showed approximately 67% homology with the coffee mannan synthase sequences and *A. thaliana* showed approximately 55% homology with the coffee mannan synthase sequences (CAB82941). In addition, the regions of identity were scattered regularly throughout the entire sequences and thus no very long contiguous regions of indentity were found between the coffee sequences and the guar and arabidopsis sequences.

EXAMPLE 4

CcManS Expression Analysis

To ensure that the CcManS gene encodes a cellulose synthase-like (Csl) family member with mannan synthase activity, this gene was demonstrated to only express in the tissue(s) that show a high level of mannan and galactomannan synthesis. The expression of CcManS was studied in various tissues of arabica and robusta using quantitative RT-PCR. The results obtained clearly show that mannan synthase is both highly and almost exclusively expressed in the grain of both robusta and arabica, with the arabica T2308 grain appearing to have slightly higher levels of mannan synthase expression than robusta BP409 grain. This suggests that there may be higher levels of mannan synthase activity in arabica grain versus robusta grain, particularly late in grain development. This difference in activity could lead to higher levels and/or different structures of the mannans/galactomannans found in the arabica grain. Such differences could explain, generally, the greater difficulty experienced in extracting solid material from roasted, or processed, arabica grain versus robusta grain.

Slight or no mannan synthase expression was detected using QRT-PCR in the stem, roots, leaves, pericarp and flower tissues from arabica T2308 or robusta BP409. The small green robusta sample was the only grain sample to have no detectable mannan synthase gene expression, and this is in agreement with earlier results that show that this particular robusta stage/sample does not yet express other endosperm specific genes such as the oleosins (see, e.g., commonly-owned, co-pending Application No. 60/696,445). In sum, all the mannan synthase expression data shows that mannan synthase is exclusively, or nearly exclusively, expressed in the coffee grain at the later stages of development when the endosperm is forming or developing. Consistent with this finding, the mannan synthase EST's were also only detected in the libraries made with RNA extracted from grain at the later stages of development, and not in the libraries made from RNA extracted from early stage coffee cherries, coffee cherry pericarp tissues, or from leaf tissues (see Table 6). Overall, the mannan synthase expression data is consistent with the theory that the mannan synthase gene encodes the main enzyme involved in mannan synthesis, and by association, the main enzyme involved in galactomannan synthesis, in the grain of coffee.

TABLE 8

Relative expression of CcManS vs. CcRpl39

| | Relative Expression: $RQ = 2^{-deltaCt}$ | |
|---|---|---|
| | Robusta BP409 | *Arabica* T2308 |
| Small Green grain | ND | 1.140 |
| Large Green grain | 0.530 | 1.910 |
| Yellow grain | 1.150 | 0.202 |
| Red grain | 0.012 | 0.300 |

ND = not detected

EXAMPLE 5

Identification of cDNA Encoding UDP-Gal Dependant Mannan Specific (1,6)-alpha-D-Galactosyltransferase (GMGT) in *C. canephora*

A second enzyme involved in the synthesis of galactomannans is the enzyme $Mn^{++}$ dependant, UDP-Gal dependent mannan specific (1,6)-alpha-D-galactosyltransferase (GMGT; (Edwards, Choo, Dickson, Scott, Gridley, and Reid 2004). GMGT along with mannan synthase are thought to work in close association, possibly as a complex, to generate galactomannans.

The protein sequence of a biochemically characterized GMGT protein of *Lotus japonicus* (accession number AJ567668) was used to search our 'unigene' set of DNA sequences using the tblastn algorithm (Altschul, et. al., 1990). This search uncovered two unigenes with a high level of homology (unigene #122567 and unigene #122620). Table 9 shows the number of EST's found for each unigene in the different *C. canephora* libraries. Given that EST's of unigene 122620 are only found in the seed, and that EST's for unigene 122567 are only found in the leaf, it is probable that unigene #122620 represents a gene that encodes a grain specific coffee GMGT. In following, this GMGT protein (CcGMGT1) is thought to work with the CcManS, described herein, to synthesize the vast majority of the coffee grain galactomannans. In contrast, the gene represented by unigene #122567 is likely to encode another coffee GMGT protein (GMGT2), which is associated with galactomannan synthesis in other coffee tissues such as in the leaf.

The alignments of each unigene are shown in FIGS. 5 and 6. The CcGMGT1 ORF encoded by unigene 122620 was found to have 54.3% identity with the fenugreek protein sequence and 53.6% identity with the Japonicus protein sequence. The CcGMGT2 ORF encoded by unigene 122567 was found have 62.8% identity with the fenugreek protein sequence and 63.8% identity with the *Japonicus* protein sequence.

Equipped with these partial cDNA sequences, the full length cDNA can be isolated for each gene using the well established techniques of 5' RACE and primer assisted genome walking. The full length cDNA for GMGT1 can be used to express an active coffee grain GMGT protein in plant tissues such as coffee, and in model over-expression organisms, to generate proteins for functional analysis with the coffee mannan synthase protein. Coffee CcMansS and CcGMGT proteins can be expressed at high levels in the same plant, yeast or bacterial cell, which could lead to the generation of substantial amounts of galactomannans being produced by these different types cells.

TABLE 9

In silico distribution of coffee GMGT EST's.

| | | In silico expression | | | | | |
|---|---|---|---|---|---|---|---|
| Gene | Unigene | cccl | cccp | cccwc22w | cccs18w | cccs30w | cccs46w |
| CcGMGT1 | 122620 | 0 | 0 | 0 | 1 | 3 | 2 |
| CcGMGT1 | 122567 | 3 | 0 | 0 | 0 | 0 | 0 |

The number of GMGT EST's found for each unigene in the various *Coffea canephora* libraries is given.

EXAMPLE 6

Isolation of a DNA Sequence Encoding the Complete Polypeptide Sequence of GMGTase 1

Example 5 presented the discovery of a partial cDNA sequence encoding the UDP-Gal dependent mannan specific (1,6)-alpha-D-galactosyltransferase, CcGMGTase 1 (CcGMTG1) from *C. canephora* grain. To confirm the unigene sequence #122620 presented in Example 5, the second longest EST in that unigene (pcccs46w8o23) was sequenced completely. To obtain sequence data for CcGMGTase 1 upstream of the 5' end of the partial cDNA sequence of pcccs46w8o23, 5' RACE was carried out with the primers GMGT-30w15m14-RACE 4 and GMGT-30w15m14-RACE 2 (see Table 10 for the sequences). Using RNA isolated from the grain of cherries from arabica T2308 at the "yellow" stage, cDNA was prepared as described earlier in the methods for this application. A poly dC tail was then added to the arabica cDNA using the enzyme TdT and used in the 5' RACE reaction under the conditions described in the methods section. The first round of 5' RACE used the primers GMGT-30w15m14-RACE 4 and AAP, and the second round of 5' RACE used the primers GMGT-30w15m14-RACE 2 and AUAP. The annealing temperature in both reactions was 60° C. This produced an approximately 1.0-1.1 kilobase pair fragment that was cloned into the pCR-4-TOPO vector and then sequenced.

The 5' RACE generated the clone pVC10 which contained an insert of 1120 bp. Analysis of the complete sequence of this 5' RACE product showed that it encoded the N-terminal region of the coffee GMGTase 1. The complete ORF sequence of the coffee GMGTase 1 was successfully PCR amplified as a single fragment from arabica variety T-2308 genomic DNA using a new set of PCR primers that was designed from the extreme 5' end of pVC10 and the 3' non-coding region of cDNA pcccs46w8o23. These GMGTase 1 specific oligonucleotides GMGT-Fwd1 and GMGT-Rev (Table 11) were then used to PCR amplify a fragment containing the complete ORF sequence of GMGTase 1 from the genomic DNA of arabica T-2308 that had been purified from leaf tissue according to the method described previously (Crouzillat et al. 1996 Theor. Appl. Genet. 93, 205-214). The PCR reaction was performed in a 50 µl reaction as follows: 5 µl of gDNA, 5 µl 10×PCR buffer (ThermoPol buffer), 400 nM of each gene specific primer, 200 µM of each dNTP, and 0.5 U of Taq DNA polymerase (Biolabs). After denaturing at 94° C. for 2 min, the amplification consisted of 40 cycles of 1 min at 94° C., 1.5 minutes at 58° C., and 3 minutes at 72° C. An additional final step of elongation was done at 72° C. for 7 min. The PCR products were then analyzed by agarose gel electrophoresis and ethidium bromide staining. Fragments of the expected size (~1700 pb) were then cloned in pCR4-TOPO using the TOPO TA Cloning Kit for Sequencing (Invitrogen) according to the instructions given by the manufacturer. The inserts of the plasmids generated were then sequenced entirely. Sequence analysis of the clone obtained (pVC11; CaGMGTase1) showed that GMGTase 1 does not contain any introns in the majority of the coding sequence of this gene (introns may still occur in the extreme 5' or 3' coding regions of this gene).

TABLE 10

List of primers used for 5'RACE PCR experiments.

| Primers | Sequences | SEQ ID NO: |
|---|---|---|
| AAP (Abridged Anchor Primer) | 5' GGCCACGCGTCGACTAGTACGGGIIGGGIIGGGIIG 3' | 48 |
| AUAP (Abridged Universal Amplification Primer) | 5' GGCCACGCGTCGACTAGTAC 3' | 49 |
| GMGT-30w15m14-Race4 | 5' CTCCCATACCCAGCGTCCTTAAG 3' | 50 |
| GMGT-30w15m14-Race2 | 5' TTCTCCAGCGTCCCCACG 3' | 51 |

TABLE 11

Sequences of the primers used for the amplification of a genomic sequence encoding the full length protein sequence of CaGMGT1.

| PRIMERS | SEQUENCES | SEQ ID NO: |
|---|---|---|
| GMGT-Fwd1 | 5' AGACAGCAGCCACCATGCC 3' | 52 |
| GMGT-Rev | 5' CCCCGACTTTTAACTTACAACAGA 3' | 53 |

The three clones used to obtain the full-length coffee GMGTase1 polypeptide sequence are presented in FIG. 7. The DNA sequences generated were aligned using the program CLUSTAL W (FIG. 8). This alignment shows that there are some differences in the nucleic acid sequences obtained. However, only two of the base differences in the amino acid sequence region result in amino acid changes (position 432 has L versus P and position has 445 E versus G). The complete amino acid sequence encoded by pVC11 was then aligned with the most homologous DNA sequences found in the GenBank public database. The result of this amino acid sequence alignment is shown in FIG. 9. The CaGMGTase 1 sequence is most highly related to the *Senna occidentalis* Galactomannan galactosyltransferase (65% identity) and had approximately 56-57.6% identity with most of the other protein sequences in FIG. 3, supporting the annotation of the full length polypeptide sequence of CaGMGTase 1 as a Galactomannan galactosyltransferase.

EXAMPLE 7

Characterization of a cDNA Encoding the Complete Polypeptide Sequence of GMGTase 2

Example 5 also presented the discovery of a partial cDNA sequence encoding the UDP-Gal dependent mannan specific (1,6)-alpha-D-galactosyltransferase, CcGMGTase 2 (CcGMGT2) from *C. canephora* leaves. This unigene sequence (unigene #122567) was generated using three homologous EST sequences. To confirm the unigene sequence data, and extend the sequence data to cover the 3' end of the sequence, the longest EST clone in that unigene set was sequenced (clone pccc126f9). The alignment of the complete DNA sequence of pccc126f9 versus the unigene sequence #122567 is presented in FIG. 10. As expected, the complete sequence of pccc126f9 contained the 3' end of the CcGMGTase 2, as indicated by the presence of a poly A tail. The ORF encoded by pccc126f9 also contained the N-terminal region of GMGTase 2. The DNA sequence at the 5' end of pccc126f9 is nearly identical to that of the unigene. However, a closer examination of the unigene sequence reveals that the first methionine codon of the pccc126f9 sequence (ATG) was actually ATC in the unigene sequence, thus the N-terminal amino acid sequence obtained from the unigene DNA sequence was not seen. The amino acid sequence encoded by pccc126f9 was then aligned with several of the most closely related sequences found in the public GenBank database (FIG. 11). Examination of this alignment indicates that, while the coffee GMGTase 1 and GMGTase 2 sequences have significant regions of homology (they have approximately 52% identity), they are clearly encoded by different genes. This alignment also again shows that the coffee GMGTase 2 is also highly related to a group of proteins annotated as galactosyltransferases. In conclusion, the evidence presented here strongly indicates that the cDNA clone isolated from the coffee leaf EST library (pccc126f9) encodes the complete polypeptide sequence for a coffee GMGTase which is expressed in the coffee leaf.

EXAMPLE 8

Expression Analysis of Coffee GMGTase 1

The expression levels of GMGTase 1 in various arabica and robusta tissues was analysed using quantitative RT-PCR and the approach of relative quantification (expression relative to rp139). The method employed was similar to that described earlier to measure the expression of the coffee grain mannan synthase. The specific primers and probe sets used are presented in Table 12. Measurements of the amplification efficiency of the primer/TaqMan probe set demonstrated they were in an acceptable range of efficiency. The cDNA was prepared as described earlier in this application using the SuperScript III (Invitrogen).

TABLE 12

Sequences of the primers and probes used for the quantitative RT-PCR experiments.

| Primers | Sequences | SEQ ID NO: |
|---|---|---|
| rp139F1 | 5' GAACAGGCCCATCCCTTATTG 3' | 54 |
| rp139R1 | 5' CGGCGCTTGGCATTGTA 3' | 55 |
| rp139MGB1 VIC | 5' ATGCGCACTGACAACA 3' | 56 |
| GMGT1-F1 | 5' CGCCTCTGCCGTTCGA 3' | 57 |
| GMGT1-R1 | 5' ATTTCTAGGAAGCGCCTCCAA 3' | 58 |
| GMGT1-MGB1 FAM | 5' CCAGCATCGGACCTT 3' | 59 |

Results are presented in FIG. 12 and demonstrate that GMGTase 1 is primarily expressed in the grain of both robusta and arabica. Interestingly, there is an approximately ten fold difference in the RQ found for the arabica versus robusta cDNA samples tested. It is possible this expression difference may be contribute to some variation in either the galactomannan level and/or structure in the grain of the two species. It is also observed that the GMGTase 1 expression in robusta is highest in the yellow stage. This contrasts with arabica where the highest expression is seen in small green and large green stages. GMGTase 1 expression was also detected at lower levels in most of the other tissues tested, again with higher expression being detected in arabica than robusta. Finally, it is noted that the expression pattern observed for GMGTase 1 mirrors the expression pattern seen for mannan synthase expression. Because these two proteins are proposed to work together in galactomannan synthesis, the GMGTase 1 expression data further supports that GMGTase 1 is a key participant in the synthesis of coffee grain galactomannans.

REFERENCES

Altschul S. F., Madden T. L., Schaffer A. A., Zhang J., Zhang Z., Miller W. and Lipman D. J. (1997) Gapped BLAST and PSI-BLAST: a new generation of protein database search programs. *Nucleic Acids Res.* 25: 3389-3402.
Bacic A, Harris P, Stone B (1988) Structure and function of plant cell walls. In J Priess, ed, The biochemistry of plants;

a comprehensive treatise, Vol 14 Carbohydrates, Academic Press, New York, pp 297-371

Buckeridge M, Pessoa dos Santos H, Tine M (2000) Mobilization of storage cell wall polysaccharides in seeds. Plant Physiol Biochem 38: 141-156

Charles-Bernard M, Kraehenbuehl K, Rytz A, Roberts D (2005) Interactions between volatile and non-volatile coffee components. 1. Screening of non-volatile components. J Agric Food Chem 53: 4417-4425

Crouzillat D., Lerceteau E., Petiard V., Morera J., Rodriguez H., Walker D., Philips W. R. R., Schnell J., Osei J. and Fritz P. (1996). Theobroma cacao L.: a genetic linkage map and quantitative trait loci analysis. *Theor Appl Genet.* 93: 205-214.

Cutler S, Somerville C (1997) Cloning in silico. Curr Biol 7: R108-R111

Dhugga K S, Barreiro R, Whitten B, Stecca K, Hazebroek J, Randhawa G S, Dolan M, Kinney A J, Tomes D, Nichols S, Anderson P. (2004) Guar seed beta-mannan synthase is a member of the cellulose synthase super gene family. *Science*. 2004 Jan. 16; 303 (5656):363-6.

Edwards M, Choo T, Dickson C, Scott C, Gridley M, Reid J (2004) The seeds of *Lotud japonicus* lines transformed with sense, antisense, and sense/antisense galactomannan galactosyltransferase constructs have structurally altered galactomannans in their endosperm cell walls. Plant Physiol 134: 1153-1162

Edwards M, Scott C, Gidley M, Reid J (1992) Control of mannose/galactose ratio during galactomannan formation in developing legume seeds. Planta 187: 67-74

Fischer M, Reimann S, Trovato V, Redgwell R J (2001) Polysaccharides of green Arabica and Robusta coffee beans. Carbohydrate Research 330: 93-101

Fry S (2004) Primary cell wall metabolism: tracking the careers of wall polymers in living plant cells. New Phytologist 161: 641-675

Handford M, Baldwin T, Goubet F, Prime T, Miles I, Yu X, Dupree P (2003) Localization and characterization of cell wall mannan polysaccharised in *Arabidopsis thaliana*. Planta 218: 27-36

Hanford M, Baldwin T, Goubet F, Prime T, Miles J, Yu X, Dupree P (2003) Localisation and characterization of cell wall mannan polysaccharides in Arabidopsis thaliana. Planta 218: 27-36

Hazen S P, Scott-Craig J S, Walton J D (2002) Cellulose synthase-like genes of rice. Plant Physiol 128: 336-340

Illy A, Viani R (1995) Expresso Coffee. The chemistry of quality. Academic Press, London, pp 5-7

Joersbo M, Marcussen J, Brunstedt J (2001) In vivo modification of the cell wall polysaccharide galactomannan of guar transformed with an alph-galactosidase gene cloned from senna. Molecular Breeding 7: 211-219

Keegstra K, Raikhel N (2001) Plant glycosyltransferases. Curr Opin Plant Biol 4: 219-224

Liepman A, Wilkerson C, Keegstra K (2005a) Expression of cellulose synthase-like (Csl) genes in insect cells reveals that CslA family members encode mannan synthases. Proc Natl Acad Sci 102: 2221-2226

Lundqvist, J., Teleman, A., Junel, L., Zacchi, G., Dahlman, O., Tjerneld, F., Stalbrand, H (2002), Isolation and characterization of galactomannan from spruce (*Picea abies*) Carbohydr Polym 48, 29-39

Marraccini P., Deshayes A., Pétiard V. and Rogers W. J. 1999. Molecular cloning of the complete 11S seed storage protein gene of *Coffea arabica* and promoter analysis in the transgenic tobacco plants. *Plant Physiol. Biochem.* 37:273-282.

Marraccini, P., Deshayes, A., and Rogers, W. J. Coffee plant with reduced alpha-D-galactosidase. EP1436402. 2004.
Ref Type: Patent Marraccini P, Rogers J, Allard C, Andre M-L, Caillet V, Lacoste N, Lausane F, Michaux S (2001) Molecular and biochemical characterization of endo-beta-mannanases from germination coffee (*Coffea arabica*) grains. Planta 213: 296-308

Marraccini P, Courjault C, Caillet V, Lausanne F, LePage B, Rogers W, Tessereau S, and Deshayes A. (2003) Rubisco small subunit of *Coffea arabica*: cDNA sequence, gene cloning and promoter analysis in transgenic tobacco plants. *Plant Physiol. Biochem.* 41:17-25.

Marraccini P, Rogers J, Caillet V, Deshayes A, Granato D, Lausane F, Lechat S, Pridmore D, Petiard V (2005) Biochemical and molecular characterization of alpha-D-galactosidase from coffee beans. Plant Physiology and Biochemistry Matheson M (1990) Mannose-based polysaccharides. Methods Plant Biochem 12: 371-413

Nunes F, Coimbra M, Duarte A, Delgadillo I (1997) J Agric Food Chem 45: 3238-3243

Oosterveld A, Harmsen J S, Voragen A G J, Schols H A (2003) Extraction and characterization of polysaccharides from green and roasted *Coffea arabica* beans. Carbohydrate Polymers 52: 285-296

Pettolino F, Hoogenraad N, Ferguson C, Bacic A, Johnson E, Stone B (2001) A (1-4)-beta-mannan specific monoclonal antibody and its use in the immunocytochemical location of galactomannans. Planta 214: 235-242

Redgwell R, Curti D, Rogers J, Nicolas P, Fischer M (2003) Changes to the galactose/mannose ratio in galactomannans during coffee bean (*Coffea arabica* L.) development: implications for in vivo modification of galactomannan synthesis. Planta 217: 316-326

Redgwell R J, Trovato V, Curti D, Fischer M (2002) Effect of roasting on degradation and structural features of polysaccharises in Arabica coffee beans. Carbohydrate Research 337: 421-431

Reid J (1985) Structure and function in legume-seed polysaccharides. In C Brett, J Hillman, eds, Biochemistry of plant cell walls, Cambridge University Press, Cambridge, pp 259-268

Reid J, Bewley J (1979) A dual role for the endosperm and its galactomannan reserves in the germinative physiology of fenugreek (*Trigonella foenum-graecum* L.) an endospermic leguminous seed. Planta 147: 145-150

Richmond T A, Somerville C R (2000) The cellulose synthase superfamily. Plant Physiol 124: 495-498

Schroder, R., Nicolas, P., Vincent, S., Fischer, M, Reymond, S., and Redgewell, R. (2001), Purification and characterization of a galactoglucomannan from kiwi fruit (*Actinidia deliciosa*) Carbohydr Res. 331, 291-306

Sims, I. and Craik, D., and Bacic, A. (1997) Structural characterization of galactoglucomannan secreted by suspension-cultured cells of *Nicotiana plumbaginifolia* Carbohydr Res 303, 79-92

Somerville C, Bauer S, Brininstool G, Facette M, Hamann T, Milne J, Osborne E, Paredez A, Persson S, Raab T, Vorwerk S, Youngs H (2004a) Toward a systems approach to understanding plant cell walls. Science 306: 2206-2211

Somerville C, Bauer S, Brininstool G, Facette M, Hamann T, Milne J, Osborne E, Paredez A, Persson S, Raab T, Vorwerk S, Youngs H (2004b) Toward a systems approach to understanding plant cell walls. Science 306: 2206-2211

Somerville C, Bauer S, Brininstool G, Facette M, Hamann T, Milne J, Osborne E, Paredez A, Persson S, Raab T, Vorwerk S, Youngs H (2005) Toward a systems approach to understanding plant cell walls. Science 306: 2206-2211

Sunderland P, Hallet I, MacRea E, Fischer M, Redgwell R (2004) Cytochemistry and immunolocalization of polysaccharides and proteoglycans in the endosperm of green Arabica coffee beans. Protoplasma 223: 203-211

Yeretzian C, Jordan A, Badoud R, Lindinger W (2005) From the green bean to the coffee cup: investigating coffee roasting by on-line monitoring of volatiles. Eur Food Res Technol 214: 92-104

The present invention is not limited to the embodiments described and exemplified above, but is capable of variation and modification within the scope of the appended claims.

What is claimed:

1. A nucleic acid molecule isolated from *Coffea* spp. comprising a coding sequence that encodes a galactosyltransferase having an amino acid sequence greater than about 90% identical to any one of SEQ ID NOS: 15-18.

2. The nucleic acid molecule of claim 1, wherein the galactosyltransferase comprises any one of SEQ ID NOS: 15-18.

3. The nucleic acid molecule of claim 1, comprising any one of SEQ ID NOS: 11-14.

4. The nucleic acid molecule of claim 1, wherein the coding sequence is an open reading frame of a gene, or a mRNA, or a cDNA.

5. The coding sequence of the nucleic acid molecule of claim 1, contained within a vector.

6. The vector of claim 5, which is an expression vector selected from the group of vectors consisting of plasmid, phagemid, cosmid, baculovirus, bacmid, bacterial, yeast and viral vectors.

7. The vector of claim 5, wherein the coding sequence of the nucleic acid molecule is operably linked to a constitutive promoter, an inducible promoter, or a tissue-specific promoter.

8. The vector of claim 7, wherein the tissue specific promoter is a seed specific promoter.

9. The vector of claim 8, wherein the seed specific promoter is a coffee seed specific promoter.

10. A host cell transformed with the vector of claim 5.

11. The host cell of claim 10, selected from the group consisting of plant cells, bacterial cells, fungal cells, insect cells and mammalian cells.

12. The host cell of claim 11, which is a plant cell selected from the group of plants consisting of coffee, tobacco, Arabidopsis, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, petunia, zinnia, and turfgrasses.

13. A fertile plant produced from the plant cell of claim 12.

14. A method of modulating extractability of solids from coffee beans, comprising modulating production or activity of a galactosyltransferase within coffee seeds, wherein the galactosyltransferase comprises an amino acid sequence greater than about 90% identical to any one of SEQ ID NOS: 15-18.

15. The method of claim 14, comprising increasing production or activity of the galactosyltransferase.

16. The method of claim 14, comprising increasing expression of a gene encoding the galactosyltransferase within the coffee seeds.

17. The method of claim 14, comprising introducing a galactosyltransferase-encoding transgene into the plant.

18. The method of claim 14, comprising decreasing production or activity of the galactosyltransferase.

* * * * *